US007745671B2

(12) United States Patent
Yamaguchi et al.

(10) Patent No.: US 7,745,671 B2
(45) Date of Patent: Jun. 29, 2010

(54) METHOD FOR PRODUCING SCYLLO-INOSITOL

(75) Inventors: Masanori Yamaguchi, Zama (JP); Yuichi Kita, Atsugi (JP); Tetsuya Mori, Ebina (JP); Kenji Kanbe, Yokohama (JP); Akihiro Tomoda, Tokyo (JP); Atsushi Takahashi, Kawasaki (JP); Wakako Ichikawa, Yokohama (JP)

(73) Assignee: Hokko Chemical Industry Co., Ltd., Chuo-ku, Tokyo (JP)

( * ) Notice: Subject to any disclaimer, the term of this patent is extended or adjusted under 35 U.S.C. 154(b) by 564 days.

(21) Appl. No.: 10/576,030

(22) PCT Filed: Oct. 14, 2004

(86) PCT No.: PCT/JP2004/015174

§ 371 (c)(1),
(2), (4) Date: Apr. 13, 2006

(87) PCT Pub. No.: WO2005/035774

PCT Pub. Date: Apr. 21, 2005

(65) Prior Publication Data

US 2006/0240534 A1 Oct. 26, 2006

(30) Foreign Application Priority Data

| Oct. 14, 2003 | (JP) | ............................. 2003-353490 |
| Oct. 14, 2003 | (JP) | ............................. 2003-353491 |
| Jan. 27, 2004 | (JP) | ............................. 2004-018128 |
| Jun. 30, 2004 | (JP) | ............................. 2004-194088 |

(51) Int. Cl.
*C07C 35/16* (2006.01)
*C07H 1/06* (2006.01)
*C07C 35/46* (2006.01)

(52) U.S. Cl. ...................................... 568/833; 536/127
(58) Field of Classification Search ................. 568/833; 536/127
See application file for complete search history.

(56) References Cited

U.S. PATENT DOCUMENTS 5,412,080 A 5/1995 Kishi et al.

FOREIGN PATENT DOCUMENTS

| DE | 34 05 663 | 8/1985 |
| JP | 60-248637 | 12/1985 |
| JP | 04-126075 | 4/1992 |
| JP | 05-192163 | 8/1993 |
| JP | 06-007158 | 1/1994 |
| JP | 09-140388 | 6/1997 |
| JP | 2003-102492 | 4/2003 |

OTHER PUBLICATIONS

Sigma-Aldrich Technical Information Bulletin AL-142, Sigma-Aldrich, http://www.sigmaaldrich.com/, accessed online on May 31, 2008.* machine translation of Merck DE 3405663, European Patent Office, http://www.worldlingo.com, accessed online on Mar. 28, 2008.*

Husson et al. Carbohydrate Research, 1998, 307, p. 163-165.*

Weser, U. Stucture & Bonding, 1967, Springer Berlin / Heidelberg, vol. 2, p. 160-180.*

Mopper Analytical Biochemistry, 1978, 87, p. 162-168.* entry for separation and purification, Encyclopedia Britannica Online, 2009, http://www.search.eb.com/eb/article-80483, accessed online on Jun. 18, 2009.*

Kiely et al. Annals of the New York Academy of Sciences, 1969, 165(2), p. 559-563.*

Wood, et al. "The Genome of the Natural Genetic Engineer *Agrobacterium tumefaciens* C58," Science, vol. 294, pp. 2317-2323, Dec. 14, 2001.

International Search Report dated Jan. 25, 2005.

Sasaki, et al. "Preparative-Scale Separation by Anion-Exchange Chromatography of Six Per-C-Deuterated Inositol Epimers Produced During C-$^1$H-C-$^2$H Exchange Reactions with Raney Nickel in Duterium Oxide," Carbohydrate Research, vol. 166, No. 2, pp. 171-180, 1987.

MacRae, et al. "A Robust and Selective Method for the Quantification of Glycosylphosphatidylinositols in Biological Samples," *Glycobiology*, vol. 15, No. 2, pp. 131-138, Feb. 2005.

Charalampous, et al. "Isolation of *myo*-Inositol from Yeast and Its Quantitative Enzymatic Estimation," *The Journal of Biological Chemistry*, vol. 225, No. 2, pp. 575-583, Apr. 1957.

Khym, et al. "The Separation of Sugars by Ion Exchange," *Journal of the American Chemical Society*, vol. 74, pp. 2090-2094, Apr. 20, 1952.

(Continued)

*Primary Examiner*—Jonathan S Lau
(74) *Attorney, Agent, or Firm*—Knobbe, Martens, Olson & Bear, LLP

(57) ABSTRACT

It is intended to provide a novel NAD$^+$-independent myo-inositol 2-dehydrogenase which converts myo-inositol into scyllo-inosose in the absence of NAD$^+$; a novel enzyme scyllo-inositol dehydrogenase which stereospecifically reduces scyllo-inosose into scyllo-inositol in the presence of NADH or NADPH; and a novel microorganism which belongs to the genus *Acetobacter* or *Burkholderia* and can convert myo-inositol into scyllo-inositol. By using these enzymes or the microorganism, scyllo-inositol is produced. Furthermore, scyllo-inositol is purified by adding boric acid and a metal salt to a liquid mixture containing scyllo-inositol and a neutral saccharide other than scyllo-inositol to form a scyllo-inositol/boric acid complex, separating the complex from the liquid mixture, dissolving the thus separated complex in an acid to give an acidic solution or an acidic suspension and then purifying scyllo-inositol from the acidic solution or the acidic suspension.

4 Claims, 1 Drawing Sheet

OTHER PUBLICATIONS

Zill, et al. "Further Studies on the Separation of the Borate Complexes of Sugars and Related Compounds by Ion-Exchange Chromatography," *Journal of the American Chemical Society*, vol. 75, pp. 1339-1344, Mar. 1953.

Criddle, et al. "Myo-Inositol Dehydrogenase(s) from Acetomonas Oxydans," *Molecular & Cellular Biochemistry*, vol. 16, No. 1, pp. 3-8, May 31, 1977.

Freivogel, et al. "Myo-Inositol Dehydrogenase from the Membrane of Gluconobacter Oxydans," *Biological Chemistry*, vol. 373, No. 9, pp. 767-768, Sep. 1, 1992.

"*Escherichia coli* K12 MG1655 Section 148 of 400 of the Complete Genome," retrieved from EBI accession No. EM_PRO:AE000258, Nov. 30, 2002.

Stein, et al. "Myo-Inositol Dehydrogenase from the Acido- and Thermophilic Red Alga *Galdieria Sulphuraria*," *Phytochemistry*, vol. 46, No. 1, pp. 17-20, Sep. 1997.

Supplementary Partial European Search Report dated Jan. 26, 2007.

McLaurin, et al. "Inositol Stereoisomers Stabilize an Oligomeric Aggregate of Alzheimer Amyloid β Peptide and Inhibit Aβ-Induced Toxicity," *The Journal of Biological Chemistry*, vol. 275, No. 24, pp. 18495-18502, Jun. 16, 2000.

Anderson, et al. "The Catalytic Hydrogenation of Polyhydric Phenols. I. The Synthesis of *meso*-Inositol, Scyllitol and a New Isomeric Cyclitol," *Journal of the American Chemical Society*, vol. 70, pp. 2931-2935, Sep. 1948.

Kiely, et al. "Cyclization of D-*xylo*-Hexos-5-ulose, a Chemical Model for the Biosynthesis of *myo*- and *scyllo*-Inositols," *Journal of the American Chemical Society*, vol. 90, pp. 3289-3290, Jun. 5, 1968.

Schwesinger, et al. "Chemistry of cis-trioxatris-σ-homobenzene. Substitutions with Monovalent Nucleophilic Compounds," *Angewandte Chemie*, vol. 85, No. 24, pp. 1110-1111, 1973.

Magasanik, et al. "The Stereochemistry of an Enzymatic Reaction: the Oxidation of *l*-, *d*-, and *epi*-Inositol by *Acetobacter suboxydans*," *The Journal of Biological Chemistry*, vol. 174, pp. 173-188, 1948.

Larner, et al. "Inositol Dehydrogenase from *Aerobacter aerogenes*," *Archives of Biochemistry and Biophysics*, vol. 60, pp. 352-363, 1956.

Ramaley, et al. "Purification and Properties of *Bacillus subtilis* Inositol Dehydrogenase," *The Journal of Biological Chemistry*, vol. 254, No. 16, pp. 7684-7690, Aug. 25, 1979.

Yoshida, et al. "Cloning and Nucleotide Sequencing of a 15 kb Region of the *Bacillus subtilis* Genome Containing the *iol* Operon," *Microbiology*, vol. 140, pp. 2289-2298, 1994.

Dworsky, et al. Die Überführung von *myo*-Inosit in Chinoide Substanzen in *Pseudomonas beijerinckii*, 1. Mitt.:, *Monatshefte für Chemie*, vol. 100, pp. 1327-1337, 1969.

Reber, et al. "*myo*-Inositol Transport System in *Pseudomonas putida*," *Journal of Bacteriology*, vol. 131, No. 3, pp. 872-875, Sep. 1977.

Hipps, et al. "The Identification of *myo*-Inositol:NAD (P)+Oxidoreductase in Mammalian Brain," *Biochemical and Biophysical Research Communications*, vol. 68, No. 4, pp. 1133-1138, 1976.

Weissbach, Arthur. "Scyllitol Diborate," *Journal of Organic Chemistry*, vol. 23, pp. 329-330, Feb. 1958.

* cited by examiner

METHOD FOR PRODUCING SCYLLO-INOSITOL

RELATED APPLICATIONS

This application is the U.S. National Phase under 35 U.S.C. §371 of International Application PCT/JP2004/015174, filed Oct. 14, 2004, which claims priority to JP 2003-353490, filed Oct. 14, 2003; JP 2003-353491, filed Oct. 14, 2003; JP 2004-018128, filed Jan. 27, 2004; and JP 2004-194088, filed Jun. 30, 2004.

TECHNICAL FIELD

The present invention relates to a method of producing scyllo-inositol from myo-inositol by means of microbial conversion.

The present invention also relates to a novel $NAD^+$-independent myo-inositol 2-dehydrogenase and a method of producing the same. The present invention also relates to a method of screening a microorganism for producing scyllo-inosose based on an activity of $NAD^+$-independent myo-inositol 2-dehydrogenase. The present invention further relates to a method of producing scyllo-inosose and scyllo-inositol using an $NAD^+$-independent myo-inositol 2-dehydrogenase or a strain having a high activity of said enzyme.

The present invention also relates to a novel enzyme, scyllo-inositol dehydrogenase and a method of producing scyllo-inositol using said enzyme. Specifically, the present invention relates to a novel enzyme, scyllo-inositol dehydrogenase which catalyzes an oxidation-reduction reaction between scyllo-inositol and scyllo-inosose and stereospecifically reduces scyllo-inosose into scyllo-inositol in the presence of NADH or NADPH; and a method of producing scyllo-inositol using the enzyme.

The present invention further relates to a method of efficiently producing scyllo-inositol from a liquid mixture containing scyllo-inositol and neutral sugars other than scyllo-inositol.

The scyllo-inositol can be used as a therapeutic agent for treatment of an Alzheimer disease, a raw material for synthesis of bioactive substances, or a raw material for synthesis of liquid crystal compounds.

BACKGROUND ART

Myo-inositol is a naturally-occurring known substance represented by the following steric structural formula (A).

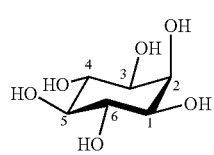

(A)

Scyllo-inosose is a known substance represented by the steric structural formula (B).

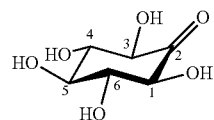

(B)

Furthermore, scyllo-inositol is a known substance represented by the following steric structural formula (C).

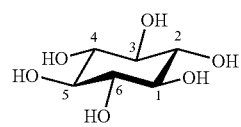

(C)

Scyllo-inositol is one of stereoisomers of myo-inositol and is a substance widely found among animals and plants. Scyllo-inosose is a compound having a structure in which an axial hydroxyl group at the second position of myo-inositol is oxidized, and exists generally as a natural compound.

Scyllo-inositol is a substance expected for applications such as a therapeutic agent for an Alzheimer disease (see Non-Patent Document 1), a raw material for synthesis of bioactive substances (Patent Document 1), or a raw material for synthesis of liquid crystal compounds (Patent Document 2).

Examples of a method of producing scyllo-inosose or scyllo-inositol by means of a chemical synthetic procedure include: (i) a method of obtaining scyllo-inositol by reducing hexahydroxybenzene with Raney nickel (Non-Patent Document 2); (ii) a method of obtaining scyllo-inositol by reducing scyllo-inosose obtained from a glucofuranose derivative through a reaction involving five steps (Non-Patent Document 3); (iii) a method of obtaining scyllo-inositol using as a raw material cis-trioxa-tris-homobenzene through a reaction involving four steps or more (Non-Patent Document 4); and (iv) a method of obtaining scyllo-inositol including oxidizing myo-inositol with a platinum catalyst to thereby obtain scyllo-inosose, and subjecting the scyllo-inosose to esterification followed by reduction and hydrolysis (see Patent Document 2).

As a method of converting myo-inositol into scyllo-inositol using a microorganism, a method using a bacterium belonging to the genus *Agrobacterium* is known (Patent Document 3). However, this method is not applicable for an industrial-scale production because of low yield of scyllo-inositol and generation of other converted products.

Meanwhile, a bacterium belonging to the genus *Acetobacter* (see Non-Patent Document 5) is known to act on myo-inositol to absorb oxygen to thereby oxidize myo-inositol into scyllo-inosose. However, its detailed mechanism has not been studied.

The enzyme which oxidizes myo-inositol into scyllo-inosose (myo-inositol 2-dehydrogenase) has been reported from a number of organisms such as animals, algae, yeasts, and bacteria, and it is an enzyme that widely exists in nature. Examples of a typical microorganism having the enzyme include *Aerobacter aerogenes* (see Non-Patent Document 6), bacteria belonging to the genus *Bacillus* (Non-Patent Document 7 and 8; Patent Documents 4-6), and bacteria belonging to the genus *Pseudomonas* (Non-Patent Document 9 and 10).

However, the myo-inositol 2-dehydrogenases in those reports are $NAD^+$-dependent enzymes, therefore they require $NAD^+$ or $NADP^+$ for oxidation. When the enzyme is subjected to an industrial-scale reaction, fermentative production must be employed in order to recycle those co-enzymes, resulting in decomposition of part of substrates. In addition, there had been problems in industrial-scale production such that the concentration of the substrate should be kept low.

Meanwhile, there is a report of the presence of a scyllo-inositol dehydrogenase in a bovine brain and a fat tissue of a cockroach (Non-Patent Document 11). When scyllo-inosose as a substrate is reduced by this enzyme with NADPH, both of scyllo-inositol and myo-inositol are reported to be generated. However, the enzyme has low substrate specificity, a highly purified enzyme was not used, and other properties are unknown, therefore the enzyme may be an alcohol dehydrogenase having low substrate specificity. Therefore, the enzyme has not been described in Handbook of Enzymes (published by Asakura Shoten). As described above, although reports on animals exist, it has not been ascertained whether these reports are true.

Furthermore, there is also a known method of producing scyllo-inositol by chemically reducing scyllo-inosose produced by microbial oxidation (Patent Document 7). Since the substance obtained by the chemical reduction of scyllo-inosose is a mixture of scyllo-inositol and myo-inositol, the mixture had to be desalted and purified, followed by separation of scyllo-inositol having low solubility from the concentrated solution by crystallization. Thus, those methods have required many operations and thus there has been a room for improvement with respect to the yield of scyllo-inositol. Under such circumstances, the development of a method of producing purified scyllo-inositol from a mixture of scyllo-inositol and myo-inositol which is obtained by reduction of scyllo-inosose, or the like, has been expected in order to produce scyllo-inositol conveniently and efficiently.

When scyllo-inosose is reduced using $NaBH_4$ in a solution, the solution after the reaction contains myo-inositol, scyllo-inositol, and a small amount of a scyllo-inositol/boric acid complex. For such scyllo-inositol/boric acid complex, there has been known a method of obtaining scyllo-inositol involving: filtrating the complex as a precipitate; dissolving the precipitate in diluted sulfuric acid; adding thereto methanol to subject it to azeotropy with boric acid; removing the boric acid; and desalting the remaining solution using an ion exchange resin (Non-Patent Document 12).

The scyllo-inositol/boric acid complex is a substance represented by the following steric structural formula (D).

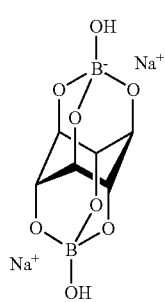
(D)

However, in the above-described method of reducing scyllo-inosose using $NaBH_4$, the ratio of the generated scyllo-inositol/boric acid complex is low, and scyllo-inositol is also generated in the solution. Therefore, the complex and components in the solution had to be separated to thereby obtain scyllo-inositol from each of those. Furthermore, a large amount of an organic solvent has been required to obtain scyllo-inositol from the complex, there has been a room for improvement in an economical viewpoint. Thus, there have been demanded a method of producing scyllo-inositol conveniently and efficiently in industrial-scale production.

[Patent Document 1] U.S. Pat. No. 5,412,080
[Patent Document 2] DE 3,405,663
[Patent Document 3] JP09-140388A
[Patent Document 4] JP04-126075A
[Patent Document 5] JP05-192163A
[Patent Document 6] JP06-007158A
[Patent Document 7] JP2003-102492A
[Non-Patent Document 1] The Journal of Biological Chemistry (US), 2000, vol. 275, No. 24, p. 18495-18502
[Non-Patent Document 2] Journal of the American Chemical Society (US), 1948, vol. 70, p. 2931-2935)
[Non-Patent Document 3] Journal of the American Chemical Society (US), 1968, vol. 90, p. 3289-3290
[Non-Patent Document 4] Angewandte Chemie (Germany), 1973, vol. 85 p. 1110-1111
[Non-Patent Document 5] The Journal of Biological Chemistry (US), 1948, vol. 174, p. 173-188
[Non-Patent Document 6] Archives of Biochemistry and Biophysics (US), 1956, J, Larner et al., vol. 60, p. 352-363
[Non-Patent Document 7] The Journal of Biological Chemistry (US), 1979, vol. 254, p. 7684-7690
[Non-Patent Document 8] Microbiology (US), 1994, vol. 140, p. 2289-2298
[Non-Patent Document 9] Monatshefte fur Chemie (Germany), 1969, vol. 100, p. 1327-1337
[Non-Patent Document 10] Journal of Bacteriology (US), 1977, vol. 131, p. 872-875
[Non-Patent Document 11] Biochemical and Biophysical Research Communications (US), vol. 68, p. 1133, 1976
[Non-Patent Document 12] Journal of Organic Chemistry (US), 1958, vol. 23, p. 329-330

DISCLOSURE OF THE INVENTION

It is an object of the present invention to provide a method of producing scyllo-inositol directly from myo-inositol at high yields by means of only microbial conversion.

Furthermore, it is an object of the present invention to provide a novel enzyme for catalyzing a conversion reaction from myo-inositol into scyllo-inosose, and a novel method of producing scyllo-inosose and scyllo-inositol using the enzyme.

Furthermore, it is an object of the present invention to provide a novel scyllo-inositol dehydrogenase which catalyzes an oxidation-reduction reaction between scyllo-inositol and scyllo-inosose, and stereospecifically reduces scyllo-inosose into scyllo-inositol under the presence of NADH or NADPH, and a novel method of producing scyllo-inositol using the enzyme.

Furthermore, it is an object of the present invention to provide a novel method of efficiently producing scyllo-inositol having high purity from a liquid mixture containing scyllo-inositol and neutral sugars other than scyllo-inositol.

The inventors of the present invention have studied to search a microorganism capable of producing scyllo-inosose from myo-inositol, and have found a bacterium belonging to the genus *Acetobacter* which was separated from nature (AB10253 strain). The strain was deposited in International Patent Organism Depositary, National Institute of Advanced Industrial Science and Technology with an Accession number of FERM P-18868 (International depositary number FERM BP-10136). This strain was used to establish a method of producing scyllo-inosose from myo-inositol, and a method of producing scyllo-inositol from the obtained scyllo-inosose by means of chemical reduction (JP 2003-102492 A).

Subsequently; in order to improve the ability to convert into scyllo-inosose, the strain was subjected to breeding by mutation. By this operation, the inventors have found that there exist some strains which biologically reduce scyllo-inosose generated from myo-inositol and generate a small amount of scyllo-inositol, among the mutant strains. Then, the inventors of the present invention subjected those strains to breeding by mutation, in order to obtain a strain which produces and accumulates mainly scyllo-inositol directly from myo-inositol by means of only conversion by culture. As a result, they have succeeded in obtaining a mutant strain which meets the object, that is, a strain which has acquired an ability to reduce scyllo-inosose generated by the reduction of myo-inositol into scyllo-inositol and accumulating the scyllo-inositol in a medium.

Furthermore, although a conversion ability is lower than that of the AB10253 strain, strains each capable of generating scyllo-inositol from myo-inositol have been found in nature. Identification using their nucleotide sequences of 16Sr RNA has confirmed that those strains are microorganisms each belonging to *Acetobacter cerevisiae, Acetobacter malorum*, or *Burkholderia andropogonis*.

The inventors of the present invention have found that scyllo-inositol can be efficiently produced by using those microorganisms.

The inventors of the present invention have considered that if an enzyme capable of efficiently converting myo-inositol into scyllo-inosose can be acquired, efficient production of scyllo-inosose from a high substrate concentration of myo-inositol is possible by using such enzyme. Also, they considered that if a strain having a high activity of such enzyme can be isolated by screening, such strain is able to be used for the production of scyllo-inosose.

Under a hypothesis that there is a novel type of $NAD^+$-independent myo-inositol 2-dehydrogenase which has not been known so far and capable of catalyzing a conversion reaction from myo-inositol into scyllo-inosose, the inventors of the present invention have made extensive studies to obtain such an enzyme. As a result, they have found that $NAD^+$-independent myo-inositol 2-dehydrogenase is present in *Acetobacter* sp. AB10253 strain belonging to the genus *Acetobacter*. The inventors of the present invention have succeeded in efficiently producing scyllo-inosose by using this enzyme or a microorganism having a high activity of this enzyme, and in efficiently producing scyllo-inositol with high purity by reducing the obtained scyllo-inosose.

Next, the inventors of the present invention have studied how myo-inositol is converted into scyllo-inositol in the microbial cells of the strain which produces scyllo-inositol directly from myo-inositol. As a result, a hydroxyl group at the second position of the myo-inositol is oxidized in an oxygen-dependent manner to generate scyllo-inosose, and then scyllo-inositol is formed by the function of an enzyme having an activity of reducing scyllo-inosose into scyllo-inositol in NADH or NADPH-dependent manner. Based on such an activity, the inventors have succeeded in purifying an enzyme having an activity of reducing scyllo-inosose into scyllo-inositol. They also found that this enzyme has an activity to stereospecifically reduce scyllo-inosose into scyllo-inositol in an NADPH-dependent manner and an activity to oxidize scyllo-inositol into scyllo-inosose in an $NADP^+$-dependent manner, and named "scyllo-inositol dehydrogenase". In addition, this enzyme has an ability to oxidize a hydroxyl group at the fifth position of myo-inositol, therefore this enzyme can also be referred to as myo-inositol 5-dehydrogenase.

Furthermore, the inventors have succeeded in cloning of genes each encoding a scyllo-inositol dehydrogenase by PCR from genomes of *Escherichia coli*, the genus *Agrobacterium, Bacillus subtilis*, and *Xanthomonas campestris*.

Furthermore, since the enzyme performs an oxidation-reduction reaction in an $NAD^+$ or $NADP^+$-dependent manner, the inventors of the present invention considered that scyllo-inositol can be directly converted from myo-inositol via scyllo-inosose by combining the enzyme and a known myo-inositol 2-dehydrogenase (having an activity to reduce scyllo-inosose into myo-inositol in $NAD^+$ or $NADP^+$-dependent manner: EC 1.1.1.18)(see: FIG. 1), and they have succeeded.

Moreover, the inventors of the present invention have considered that in order to produce scyllo-inositol efficiently from a liquid mixture containing scyllo-inositol and neutral sugars such as myo-inositol which is obtained by reduction of scyllo-inosose, it is advantageous to form a scyllo-inositol/boric acid complex. On the basis of such consideration, the inventors of the present invention have extensively studied on a method of efficiently bringing only scyllo-inositol in a liquid mixture containing scyllo-inositol and myo-inositol into such a scyllo-inositol/boric acid complex. As a result, they have found that a scyllo-inositol/boric acid complex consisting of scyllo-inositol, boric acid, and a metal ion has a specific association and is a complex having low solubility which is different from other complexes of neutral sugars. Furthermore, the inventors have found that the scyllo-inositol/boric acid complex is effectively formed and precipitated by: adding boric acid and a metal salt in amounts twice moles or more, preferably twice to three times more than that of scyllo-inositol dissolved in a liquid mixture; and maintaining the solution in an alkaline condition of pH 8.0 to 11.0, preferably pH 9.0 to 10.0. Under such conditions, the scyllo-inositol/boric acid complex was formed from a liquid mixture containing scyllo-inositol and neutral sugars such as myo-inositol. Then, the complex was dissolved in an acid, followed by purification using an ion exchange resin or water-soluble organic solvent, and thereby scyllo-inositol is efficiently produced.

Thus, the present invention has been completed.

That is, the present invention provides the followings.

(1) A method of producing scyllo-inositol comprising:

allowing a microorganism capable of converting myo-inositol into scyllo-inositol and belonging to the genus *Acetobacter* or *Burkholderia* to react with myo-inositol in a solution containing myo-inositol to produce and accumulate scyllo-inositol in the solution; and collecting the scyllo-inositol from the solution.

(2) The method according to(1), wherein the solution containing myo-inositol is a liquid medium containing myo-inositol, and the microorganism is allowed to react with myo-inositol by culturing the microorganism in the liquid medium.

(3) The method according to (1), wherein cells obtained by culturing the microorganism is allowed to react with myo-inositol in the solution.

(4) The method according to any one of (1) to (3), wherein the microorganism is a microorganism belonging to *Acetobacter cerevisiae, Acetobacter malorum*, or *Burkholderia andropogonis*.

(5) The method according to any one of (1) to (3), wherein the microorganism is *Acetobacter* sp. AB10281 strain (FERM BP-10119) or a mutant strain thereof.

(6) *Acetobacter* sp. AB10281 strain (FERM BP-10119) or a mutant strain thereof having an ability to convert myo-inositol into scyllo-inositol.

(7) NAD$^+$-independent myo-inositol 2-dehydrogenase having at least the following physiological properties:
(a) Action: catalyzing a reaction that deprives myo-inositol of electron to produce scyllo-inosose in the presence of an electron accepting substance
(b) Optimum pH: the activity is maximum at pH of 4.5 to 5.5
(c) Cofactor: containing 1 mol of heme iron per 1 mol of the enzyme
(d) Inhibitor: the activity of the enzyme is inhibited to 1% or lower by 1 mM of Sn$^{2+}$ ion
(e) Subunit structure: a heteromer at least comprising proteins each having a molecular weight of 76 k Dalton or 46 k Dalton
(g) Substrate specificity: acting on D-chiro-inositol, muco-inositol, and myo-inositol to convert them into D-chiro-1-inosose, L-chiro-2-inosose, and scyllo-inosose, respectively, but not acting on allo-inositol, scyllo-inositol, L-chiro-inositol, and glucose (8) A method for producing myo-inositol 2-dehydrogenase, comprising:
culturing a microorganism which has an ability to produce NAD$^+$-independent myo-inositol 2-dehydrogenase and belongs to the genus *Acetobacter*; and
separating and purifying the myo-inositol 2-dehydrogenase from the cells of the cultured microorganism.

(9) The method according to (8), wherein the microorganism is *Acetobacter* sp. AB10253 strain (FERM BP-10136).

(10) A method for producing scyllo-inosose, comprising:
generating scyllo-inosose by allowing NAD$^+$-independent myo-inositol 2-dehydrogenase to react with myo-inositol in a solution containing myo-inositol and an electron acceptor; and
separating and purifying the generated scyllo-inosose from the solution.

(11) A method for producing scyllo-inositol, comprising:
generating scyllo-inosose by allowing NAD$^+$-independent myo-inositol 2-dehydrogenase to react with myo-inositol in a solution containing myo-inositol and an electron acceptor;
generating scyllo-inositol by allowing the scyllo-inosose to react with a reducing agent; and
separating and purifying the scyllo-inositol.

(12) A method for screening a microorganism for producing scyllo-inosose, comprising:
subjecting *Acetobacter* sp. AB10253 strain (FERM BP-10136) to a mutagenesis treatment to obtain mutant strains; and
selecting a strain from the mutant strains based on NAD$^+$-independent myo-inositol 2-dehydrogenase activity.

(13) A method for screening a microorganism for producing scyllo-inosose, comprising:
isolating microorganisms from a natural sample containing the microorganisms;
selecting a microorganism from the isolated microorganisms based on NAD$^+$-independent myo-inositol 2-dehydrogenase activity.

(14) A method for producing scyllo-inosose, comprising:
generating scyllo-inosose from myo-inositol by culturing the microorganism for producing scyllo-inosose obtained by the screening method according to (12) or (13) in a medium containing myo-inositol; and
separating and isolating the generated scyllo-inosose from the medium.

(15) A method for producing scyllo-inositol, comprising:
generating scyllo-inosose from myo-inositol by culturing the microorganism for producing scyllo-inosose obtained by the screening method according to (12) or (13) in a medium containing myo-inositol;
generating scyllo-inositol by allowing the scyllo-inosose to react with a reducing agent; and
separating and isolating the generated scyllo-inositol from the medium.

(16) A scyllo-inositol dehydrogenase having the following physiological properties:
Reaction: as shown in the following formula, catalyzing an oxidation-reduction reaction between scyllo-inositol and scyllo-inosose and stereospecifically reducing scyllo-inosose to scyllo-inositol in the presence of NADH or NADPH

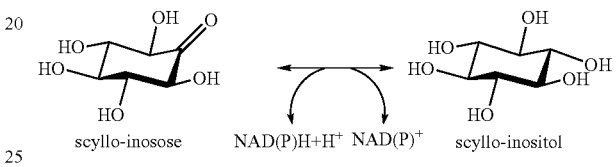

(17) The scyllo-inositol dehydrogenase according to (16), further having the following physiological properties:
(1) Molecular weight and association property: 38 to 46 k Dalton, forming a dimer or a trimer
(2) Coenzyme: requiring NAD$^+$ or NADP$^+$, or NADH or NADPH as a coenzyme
(3) Activating heavy metals: activated in the presence of Co$^{2+}$ ion
(4) Inhibiting heavy metals: inhibited in the presence of Sn$^{2+}$ ion
(5) Optimum pH: having an activity at pH of 5 to 9

(18) A protein represented by the following (A) or (B):
(A) A protein comprising an amino acid sequence of SEQ ID NO: 28, or
(B) A protein comprising an amino acid sequence of SEQ ID NO: 28, whereby one or plural of amino acids are substituted, deleted, inserted, and/or added, and catalyzing the oxidation-reduction reaction between scyllo-inositol and scyllo-inosose and stereospecifically reducing scyllo-inosose into scyllo-inositol in the presence of NADH or NADPH.

(19) A DNA encoding a protein represented by the following (A) or (B):
(A) A protein comprising an amino acid sequence of SEQ ID NO: 28, or
(B) A protein comprising an amino acid sequence of SEQ ID NO: 28, whereby one or plural of amino acids are substituted, deleted, inserted, and/or added, and catalyzing the oxidation-reduction reaction between scyllo-inositol and scyllo-inosose and stereospecifically reducing scyllo-inosose into scyllo-inositol in the presence of NADH or NADPH.

(20) A DNA represented by the following (a) or (b):
(a) A DNA comprising a coding region of the nucleotide sequence of SEQ ID NO: 27, or
(b) A DNA which hybridizes under stringent conditions with a DNA having the nucleotide sequence of SEQ ID NO: 27 or a nucleotide sequence complementary thereto, and encodes a protein that catalyzes the oxidation-reduction reaction between scyllo-inositol and scyllo-inosose and stereospecifically reduces scyllo-inosose into scyllo-inositol.

(21) A vector comprising the DNA according to (19) or (20).

(22) A transformant microorganism comprising the DNA according to (19) or (20) or the vector according to (21).

(23) The transformant microorganism according to (22), wherein a host to be transformed is *Escherichia coli*.

(24) A method for producing scyllo-inositol dehydrogenase, comprising:
culturing the transformant microorganism according to (22) or (23); and
collecting scyllo-inositol dehydrogenase from the culture product thereof.

(25) A method for producing scyllo-inositol dehydrogenase, comprising: subjecting myo-inositol as a substrate to an oxidation conversion reaction into scyllo-inositol at pH 6.0 to 8.5 in the presence of $NAD^+$ or $NADP^+$, in a solution which contains the scyllo-inositol dehydrogenase according to (16) and myo-inositol dehydrogenase (EC 1.1.1.18) which catalyzes a reaction of oxidizing myo-inositol to generate scyllo-inosose in the presence of $NAD^+$ or $NADP^+$.

(26) The method according to (25), wherein scyllo-inositol is added at 0.01 to 3% into the solution.

(27) The method according to (25), wherein scyllo-inositol is added at 0.2 to 0.5% into the solution.

(28) The method according to (25), wherein cobalt salt and/or magnesium salt is added at 0.01 to 5.0 mM into the solution.

(29) The method according to (25), wherein cobalt salt and/or magnesium salt is added at 0.2 to 2.0 mM into the solution.

(30) The method according to (25), wherein the concentration of myo-inositol in the solution is adjusted to 5 to 22%; and wherein the scyllo-inositol which is generated by the enzymatic reaction is crystalyzed in the reaction solution, and is separated as a crystal from the reaction system by filtration.

(31) The method according to (25), wherein the scyllo-inositol dehydrogenase is a protein represented by the following (A) or (B):
(A) A protein comprising an amino acid sequence of SEQ ID NO: 28, or
(B) A protein comprising an amino acid sequence of SEQ ID NO: 28, whereby one or plural of amino acids are substituted, deleted, inserted, and/or an added, and catalyzing the oxidation-reduction reaction between scyllo-inositol and scyllo-inosose and stereospecifically reducing scyllo-inosose into scyllo-inositol in the presence of NADH or NADPH.

(32) The method according to (25), wherein the scyllo-inositol dehydrogenase is a protein encoded by the DNA represented by the following (a) or (b):
(a) A DNA comprising a coding region of the nucleotide sequence of SEQ ID NO: 27, or
(b) A DNA which hybridizes under stringent conditions with a DNA having a nucleotide sequence of SEQ ID NO: 27 or a nucleotide sequence complementary thereto, and encodes a protein which catalyzes the oxidation-reduction reaction between scyllo-inositol and scyllo-inosose and stereospecifically reduces scyllo-inosose into scyllo-inositol.

(33) The method according to (25), wherein the scyllo-inositol dehydrogenase is a protein represented by the following (C) or (D):
(C) A protein comprising an amino acid sequence of SEQ ID NO: 2, 4, 6, 8, 10, 12, or 14, or
(D) A protein comprising an amino acid sequence of SEQ ID NO: 2, 4, 6, 8, 10, 12, or 14, whereby one or plural of amino acids are substituted, deleted, inserted, and/or added, and catalyzing the oxidation-reduction reaction between scyllo-inositol and scyllo-inosose and stereospecifically reducing scyllo-inosose into scyllo-inositol in the presence of NADH or NADPH.

(34) The method according to (25), wherein the scyllo-inositol dehydrogenase is a protein encoded by the DNA represented by the following (c) or (d):
(c) A DNA comprising a coding region of the nucleotide sequence of SEQ ID NO: 1, 3, 5, 7, 9, 11, or 13, or
(d) A DNA which hybridizes under stringent conditions with a DNA having the nucleotide sequence of SEQ ID NO: 1, 3, 5, 7, 9, 11, or 13 or a nucleotide sequence complementary thereto, and encodes a protein which catalyzes the oxidation-reduction reaction between scyllo-inositol and scyllo-inosose and stereospecifically reduces scyllo-inosose into scyllo-inositol.

(35) A method for producing a purified scyllo-inositol, comprising:
a first step of forming a scyllo-inositol/boric acid complex by adding boric acid and a metal salt into a liquid mixture containing scyllo-inositol and neutral sugar other than scyllo-inositol in an amount two times or more larger than that of scyllo-inositol dissolved in the liquid mixture, and by adjusting the pH of the liquid mixture to 8.0 to 11.0;
a second step of separating the complex from the liquid mixture;
a third step of dissolving the separated complex into acid to cleave into scyllo-inositol and boric acid; and
a fourth step of isolating and purifying the scyllo-inositol from the acidic solution or acidic suspension obtained from the third step.

(36) The method according to (35), wherein, in the first step, the amounts of the boric acid and metal salt to be added is not less than twice mol, and not more than three times of the scyllo-inositol dissolved in the liquid mixture.

(37) The method according to (35), wherein, in the first step, pH of the liquid mixture is adjusted to 9.0 to 10.0.

(38) The method according to (35), wherein the metal salt to be added is one or more kinds of metal salts selected from the group consisting of $NaCl$, $NaHCO_3$, $Na_2CO_3$, $Na_2SO_4$, $NaHSO_4$, $NaH_2PO_4$, $Na_2HPO_4$, $Na_3PO_4$, borax, $KCl$, $KHCO_3$, $K_2CO_3$, $K_2SO_4$, $KHSO_4$, $KH_2PO_4$, $K_2HPO_4$, $K_3PO_4$, $MgCl_2$, $MgCO_3$, and $MgSO_4$.

(39) The method according to (35), wherein the liquid mixture containing the scyllo-inositol and the neutral sugar other than scyllo-inositol is a liquid mixture containing myo-inositol and scyllo-inositol obtained by reducing scyllo-inosose in a solution containing scyllo-inosose.

(40) The method according to (35), wherein, in the third step, the solution obtained by dissolving the complex in acid is adjusted to an acidic solution of 0.1 N or higher; and, in the fourth step, the acidic solution is contacted with an strong acidic ion exchange resin, and with a strong basic ion exchange resin or a boric acid-selective adsorbing resin, and then scyllo-inositol is precipitated from the acidic solution.

(41) The method according to (35), wherein, in the fourth step, scyllo-inositol is precipitated by adding an aqueous organic solvent to the acidic solution or acidic suspension.

(42) The method according to (41), wherein the aqueous organic solvent is ethanol or methanol; and the ethanol is added in a volume 0.3 to 3 times larger, or the methanol is added in a volume 0.3 to 5 times larger, than that of the acidic solution or acidic suspension.

(43) The method according to (41), wherein the aqueous organic solvent is ethanol or methanol; and the ethanol is added in a volume 0.6 to 1.5 times larger, or the methanol is added in a volume 0.9 to 2 times larger, than that of the acidic solution or the acidic suspension.

(44) A method of producing scyllo-inositol, comprising:
a first step of obtaining a liquid mixture containing myo-inositol and scyllo-inositol by reducing scyllo-inosose using a metal salt of boron hydride in a solution containing scyllo-inosose;
a second step of dissolving a scyllo-inositol/boric acid complex in the liquid mixture by adding an acid to the liquid mixture and adjusting the solution to be an acidic solution of 0.01 N or more; and
a third step of precipitating only scyllo-inositol by adding an aqueous organic solvent to the acidic solution in an amount such that the myo-inositol is not precipitated.

(45) The method according to (44), wherein, in the third step, the aqueous organic solvent to be added is ethanol, methanol, or 1-propanol; and the ethanol is added in a volume 0.2 to 0.4 times larger, the methanol is added in a volume 0.2 to 0.8 times larger, or the 1-propanol is added in a volume 0.2 to 0.4 times larger, than that of the acidic solution.

(46) The method according to (44), wherein, in the third step, the aqueous organic solvent to be added is ethanol, methanol, or 1-propanol; and the ethanol is added in a volume 0.35 to 0.45 times larger, the methanol is added in a volume 0.45 to 0.55 times larger, or the 1-propanol is added in a volume 0.35 to 0.45 times larger, than that of the acidic solution.

DESCRIPTION OF THE PREFERRED EMBODIMENTS

Figure 1:
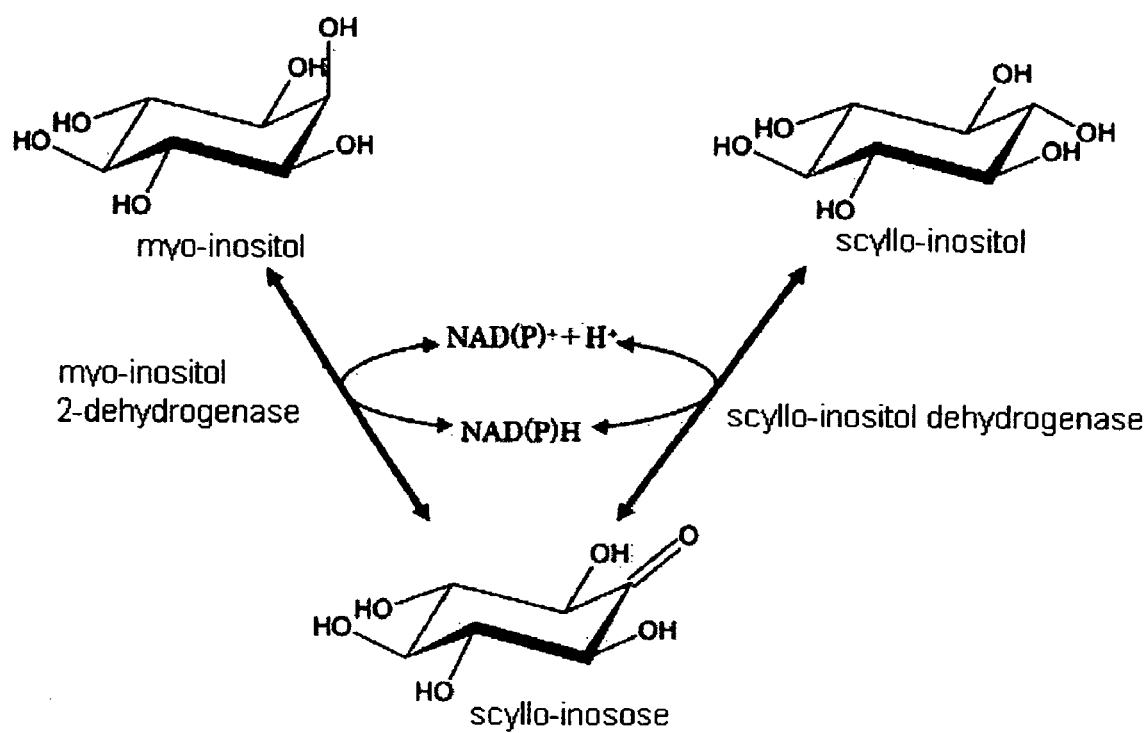
FIG. 1 shows a schematic view of the principle of the production of scyllo-inositol by combination of enzymes.

1. Method of Producing Scyllo-inositol Using a Microorganism Belonging to the genus *Acetobacter* or the Genus *Burkholderia*

One embodiment of the present invention relates to a method of producing scyllo-inositol comprising producing and accumulating scyllo-inositol in a solution containing myo-inositol by reacting the myo-inositol with a microorganism which belongs to the genus *Acetobacter* or the genus *Burkholderia* and has an ability to convert myo-inositol into scyllo-inositol; and collecting the scyllo-inositol from the solution.

The microorganism to be used in the producing method of the present invention is a microorganism which belongs to the genus *Acetobacter* or the genus *Burkholderia* and has an ability to convert myo-inositol into scyllo-inositol. Here, examples of the microorganism belonging to the genus *Acetobacter* include *Acetobacter cerevisiae*, *Acetobacter malorum*, *Acetobacter orleanensis*, *Acetobacter indonesiensis*, *Acetobacter orientalis*, *Acetobacter aceti*, *Acetobacter liquefaciens*, *Acetobacter pasteurianus*, *Acetobacter hansenii*, and unidentified strains (sp.) thereof Examples of the microorganism belonging to the genus *Burkholderia* include *Burkholderia andropogonis*, *Burkholderia caryophylli*, and *Burkholderia graminis*. Of those, *Acetobacter cerevisiae*, *Acetobacter malorum*, and *Burkholderia andropogonis* are particularly preferable. The phrase "an ability to convert myo-inositol into scyllo-inositol" refers to, for example, an ability of a microorganism to accumulate scyllo-inositol in a medium when the microorganism is cultured in a medium containing myo-inositol.

A specific example of the microorganism includes *Acetobacter* sp. AB10281 strain. The strain is a strain obtained by mutating *Acetobacter* sp. AB10253 strain (FERM BP-10136) to impart an ability to convert myo-inositol into scyllo-inositol. The strain has been deposited in International Patent Organism Depositary, the National Institute of Advanced Industrial Science and Technology (postal code: 305-8566, Tsukuba Central 6, 1-1, Higashi 1-chome, Tsukuba, Ibaraki, Japan) with an accession number of FERM P-19639 on Jan. 20, 2004, and is then converted to the international deposition under the Budapest Treaty and given an accession number of FERM BP-10119.

The *Acetobacter* sp. AB10253 strain has been deposited in International Patent Organism Depositary, the National Institute of Advanced Industrial Science and Technology with an accession number of FERM P-18868 on May 24, 2002, and then converted to the international deposition under the Budapest Treaty and deposited with an accession number of FERM BP-10136.

Derivative strains of a microorganism belonging to the genus *Acetobacter* such as *Acetobacter* sp. AB10281 strain or *Acetobacter* sp. AB10253 strain can also be used. Such derivative strains can be obtained by mutating the microorganism and selecting a strain having a property to selectively and directly convert myo-inositol into scyllo-inositol among the strains into which mutation had been introduced. Examples of a mutation method include a physical mutation method such as UV irradiation or radiation irradiation, as well as a chemical mutation method which employs mutating agents including N-nitrosoguanidine, ethyl methane sulfonate, nitrite, methyl methane sulfonate, an acridine dye, benzopyrene, dimethyl sulfate, and the like.

An example of a method of reacting the above-described microorganism with myo-inositol in a solution containing the myo-inositol includes a method of culturing the microorganism of the present invention in a liquid medium containing myo-inositol.

In this case, the composition of the liquid medium to be used is not particularly limited as long as the object of the present invention is achieved. A liquid medium may be any medium which contains myo-inositol as a material to be converted into scyllo-inositol, in addition to carbon sources, nitrogen sources, organic nutrients, inorganic salts, and the like. Both a synthetic medium and a natural medium can be used. The liquid medium is added with 0.1% to 40%, more preferably 10% to 30% of myo-inositol, and is preferably added with: 0.1% to 20%, more preferably 0.3% to 5% of glycerol, sucrose, maltose, or a starch as a carbon source; and 0.01% to 5.0%, preferably 0.5% to 2.0% of a yeast extract, peptone, casamino acid, ammonium sulfate, ammonium chloride, ammonium nitrate, urea, or the like as a nitrogen source. In addition, if necessary, inorganic salts each capable of forming an ion of sodium, potassium, calcium, magnesium, cobalt, manganese, zinc, iron, copper, molybdenum, phosphoric acid, sulfuric acid, or the like can be added to the medium. A hydrogen-ion concentration in the culture solution does not particularly need to be controlled. However, scyllo-inositol is efficiently produced by culturing at conditions adjusted to preferably pH of 4 to 10, more preferably 5 to 9.

Culture conditions vary depending on a kind of the medium. However, a culture temperature is 12 to 35° C., preferably 20 to 27° C. A culture may be performed aerobically by, for example, shaking the liquid medium or aerating air or an oxygen gas into the liquid medium. During a main culture, myo-inositol is oxidized at an early stage of the culture to generate scyllo-inosose and then the scyllo-inosose is reduced in a living body at a later stage, to thereby generate scyllo-inositol. A further culture results in gradual decomposition of the scyllo-inositol. Therefore, a culture period may be until when the accumulation of the scyllo-inositol becomes the maximum or required amount, and is generally 1 to 10 days, preferably 3 to 8 days.

Alternatively, cells of a microorganism obtained by culture may be reacted with myo-inositol in a solution containing myo-inositol. Here, for cells obtained by culture, cells obtained from a microorganism cultured under other appropriate culture conditions may be used, or cells separated and collected from the culture broth of a microorganism used for the production of scyllo-inositol may be reused. The collection of the cells to obtain the cells may be performed by a known method such as centrifugal separation or filtration.

By reacting the microorganism with myo-inositol as described above, scyllo-inositol accumulates in the solution. A general method of isolating and purifying a normal aqueous neutral substance can be applied for the method of collecting scyllo-inositol from the culture solution. That is, supernatants of the culture solution are treated with activated carbon, an ion exchange resin, or the like after cells had been removed from the culture solution, to thereby allow most impurities other than scyllo-inositol to be removed. After that, a substance of interest can be isolated by using such a method as recrystallization.

More specifically, a culture supernatant in which scyllo-inositol is accumulated is passed through a column filled with a strong acid cation exchange resin such as Duolite® C-20 ($H^+$ type) to remove undesirable components. Flow-through solution is collected, and then deionized water is passed through the column to wash the column, to thereby collect a wash solution. The flow-through solution and the wash solution are combined together. Then, thus obtained solution is passed through a column filled with a strong base anion exchange resin such as Duolite® A116 ($OH^-$ type). Flow-through solution is collected, and then deionized water is passed through the column to wash the column, to thereby collect a wash solution. The flow-through solution and wash solution are combined together, to obtain an aqueous solution containing scyllo-inositol but almost no other impurities. The aqueous solution was concentrated to thereby obtain a concentrated solution of scyllo-inositol. The concentrated solution was then added with an appropriate amount of ethanol and left overnight at room temperature or a low temperature, to thereby allow a pure scyllo-inositol crystal to be crystallized. Meanwhile, based on a low water-solubility of scyllo-inositol, a pure scyllo-inositol crystal can be crystallized just by concentrating and filtrating the aqueous solution. Further, a column filled with activated carbon can be used for decolorization, during the column operation.

A pure scyllo-inositol crystal can be obtained by other purification method, such as described later, comprising: preparing a scyllo-inositol/boric acid complex by adding boric acid and NaCl to the solution containing scyllo-inositol obtained by culture; filtrating and separating the scyllo-inositol/boric acid complex; allowing boric acid to be released by adding an acid; and crystallizing scyllo-inositol by adding an organic solvent such as methanol.

Furthermore, during the culture of the strain of the present invention, scyllo-inositol having a low water-solubility (solubility of about 1.6%) at normal temperature crystallizes and precipitates. Therefore, myo-inositol can be additionally added during the culture to further accumulate the scyllo-inositol as crystals.

2. Novel $NAD^+$-independent Myo-inositol 2-dehydrogenase, and a Method of Producing Scyllo-inosose and Scyllo-inositol Using the Enzyme Other embodiment of the present invention relates to a novel $NAD^+$-independent myo-inositol 2-dehydrogenase, and a method of producing scyllo-inosose and scyllo-inositol using the enzyme.

<2-1> Novel $NAD^+$-independent Myo-inositol 2-dehydrogenase $NAD^+$-independent myo-inositol 2-dehydrogenase of the present invention has at least the following physiological properties.

(a) Action: catalyzing a reaction that deprives an electron from myo-inositol to generate scyllo-inosose in the presence of an electron accepting substance;

(b) Optimum pH: its activity is maximum at pH of 4.5 to 5.5;

(c) Cofactor: requiring 1 mol of hemoferrum per 1 mol of the enzyme;

(d) Inhibitor: its enzymatic activity is inhibited to 1% or lower by 1 mM of $Sn^{2+}$ ion;

(e) Subunit structure: a heteromer at least comprising proteins each having a molecular weight of 76 k Dalton and 46 k Dalton;

(g) Substrate specificity: reactive to D-chiro-inositol, muco-inositol, and myo-inositol, and converts them into D-chiro-1-inosose, L-chiro-2-inosose, and scyllo-inosose, respectively, and not reactive to allo-inositol, scyllo-inositol, L-chiro-inositol, and glucose.

The action (a) can be confirmed by determining the myo-inositol 2-dehydrogenase activity in the presence of an electron accepting substance. Examples of the electron accepting substance as used herein include oxidized DCIP, phenazine methosulfate (PMS), methylene blue, and $Fe^{3+}$ ion. Those can be used in combination, however, oxidized DCIP is preferably used. The myo-inositol 2-dehydrogenase activity can be measured defining as 1 unit the activity at which 1 µmol of myo-inositol is oxidized per 1 minute when a reaction rate is calculated based on a change in absorption at 600 nm in a 1 mL solution containing 100 mM phosphate buffer (pH 5.0), 5 mg of myo-inositol, and 0.4 mg of 2,4-dichloroindophenol (oxidized DCIP). The optimum pH (b) can be confirmed by: measuring the activity of myo-inositol 2-dehydrogenase at different pH; and determining the range of pH where the enzymatic activity shows the maximum value. Meanwhile, the property shown in (d) can be confirmed by comparing the enzymatic activity under which $Sn^{2+}$ ion is added to an enzymatic activity determining system, with the activity under which no $Sn^{2+}$ ion is added thereto. Further, the subunit structure (e) can be confirmed by SDS-PAGE (sodium dodecyl sulfate-polyacrylamide gel electrophoresis) or the like. The molecular weights of 76 k Dalton and 46 k Dalton of respective subunits are approximate values, and may be around 76 k Dalton and 46 k Dalton.

An example of the $NAD^+$-independent myo-inositol 2-dehydrogenase of the present invention includes one derived from *Acetobacter* sp. AB10253 strain, but not limited to this one as long as it has the above-described properties. The substrate specificity of the $NAD^+$-independent myo-inositol 2-dehydrogenase of the present invention is as described above. The specific activity and Km value of the enzyme derived from *Acetobacter* sp. AB10253 strain at a substrate concentration of 50 mM are represented as follows. That is, D-chiro-inositol (specific activity of 100%, Km=8.8 mM), muco-inositol (specific activity of 68%, Km=14.5 mM), and myo-inositol (specific activity of 53%, Km=20 mM).

The NAD+-independent myo-inositol 2-dehydrogenase of the present invention is a NAD+-independent myo-inositol 2-dehydrogenase which is a type different from a conventionally known NAD+-dependent myo-inositol 2-dehydrogenase. The following Table 1 shows the comparison of particular differences between both enzymes.

TABLE 1

|  | Enzyme of the present invention (NAD+-independent type) | Conventional enzyme (NAD+-dependent type) |
|---|---|---|
| Intracellular localization | Membrane fraction | Cytoplasmic soluble fraction |
| Optimum pH | pH 4.5-5.5 | pH 8.0-9.0 |
| Electron acceptor | Hemoferrum | NAD+ |

<2-2> Method of Producing NAD+-independent Myo-inositol 2-dehydrogenase

A method of producing the NAD+-independent myo-inositol 2-dehydrogenase of the present invention is a producing method comprising culturing a microorganism which is capable of producing the NAD+-independent myo-inositol 2-dehydrogenase and belongs to the genus *Acetobacter*, and separating and purifying myo-inositol 2-dehydrogenase from the cultured cells of the microorganism.

An example of the microorganism which can be used for production of the NAD+-independent myo-inositol 2-dehydrogenase includes *Acetobacter* sp. AB10253 (FERM BP-10136), but not limited to this one as long as it is capable of producing the NAD+-independent myo-inositol 2-dehydrogenase. A conventionally known medium which is used for general culture of a microorganism and contains a carbon source, a nitrogen source, other nutrients, and the like can be used as a medium for culturing the microorganism. Here, examples of the carbon source include glucose, sucrose, maltose, and a starch. Preferably, the concentration of the carbon source to be added is 0.1% to 20%, more preferably 0.3% to 5%. Examples of the nitrogen source include peptone, yeast extract, casamino acid, ammonium sulfate, ammonium chloride, ammonium nitrate, urea, and meat extract. Preferably, the concentration of the nitrogen source to be added is 0.01% to 5.0%, preferably 0.5% to 2.0%. In addition, if necessary, inorganic salts each capable of generating an ion of sodium, potassium, calcium, magnesium, cobalt, manganese, zinc, iron, copper, molybdenum, phosphoric acid, sulfuric acid, or the like are preferably added to the medium. The expression of the enzyme of the present invention is efficiently induced by culturing it in a culture solution adjusted to pH of 3 to 10, preferably pH of 5 to 7. The value shown by "%" indicates a percentage of w/v, and a concentration shown by "%" also indicates the same meaning hereinafter.

In order to induce the expression of NAD+-independent myo-inositol 2-dehydrogenase, a medium containing myo-inositol is preferably used. In this case, myo-inositol is appropriately added at a concentration of 0.2% to 15%, preferably 1% to 5%, more preferably 3%.

Culture conditions vary depending on a kind of the medium. However, a culture temperature is preferably 12 to 35° C., more preferably 20 to 27° C. Culture is preferably performed aerobically by, for example, shaking the liquid medium or aerating air or an oxygen gas into the liquid medium. A culture period may be preferably up to the day on which the myo-inositol completely is eliminated from the culture solution and the accumulation of the scyllo-inositol becomes the maximum, and is generally 1 to 10 days, preferably 3 to 8 days.

The enzyme of the present invention can be obtained by separating and purifying the enzyme from the cultured cells. The separation and purification of the enzyme can be performed similarly as a conventional purification method of a protein. Specific examples of the separation and purification method is described hereinafter, however, the method is not limited to these.

First, cells obtained from the culture are precipitated or concentrated by means of centrifugal separation, filtration, or the like. Next, the obtained precipitate or suspension of the cells is disrupted. French press, dynamill, ultrasonication, or the like can be used for the disruption, however, ultrasonication is preferable. For example, cells collected from 1 L of a culture solution are washed with water and are finally suspended into 50 ml of water. The suspension is subjected to ultrasonic to disrupt the cells and then subjected to centrifugal separation at 12,000 rpm to thereby obtain a precipitate. Subsequently, the obtained precipitate is suspended in an appropriate buffer such as Tris buffer or phosphate solution (concentration of 2 mM to 100 mM, pH of 6.0 to 8.0). Then, a surfactant is added thereto, to thereby allow a membrane enzyme to be extracted. Examples of the surfactant include Triton X-100®, Tween 20®, and Tween 80®. Each of the surfactants can be used at a concentration of 0.02% to 1.0%, however, it is preferable to use Triton X-100 at a concentration of 0.6%.

The enzyme can be extracted by incubating the suspension obtained above into which a surfactant is added, at a low temperature for about 1 to 5 hours. Then, the suspension is again subjected to centrifugal separation, to thereby obtain an enzyme solubilized in a supernatant. Thus obtained enzyme solution can be used for the production of scyllo-inositol as it is, or if necessary, the enzyme can be concentrated by a method to be used for general enzyme concentration. Examples of the method of concentrating an enzyme include ammonium sulfate fractionation and ultrafiltration. Also, the following treatment is preferably performed in order to purify the enzyme with higher purity.

The solubilized enzyme is preferably subjected to column chromatography purification. An example of the column chromatography includes DEAE column chromatography. Any DEAE column containing a DEAE group can be used even if it has different carrier characteristics. A preferable example of the DEAE column includes a DEAE Toyopearl (manufactured by Tosoh Corporation). In the case of purifying the enzyme using a DEAE Toyopearl, the enzyme solution may be adjusted to have a salt concentration of 20 mM before being added to the column. Next, the protein that had been adsorbed to the column in such a manner is eluted by passing a solution of 20 mM buffer (pH of 6.0 to 8.0) with no surfactant and with linear concentration gradient of NaCl or KCl. A concentration gradient of 0 mM to 500 mM is used for NaCl and a concentration gradient of 0 mM to 350 mM is used for KCl. Next, 20 mM buffer (pH of 6.0 to 8.0) with no surfactant is again passed through the column to wash the column, then solution of 20 mM buffer (pH of 6.0 to 8.0) with a surfactant and with linear concentration gradient of NaCl or KCl is passed through the column, to thereby elute the protein. A concentration gradient of 0 mM to 500 mM is used for NaCl and a concentration gradient of 0 mM to 350 mM is used for KCl. Examples of the surfactant to be added include Triton X-100, Tween 20, and Tween 80. Each of the surfactants can be used at a concentration of 0.02% to 1.0%, however it is preferable to use Triton X-100 at a concentration of 0.1%. Under such conditions, the enzyme of the present invention is eluted from the column by means of the 20 mM buffer containing a surfactant and 100 to 170 mM of NaCl.

Thus obtained enzyme solution can be used for the production of scyllo-inositol as it is, or the enzyme solution is further treated for higher purification.

In the case of purification based on the enzymatic activity, the enzymatic activity can be measured, for example, by calculating a reaction rate based on the change in absorption at 600 nm in 1 mL solution containing 100 mM phosphate buffer (pH 5.0), 5 mg of myo-inositol, and 0.4 mg of 2,4-dichloroindophenol (oxidized DCIP), and defining the activity to oxidize 1 μmol of myo-inositol per 1 minute as 1 unit.

In the case of further purification of the enzyme of the present invention, the enzyme solution of the present invention is preferably added to, for example, a hydroxyapatite column after being desalted by dialysis or ultrafiltration. In this case, the protein that had been adsorbed to the hydroxyapatite column is eluted by passing through a phosphate buffer (pH 7.0) with a liner concentration gradient. The concentration gradient of the phosphate buffer to be used is 0 mM to 500 mM. Examples of the surfactant include Triton X-100, Tween 20, and Tween 80. Each of the surfactants can be used at a concentration of 0.02% to 1.0%, however, it is preferable to use Triton X-100 at a concentration of 0.1%. Under such conditions, the enzyme of the present invention is eluted from the column by means of 210 to 260 mM phosphate buffer containing a surfactant. Thus obtained enzyme solution contains almost pure $NAD^+$-independent myo-inositol 2-dehydrogenase, and therefore, it can be used for the production of scyllo-inositol as it is.

<2-3> Method of Screening a Microorganism for Producing Scyllo-inosose

The present invention also relates to a method of screening a microorganism for producing scyllo-inosose, comprising mutating and treating the *Acetobacter* sp. AB10253 strain; and selecting a microorganism among the obtained mutant strains based on $NAD^+$-independent myo-inositol 2-dehydrogenase activity.

The $NAD^+$-independent myo-inositol 2-dehydrogenase activity can be determined by, for example, adding a membrane fraction which is obtained from the cells of the microorganism to 1 mL solution containing 100 mM phosphate buffer (pH 5.0), 5 mg of myo-inositol, and 0.4 mg of 2,4-dichloroindophenol (oxidized DCIP), and determining the change in absorption at 600 nm of the resultant. For example, as a criteria of selection, a strain that exhibits $NAD^+$-independent myo-inositol 2-dehydrogenase activity 1.2 times or more, preferably twice or more than that of a non-mutant AB10253 strain is preferably selected, when the activity is determined by means of the above-described method and compared.

For the method of mutating the *Acetobacter* sp. AB10253 strain, a general mutating method for a microorganism can be used. Examples of the method include a physical mutation method such as UV irradiation or radiation irradiation, as well as a chemical mutation method which utilizes a mutation agent such as N-nitrosoguanidine, ethyl methane sulfonate, nitrite, methyl methane sulfonate, an acridine dye, benzopyrene, and dimethyl sulfate.

The method of screening a microorganism for producing scyllo-inosose from the *Acetobacter* sp. which has been subjected to the mutation treatment is exemplified hereinafter. However, the screening method is not limited to the following method as long as the screening method is performed based on the $NAD^+$-independent myo-inositol 2-dehydrogenase activity.

The AB10253 strain which has been subjected to a mutating treatment is spread on a agar medium containing myo-inositol and nutrients such that 10 to 300 colonies, preferably 100 to 150 colonies are formed per a dish having a diameter of 9 cm. Here, a carbon source, a nitrogen source, and other nutrients to be added as nutrients to the medium, which are known to be conventionally used for general microorganism culture, can be used. Examples of the carbon source include glucose, sucrose, maltose, and a starch. Preferably, the concentration of the carbon source to be added is 0.1% to 20%,. more preferably 0.3% to 5%. Examples of the nitrogen source include peptone, a yeast extract, casamino acid, ammonium sulfate, ammonium chloride, ammonium nitrate, urea, and meat extract. Preferably, the concentration of the nitrogen source to be added is 0.01% to 5.0%, preferably 0.5% to 2.0%.

In addition, if necessary, inorganic salts each capable of forming an ion of sodium, potassium, calcium, magnesium, cobalt, manganese, zinc, iron, copper, molybdenum, phosphoric acid, sulfuric acid, or the like are suitably added to the medium. The expression of the enzyme of the present invention is efficiently induced by culturing in the culture solution adjusted to pH of 3 to 10, preferably pH of 5 to 7.

The culture may be performed until adequate numbers of colony are formed, and colonies are formed in about 3 days. The culture temperature is preferably 25 to 30° C., preferably 27° C., which is the optimum temperature for the growth of the microorganism.

Colonies are isolated and cultured and the $NAD^+$-independent myo-inositol 2-dehydrogenase activity of each colony is determined, to allow selection of strains each exhibiting a strong activity. Furthermore, as described hereinafter, the strains can be efficiently selected on an agar medium using a 9 cm-dish.

After the culture, 10 ml of an agar medium for analysis is slowly poured onto the colonies formed on the 9 cm-dish. The agar medium for analysis is a viscous solution prepared by: adding an agar to be 0.5% into a composition consisting of 100 mM phosphate buffer containing 1% myo-inositol and 0.4% oxidized DCIP; cooling the mixture to 36° C. after the agar had been dissolved, so that the agar does not solidify. The agar medium for analysis as prepared above is applied is slowly cooled to 27° C., and solidified such that the agar medium is piled on the colonies which had been formed on the 9 cm-dish.

After the treatment, the dish was incubated at 27° C. As a result, blue color of the oxidized DCIP spread on the entire agar medium is observed, and then gradually changes to transparent only around the colonies, owing to the degree of the $NAD^+$-independent myo-inositol 2-dehydrogenase activity. At this time, a colony of which its surrounding changed to transparent faster than others is transferred to a fresh medium. Thus, a strain having a high $NAD^+$-independent myo-inositol 2-dehydrogenase activity can be obtained.

Meanwhile, a strain capable of converting myo-inositol into scyllo-inosose using oxygen as an electron acceptor can be bred by: further subjecting the scyllo-inosose-producing microorganism obtained as described above to a mutation treatment; and screening among the resultant strains using aerobic respiration ability as an index. Here, the term "aerobic respiration ability" means an ability to grow well under a low-oxygen condition. The term "low-oxygen condition" means a condition where the oxygen concentration is, for example, 3% or less. The *Acetobacter* sp. AB10253 strain is a strictly aerobic bacterium, therefore, a strain having high oxygen respiration ability can be obtained by transferring a colony that grows well under a low-oxygen condition into a fresh medium.

Moreover, the above-described screening method can be applied to a natural microorganism. That is, another screening method of the present invention is a screening method, comprising isolating a microorganism from a natural sample containing microorganisms; and selecting a microorganism based on the $NAD^+$-independent myo-inositol 2-dehydrogenase activity from the isolated microorganisms. Here, an example of the sample containing natural microorganisms includes soil. An example of the method of isolating a microorganism from a natural sample includes a method comprising: applying a suspension of the natural sample or a diluent thereof onto an agar medium; and allowing the microorganism in the natural sample to grow as an independent colony on the agar medium. The same operation as that of the case of using the *Acetobacter* sp. AB10253 strain can be applied to a method of screening a microorganism for the production of scyllo-inosose from the isolated microorganisms, except that the pH of the medium is adjusted to 3 to 4, preferably 3.5.

<2-4> Method of Producing Scyllo-inosose

The present invention also relates to a method of producing scyllo-inosose, comprising reacting myo-inositol with $NAD^+$-independent myo-inositol 2-dehydrogenase or a strain having a high $NAD^+$-independent myo-inositol 2-dehydrogenase activity (a microorganism for producing scyllo-inosose).

(i) Method of Producing Scyllo-inosose Using $NAD^+$-independent Myo-inositol 2-dehydrogenase The "method of producing scyllo-inosose using $NAD^+$-independent myo-inositol 2-dehydrogenase" of the present invention is a producing method comprising: producing scyllo-inosose by reacting $NAD^+$-independent myo-inositol 2-dehydrogenase with myo-inositol in a solution containing the myo-inositol and an electron acceptor; and separating and isolating the produced scyllo-inosose from the solution. Here, the $NAD^+$-independent myo-inositol 2-dehydrogenase that is obtained by the described method can be used. The degree of the purification of the enzyme of the present invention may be any degree as long as the enzyme has the activity to produce scyllo-inositol from myo-inositol.

Myo-inositol as a substrate is used at the concentration of 0.1% to 20%, preferably 5% to 10%. For the enzyme solution to be used in the reaction of the present invention, the above-described crude enzyme solution or an enzyme solution that is highly purified can be used. An alkaline solution or acidic solution can be appropriately added or an appropriate buffer solution can be used to preferably maintain the pH of the reaction to be 5.0 while monitoring the pH. A buffer having a buffering ability around pH of 5.0 can be used without particular limitation, and a phosphate buffer is preferably used.

In the producing method that utilizes the enzyme, an electron accepting substance has to be added to the reaction solution. Here, examples of the electron accepting substance include an oxidized DCIP, phenazine methosulfate (PMS), methylene blue, and $Fe^{3+}$ ion, and a combination thereof can be used, however, an oxidized DCIP is preferably used. The amount of the electron accepting substance to be added is 1 mol with respect to 1 mol of myo-inositol. The electron accepting substance can be appropriately added with respect to a corresponding mol number of myo-inositol. When the concentration of those electron accepting substances increases as the reaction proceeds, reduced electron accepting substances may precipitate. In this case, the precipitates can be removed by means of an operation such as centrifugal separation or filtration. The reaction of the present invention may be a nonuniform system according to the solubility of the electron accepting substance, and therefore the reaction is preferably carried out under stirring.

The reaction temperature of the reaction of the present invention is not limited as long as the enzyme does not lose its activity, however the reaction can be preferably carried out at a temperature of 20° C. to 40° C. The reaction time is preferably 1 to 72 hours, more preferably 8 to 12 hours. The produced scyllo-inosose can be separated and purified by a recrystallization method or the like.

(ii) Method of Producing Scyllo-inosose Using a Microorganism

The present invention also relates to a method of producing scyllo-inosose using a microorganism, comprising: producing scyllo-inosose from myo-inositol by culturing a microorganism for the production of scyllo-inosose that is obtained by the screening method on a medium containing myo-inositol; and separating and purifying the produced scyllo-inosose from the medium.

Composition of the liquid medium to be used herein is not particularly limited as long as the microorganism can produce scyllo-inosose from myo-inositol. For example, the liquid medium can contain myo-inositol as a material to be converted into scyllo-inositol, in addition to carbon sources, nitrogen sources, organic nutrients, inorganic salts, and the like. Both a synthetic medium and a natural medium can be used. Specifically, a liquid medium contains: preferably 0.1% to 40%, more preferably 10% to 30% of myo-inositol; preferably 0.1% to 20%, more preferably 0.3% to 5% of glycerol, sucrose, maltose, or a starch as a carbon source; and 0.01% to 5.0%, preferably 0.5% to 2.0% of a yeast extract, peptone, casamino acid, ammonium sulfate, ammonium chloride, ammonium nitrate, urea, or the like as a nitrogen source.

In addition, if necessary, inorganic salts each capable of forming an ion of sodium, potassium, calcium, magnesium, cobalt, manganese, zinc, iron, copper, molybdenum, phosphoric acid, sulfuric acid, or the like can be suitably added into the medium. Scyllo-inositol is efficiently produced by culturing in the culture solution adjusted to pH of 4 to 10, preferably 5 to 9.

Culture conditions vary depending on a kind of the strain or medium. However, a culture temperature is preferably 12 to 35° C., more preferably 20 to 27° C. Culture may be preferably performed aerobically by, for example, shaking the liquid medium or aerating air or an oxygen gas into the liquid medium. A culture period may be preferably until when the myo-inositol in the culture solution is completely consumed and the accumulation of the scyllo-inositol becomes the maximum, and is generally 1 to 10 days, preferably 3 to 8 days.

A general method of separating and purifying a general aqueous neutral substance can be applied for the method of separating and purifying a target substance from the culture solution. For example, a supernatant of the culture solution is treated with activated carbon, an ion exchange resin, or the like after cells had been removed from the culture solution, to thereby allow most impurities other than scyllo-inosose to be removed. However, it is preferable not to use $OH^-$ type of a strong basic anion exchange resin because it chemically changes scyllo-inosose. After that, the target substance can be separated by using a method such as recrystallization.

A specific method of separating and purifying scyllo-inosose is exemplified hereinbelow. However, the separating and purifying method is not limited thereto. First, a supernatant of the culture solution having accumulated scyllo-inosose is passed through a column filled with a strong acidic cation exchange resin such as Duolite® C-20 ($H^+$ type)(manufactured by Sumitomo Chemical Co., Ltd.) to remove undesirable components. After a flow-through solution is collected, deionized water is passed through the column to wash the column, to thereby collect a wash solution. The obtained flow-through solution and the wash solution are combined together. Thus obtained solution is passed through a column filled with a weak basic anion exchange resin such as Duolite® A368S (free base form). After a flow-through solution is collected, deionized water is passed through the column to wash the column, to thereby collect a wash solution. The obtained flow-through solution and the wash solution are combined together, to obtain a solution containing scyllo-inosose but almost no other impurities. The solution was concentrated to thereby obtain a concentrated solution of scyllo-inosose. The concentrated solution was added with an appropriate amount of ethanol and left overnight at room temperature or a low temperature, to thereby allow a pure scyllo-inosose to be crystallized.

<2-5> Method of Producing Scyllo-inositol

The present invention also relates to a method of producing scyllo-inositol, comprising: producing scyllo-inosose from myo-inositol using a $NAD^+$-independent myo-inositol 2-dehydrogenase or a strain that shows high activity of the enzyme; and obtaining scyllo-inositol by reducing the obtained scyllo-inosose.

In the producing method, the step of producing scyllo-inosose from myo-inositol using a $NAD^+$-independent myo-inositol 2-dehydrogenase or a strain that shows high activity of the enzyme (microorganism for the production of scyllo-inosose) can be performed by a method described above. The scyllo-inosose obtained from the step may be used for the reducing step after being isolated and purified, or may be used for the reducing step without being isolated and purified. In the case of producing scyllo-inosose using a microorganism for the production of scyllo-inosose, a cultured filtrate obtained by separating only cells without isolating scyllo-inosose from a culture solution in which scyllo-inosose has been produced and accumulated may be used for the reducing step.

Examples of a reducing agent capable of reducing scyllo-inosose into scyllo-inositol in a reaction solution system include, but not limited to, sodium borohydride, lithium borohydride, potassium borohydride, sodium trimethoxy borohydride, and cyanated sodium borohydride. Reduction of scyllo-inosose using those reducing agents results in production of scyllo-inositol and myo-inositol. Production ratios thereof vary depending on a reaction temperature or kinds of reducing reagents, however, generally a mixture consisting of scyllo-inositol and myo-inositol in a ratio of about 4:6 can be obtained. Thus, scyllo-inositol has to be separated and purified from the mixture.

Furthermore, the reduction of scyllo-inosose into scyllo-inositol may be performed using a novel scyllo-inositol dehydrogenase provided by the present invention as described hereinbelow.

In order to separate and purify scyllo-inositol from a reduced reaction solution, a general method of isolating and purifying a normal aqueous neutral substance can be applied. For example, at first, a reaction solution is treated with activated carbon, an ion exchange resin, or the like, to thereby obtain an aqueous solution containing scyllo-inositol and myo-inositol but almost no other impurities. In order to obtain only scyllo-inositol from the aqueous solution, it is effective to utilize the difference in solubility to water. That is, a method of obtaining scyllo-inositol comprising: concentrating the aqueous solution; and allowing the scyllo-inositol having low solubility to water to be precipitated as a solid can be used.

Furthermore, as described hereinbelow, scyllo-inositol may be separated and purified by a method comprising: adding boric acid and NaCl to the obtained scyllo-inositol-containing solution to thereby forming a scyllo-inositol/boric acid complex; filtrating and separating the complex; allowing the boric acid to be released by means of the acid; and allowing the scyllo-inositol to be crystallized by adding an organic solvent such as methanol.

3. Scyllo-inositol Dehydrogenase and a Method of Producing Scyllo-inositol Using the Same Other embodiment of the present invention relates to a novel enzyme scyllo-inositol dehydrogenase and a method of producing scyllo-inositol using the enzyme.

<Scyllo-inositol Dehydrogenase>

As represented in the following reaction formula, scyllo-inositol dehydrogenase of the present invention catalyzes an oxidation-reduction reaction between scyllo-inositol and scyllo-inosose, and stereospecifically reduces scyllo-inosose into scyllo-inositol in the presence of NADH or NADPH.

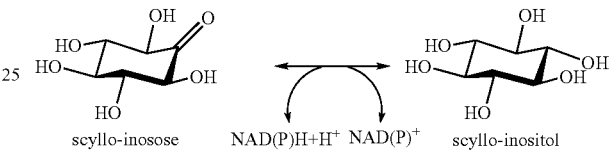

The origin of such a scyllo-inositol dehydrogenase is not limited as long as it has the above-described activity. However, scyllo-inositol dehydrogenase is preferably derived from microorganisms and particularly preferably derived from *Escherichia coli*, the genus *Acetobacter*, the genus *Bacillus*, the genus *Agrobacterium*, the genus *Xanthomonas*, or the like. It is particularly preferably derived from *Escherichia coli* K-12 strain ATCC10798, *Acetobacter* sp. AB10281 strain FERM BP-10119, *Bacillus subtilis* 168 strain ATCC23857, *Agrobacterium tumefacience* C58 strain ATCC33970, *Agrobacterium* sp. AB10121 strain FERM P-17383, or *Xanthomonas campestris pv. campestris* ATCC33913.

The scyllo-inositol dehydrogenase of the present invention includes a scyllo-inositol dehydrogenase having the following physiological properties.

Reaction: as shown by the following reaction formula, it catalyzes the oxidation-reduction reaction between scyllo-inositol and scyllo-inosose and stereospecifically reduces scyllo-inosose into scyllo-inositol in the presence of NADH or NADPH.

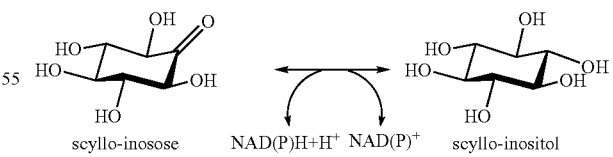

The method of determining the activity of scyllo-inositol dehydrogenase can be either of a method of determining the reducing activity or a method of determining oxidizing activity. However, the method of determining the reducing activity is preferable, because accuracy is low in the determination of the oxidizing activity due to the activity derived from co-existing myo-inositol 2-dehydrogenase and a faint activity of the oxidizing activity itself.

The determination of the reducing activity is achieved by determining a decrease in absorption at 340 nm of NADH or NADPH under a condition in which scyllo-inositol is used as a substrate and coexists with NADH or NADPH. Furthermore, the determination can be achieved by determining whether a product in a solution after completion of the reaction is scyllo-inositol or myo-inositol by means of an analyzing apparatus such as HPLC or GLC.

Furthermore, the scyllo-inositol dehydrogenase of the present invention preferably has the following physiological properties.

Molecular weight and association property: 38 to 46 k Dalton, the scyllo-inositol dehydrogenase forms a dimer or a trimer.

The molecular weight can be calculated as an estimated molecular weight of the enzyme from a result of sodium dodecyl sulfate-polyacrylamide electrophoresis (SDS-PAGE) or the like or based on the full length of the DNA. The association property can be determined by: measuring the activity of a faction fractionated using a gel filtration column (2000SWXL, manufactured by Tosoh Corporation); calculating the molecular weight of a corresponding molecular weight; and making a value obtained by dividing the molecular weight by the molecular weight of the enzyme into an integer.

Further, the scyllo-inositol dehydrogenase of the present invention preferably has the following physiological properties.

Coenzyme: $NAD^+$ or $NADP^+$, or NADH or NADPH is used as a coenzyme.

Selectivity of the coenzyme can be confirmed by: mixing 5 μl of a reaction solution (200 mM Tris buffer of pH 8.0, 2% of NADPH or NADH, and 1% of scyllo-inosose) and 5 μl of an enzyme solution; allowing the mixture to react at 36° C. for 30 minutes; adding 500 μl of water immediately after the completion of the reaction; determining the absorbance at 340 nm; and determining a decrease in the absorbance at 340 nm with respect to a blank value of a test solution including water instead of the enzyme solution. The values indicated by "%" each represent a percentage of weight/volume (w/v), and hereinafter, it also has the same meaning when a concentration is indicated by "%".

Further, a coenzyme-relative activity can be confirmed using the above-described determination method. The enzyme of the present invention can be divided into groups each having NADPH:NADH ratio of 100:1 to 100:10, 100:10 to 100:30, 100:30 to 100:60, and 100:60 to 100:120 according to the coenzyme-relative activities.

Furthermore, the scyllo-inositol dehydrogenase of the present invention preferably has the following physiological properties.

Activation by heavy metals: it is activated in the presence of $Co^{2+}$ ion, or may be activated in the presence of $Mn^{2+}$, $Zn^{2+}$, or $Ca^{2+}$ ion.

Inhibition by heavy metals: it is inhibited in the presence of $Sn^{2+}$ ion, or may be inhibited in the presence of $Zn^{2+}$ ion.

Effects by the heavy metals can be confirmed by: mixing 5 μl of a reaction solution (200 mM Tris buffer of pH 8.0 containing 2% of NADPH, 1% of scyllo-inosose, and 2 mM metal salt) and 5 μl of an enzyme solution; allowing the mixture to react at 36° C. for 30 minutes; adding 500 μl of water immediately after the completion of the reaction; determining the absorbance at 340 nm; and determining a decrease in the absorbance at 340 nm with respect to a blank value of a test solution containing water instead of the enzyme solution. The term "activated" means the case where the enzymatic activity of a fraction added with 1 mM of a heavy metal is 105% or more, preferably 120% or more, with respect to the enzymatic activity of a fraction added with no heavy metal as 100%. On the other hand, the term "inhibited" means the case where the enzymatic activity of the fraction added with 1 mM of a heavy metal is 95% or less, preferably 70% or less, with respect to the enzymatic activity of the fraction added with no heavy metal as 100%.

Further, the scyllo-inositol dehydrogenase of the present invention preferably has the following physiological properties.

Optimum pH: the enzyme of the present invention has an activity at pH of 5 to 9.

The optimum pH can be confirmed by: mixing 5 μl of a reaction solution (200 mM Tris buffer of pH 5.0 to 9.0 containing 2% of NADPH, and 1% of scyllo-inosose) and 5 μl of an enzyme solution; allowing the mixture to react at 36° C. for 30 minutes; adding 500 μl of water immediately after the completion of the reaction; determining the absorbance at 340 nm; and determining a decrease in the absorbance at 340 nm with respect to a blank value of a test solution containing water instead of the enzyme solution. The term "optimum pH" means a pH at which the enzyme has 90% or more of the maximum activity. The enzyme of the present invention can be divided depending on, for example, a range of the optimum pH into groups each having: an optimum pH in an acidic region (optimum pH is pH of 5.5 to 6.5); an optimum pH in a neutral region (optimum pH is pH of 6.5 to 7.5 or 6.5 to 8.5); and an optimum pH in an alkaline region (optimum pH is pH of 7.0 to 8.5 or 7.5 to 9.0).

Further, the scyllo-inositol dehydrogenase of the present invention preferably has the following physiological properties.

Thermal stability: the scyllo-inositol dehydrogenase of the present invention is stable at up to 60° C.

The thermal stability can be confirmed by: treating an enzyme solution at a predetermined temperature for 10 minutes followed by cooling it; mixing the enzyme solution and 5 μl of a reaction solution (200 mM Tris buffer of pH 5.0 to 9.0 containing 2% of NADPH, and 1% of scyllo-inosose); allowing the mixture to react at 36° C. for 30 minutes; adding 500 μl of water immediately after the completion of the reaction; determining the absorbance at 340 nm; and determining a decrease in the absorbance at 340 nm with respect to a blank value of a test solution containing water instead of the enzyme solution. The term "thermally stable" means a case where the above-described enzyme which was heat-treated still has 90% or more of its activity with respect to the activity of a fraction which was treated at 20° C. for 10 minutes as 100%.

Further, the scyllo-inositol dehydrogenase of the present invention preferably has the following physiological properties.

Km value with respect to scyllo-inosose: Km value with respect to scyllo-inosose is 2 to 13 mM.

The Km value with respect to scyllo-inosose can be confirmed by: mixing 5 μl of a reaction solution (200 mM Tris buffer of pH 8.0 containing 2% of NADPH, and 0.001 to 2.5% of scyllo-inosose) and 5 μl of an enzyme solution; allowing the mixture to react at 36° C. for 30 minutes; adding 500 μl of water immediately after the completion of the reaction; determining the absorbance at 340 nm; and determining a decrease in the absorbance at 340 nm with respect to a blank value of a test solution containing water instead of the enzyme solution. The determination is carried out such that the Km value is calculated after reciprocal plot according to the general method. The enzyme of the present invention can be divided into groups, for example, each having a Km value with respect to scyllo-inosose of less than 4 mM, not less than 4 mM and less than 10 mM, and not less than 10 mM and less than 13 mM, respectively.

Further, the scyllo-inositol dehydrogenase of the present invention preferably has the following physiological properties.

Substrate specificity: Examples of a substrate having a relative activity of 70% or more include scyllo-inositol (SI), myo-inositol (MI), D-chiro-inositol (DCI), epi-inositol (EI), and L-chiro-inositol (LCI). Examples of a substrate having a relative activity of 20% or more and less than 70% include L-chiro-inositol (LCI), epi-inositol (EI), muco-inositol (MuI), myo-inositol (MI), D-chiro-inositol (DCI), allo-inositol (AI), and neo-inositol (NI). Examples of a substrate having a relative activity of less than 20% include allo-inositol (AI), neo-inositol (NI), D-chiro-inositol (DCI), L-chiro-inositol (LCI), epi-inositol (EI), and muco-inositol (MuI).

The substrate specificity can be confirmed by determining a relative activity with respect to the reactivity to scyllo-inositol based on the oxidizing activity. Examples of an inositol isomer include scyllo-inositol (SI), myo-inositol (MI), D-chiro-inositol (DCI), L-chiro-inositol (LCI), epi-inositol (EI), muco-inositol (MuI), allo-inositol (AI), and neo-inositol (NI). The substrate specificity of scyllo-inositol dehydrogenase of the present invention can be shown as divided sections each having a relative activity of not less than 70%, less than 70% and not less than 20%, and less than 20%.

The determination method can be performed by: mixing 50 µl of a reaction solution (200 mM Tris buffer having of pH 8.0 containing 1% of the various inositol isomers (only neo-inositol is 0.4%), 0.002% of NADP$^+$, 0.002% of diaphorase, and 0.01% of nitrotetrazolium blue) and 50 µl of an enzyme solution; and determining an increase in the absorbance at 545 nm every 3 minutes at 25° C. using a microplate reader.

Those physiological properties preferably have a combination of any of the physiological properties.

<Production and Purification of Scyllo-inositol Dehydrogenase>

Examples of the microorganism to be used for the production of scyllo-inositol dehydrogenase include, but not limited as long as the microorganism has the ability to produce the enzyme, *Escherichia coli* K-12 strain ATCC10798 (hereinafter, also referred to as *Escherichia coli* K-12 strain), *Acetobacter* sp. AB10281 strain FERM BP-10119 (hereinafter, also referred to as AB10281 strain), *Bacillus subtilis* 168 strain ATCC23857 (hereinafter, also referred to as *Bacillus sub.* 168 strain or *B. sub.* 168 strain), *Agrobacterium tumefaciense* C58 strain ATCC33970 (hereinafter, also referred to as *A. tume.* C58 stain), *Agrobacterium* sp. AB10121 strain FERM P-17383 (hereinafter, also referred to as an AB10121 strain), and *Xanthomonas campestris pv. campestris* strain ATCC339913 (hereinafter, also referred to as *X. camp.*).

For producing scyllo-inositol dehydrogenase, conventionally known common media for a microorganism can be used as a medium for culturing those microorganisms. For example, the composition of a medium to be used for culture of *Acetobacter* sp. AB10281 strain FERM BP-10119, *Bacillus subtilis* 168 strain ATCC23857, *Agrobacterium tumefaciense* C58 strain ATCC33970, *Acetobacter* sp. AB10121 strain FERM P-17383, or *Xanthomonas campestris pv. campestris* strain ATCC33913 is not particularly limited as long as the object can be achieved. The medium may be a medium containing myo-inositol which is a raw material to be converted into scyllo-inositol, in addition to carbon sources, nitrogen sources, organic nutrients, inorganic salts, and the like. Both a synthetic medium and a natural medium can be used. The medium is preferably added with 0.1% to 40%, more preferably 10% to 30% of myo-inositol; 0.1% to 20%, more preferably 0.3% to 5% of glycerol, sucrose, maltose, or starch as a carbon source; and 0.01% to 5.0%, preferably 0.5% to 2.0% of a yeast extract, peptone, casamino acid, ammonium sulfate, ammonium chloride, ammonium nitrate, urea, or the like as a nitrogen source. In addition, if necessary, inorganic salts each capable of forming an ion of sodium, potassium, calcium, magnesium, cobalt, manganese, zinc, iron, copper, molybdenum, phosphoric acid, sulfuric acid, or the like can be added to the medium. A hydrogen-ion concentration in the culture solution does not particularly need to be adjusted. However, cells containing scyllo-inositol dehydrogenase are efficiently obtained in the culture solution adjusted to preferably pH of 4 to 10, more preferably pH of 5 to 9.

Culture conditions vary depending on a kind of the medium. However, a culture temperature is 12 to 38° C., preferably 20 to 27° C. Culture may be performed aerobically by, for example, shaking the liquid medium or aerating air or an oxygen gas into the liquid medium. A culture period may be until when the accumulation of the scyllo-inositol dehydrogenase becomes maximum or an amount required to obtain an adequate activity, and is generally 1 to 10 days, preferably 3 to 8 days.

Meanwhile, the composition of a medium to be used for culturing *Escherichia coli* K-12 strain ATCC10798 is not particular limited as long as it accomplishes the object. The medium may be a medium containing carbon sources, nitrogen sources, organic nutrients, inorganic salts, and the like. Both a synthetic medium and a natural medium can be used. Examples of the medium include LB medium, TB medium, and YT medium. In addition, 0.05 to 1%, preferably 0.5% of sorbose is preferably added to the medium, as a substance which increases the specific activity of scyllo-inositol dehydrogenase of the *Escherichia coli* K-12 ATCC10798 strain about three times larger. Culture conditions vary depending on a kind of the medium. However, a culture temperature is 28 to 38° C., preferably 36° C. Culture may be performed aerobically by, for example, shaking the liquid medium or aerating air or an oxygen gas into the liquid medium. A culture period may be until when the accumulation of the scyllo-inositol dehydrogenase becomes a maximum or an amount required to obtain an adequate activity, and is generally 1 to 3 days, preferably 1 day.

Scyllo-inositol dehydrogenase can be obtained by separating and purifying the enzyme from thus cultured cells. The separation and purification of the enzyme can be performed in the same manner as a general purification method for a protein. The separation and purification method will be specifically described hereinbelow, however, it is not limited thereto.

First, in order to collect the cells after culture, a method such as centrifugal separation or membrane concentration can be used. If necessary, at this point, the cells can be washed by being suspended to an appropriate solution and being collected again using a method such as centrifugal separation or membrane concentration. Thus obtained cells are disrupted by means of a physical method such as use of an auto-mill or ultrasonic, to thereby extract the enzyme of the present invention which presents in the cells.

The cell-lysis solution containing the disrupted cells is divided into soluble components and insoluble components using a method such as centrifugal separation or membrane concentration. After that, the enzyme of interest can be purified from the soluble components in accordance with a general procedure for enzyme purification. That is, a column operation using an affinity column such as Blue-Toyopearl (manufactured by Tosoh Corporation), an ion exchange column typified by a DEAE column or a CM column, a gel-filtration column, or a hydroxyapatite column, as well as a batch-wise operation method such as an ammonium sulfate fractionation method or isoelectrite precipitation method can be used.

The method of determining the scyllo-inositol dehydrogenase activity can be either of the method of determining the reducing activity or the method of determining the oxidizing activity. However, the method of determining the reducing activity is preferable, because accuracy is low in the determination of the oxidizing activity due to the activity of co-existing myo-inositol 2-dehydrogenase and activity of the oxidizing activity itself is low. The determination of the reducing activity is achieved by determining a decrease in absorption of NADH or NADPH at 340 n under a condition in which scyllo-inosose is used as a substrate and coexists with NADH or NADPH. Furthermore, the determination can be achieved by determining whether a product in a solution after completion of the reaction is scyllo-inositol or myo-inositol by means of an analyzing apparatus such as HPLC or GLC.

The degree of purification of the enzyme can be confirmed by electrophoresis using Native-PAGE, sodium dodecyl sulfate (SDS)-PAGE, or the like. In addition, the corresponding protein can be highly purified by trans-blotting the enzyme to a protein adsorptive membrane such as a PVDF membrane.

Specific examples of the scyllo-inositol dehydrogenase of the present invention include the following proteins (a) and (b).

(a) A protein consisting of an amino acid sequence of SEQ ID NO: 2, 4, 6, 8, 10, 12, 14, or 28.

(b) A protein consisting of an amino acid sequence of SEQ ID NO: 2, 4, 6, 8, 10, 12, 14, or 28, including substitution, deletion, insertion, and/or addition of one or plural of amino acids; and catalyzing the oxidation-reduction reaction between scyllo-inositol and scyllo-inosose; and having an enzymatic activity to stereospecifically reduce scyllo-inosose into scyllo-inositol in the presence of NADH or NADPH.

Of those, a scyllo-inositol dehydrogenase having the amino acid sequence of SEQ ID NO: 28 is a novel protein provided by the present invention.

The term "protein which has an amino acid sequence including substitution, deletion, insertion, and/or addition of one or plural of amino acids; catalyzes the oxidation-reduction reaction between scyllo-inositol and scyllo-inosose; and has an enzymatic activity to stereospecifically reduce scyllo-inosose into scyllo-inositol in the presence of NADH or NADPH" means that the protein may have substitution, deletion, insertion, and/or addition of one or plural of amino acid residues which does not substantially inhibit the enzymatic activity to catalyze the oxidation-reduction reaction between scyllo-inositol and scyllo-inosose and to stereospecifically reduce the scyllo-inosose into the scyllo-inositol in the presence of NADH or NADPH.

That is, a naturally-occurring protein may have variations such as substitution, deletion, insertion, and/or addition of amino acid residues in an amino acid sequence owing to polymorphism and variation of a DNA encoding the protein, as well as a modification reaction or the like in a cell after and during purification of the protein. However, some of the naturally-occurring proteins which may have variations are known to have physiological and biological activities which are substantially the same as those of a protein having no variation. As described above, a protein having slight differences in the structure but has no significant difference in the function is included in the protein of the present invention. A protein made by artificially introducing the above-described variations into the amino acid sequence is also included, and further various mutants can be produced in this case. Furthermore, a certain kind of a protein is known to have a peptide region not essential for the activity. Examples of such a peptide region include a signal peptide present in a protein which is extracellularly secreted and a pro-sequence existing in a protease precursor or the like. Most of those regions are removed after translation or upon conversion into a mature protein. Such proteins have different primary structures but are proteins finally having the same function, therefore they are included in the scyllo-inositol dehydrogenase of the present invention.

The term "plural of amino acids" as used herein indicates the number of amino acids which may be mutated so long as the activity of the enzyme of the present invention is not lost. For example, in the case of a polypeptide consisting of 400 amino acid residues, the number is about 2 to 20, preferably 2 to 10, more preferably 2 to 3. Furthermore, a protein having a homology of not less than 80%, more preferably not less than 90%, still more preferably not less than 95%, or particularly preferably not less than 98% to the protein of the present invention is included in the scyllo-inositol dehydrogenase of the present invention.

Further, examples of the scyllo-inositol dehydrogenase of the present invention include those each encoded by the following DNAs.

(a) A DNA comprising a coding region of the nucleotide sequence of SEQ ID NO: 1, 3, 5, 7, 9, 11, 13, or 27.

(b) A DNA which: hybridizes under stringent conditions with a DNA having the nucleotide sequence of SEQ ID NO: 1, 3, 5, 7, 9, 11, 13, or 27 or a nucleotide sequence complementary to the nucleotide sequence; and encodes a protein which catalyzes the oxidation-reduction reaction between scyllo-inositol and scyllo-inosose and has an enzymatic activity to stereospecifically reduce scyllo-inosose into scyllo-inositol in the presence of NADH or NADPH.

Of those, a DNA having the nucleotide sequence of SEQ ID NO: 27 is a novel DNA encoding scyllo-inositol dehydrogenase provided by the present invention.

The term "stringent conditions" used herein mean conditions where a so-called specific hybrid is formed and nonspecific hybrid is not formed (see, Sambrook, J. et al., Molecular Cloning A Laboratory Manual, Second Edition, Cold Spring Harbor Laboratory Press (1989), and the like). A specific example of the "stringent condition" includes a condition in which: hybridization is performed in a solution containing 50% formamide, 4×SSC, 50 mM HEPES (pH of 7.0), 10× Denhardt's solution, and 100 g/ml of a salmon sperm DNA at 42° C.; and then washing is performed with 2×SSC, 0.1% SDS solution at room temperature and 0.1×SSC, 0.1% SDS solution below 50° C. In other words, the examples include a condition where DNAs having homology of preferably not less than 80% or more, more preferably not less than 90%, still more preferably not less than 95%, and particularly preferably not less than 98% specifically hybridize. That is, a DNA having homology of not less than 80%, more preferably not less than 90%, still more preferably not less than 95%, and particularly preferably not less than 98% to the nucleotide sequence of SEQ ID NO: of 1, 3, 5, 7, 9, 11, 13, or 27 is included in the DNA encoding the scyllo-inositol dehydrogenase of the present invention.

<Method of Producing Scyllo-inositol Using Scyllo-inositol Dehydrogenase>

Furthermore, the present invention relates to a method of producing scyllo-inositol, comprising: subjecting inexpensive myo-inositol as a substrate to enzyme conversion via scyllo-inosose into scyllo-inositol in the presence of NADH or NADPH in a solution in which scyllo-inositol dehydrogenase and myo-inositol 2-dehydrogenase coexist (see, FIG. 1).

The scyllo-inositol dehydrogenase to be used in the producing method may be an enzyme produced by purification of the above-described enzyme or may be a recombinant enzyme produced by genetic engineering using a DNA encoding scyllo-inositol dehydrogenase.

The DNA encoding scyllo-inositol dehydrogenase can be obtained, for example, by amplifying the DNA having the nucleotide sequence of SEQ ID NO: 1, 3, 5, 7, 9, 11, 13, or 27 by means of a polymerase chain reaction (PCR) using the whole genome extracted from a microorganism as a template.

Further, the DNA encoding scyllo-inositol dehydrogenase can be obtained by isolating a homologous DNA searched based on a homology. Here, it is highly likely that a series of genes having high homology which are referred to as ydgJ gene is a DNA encoding scyllo-inositol dehydrogenase.

Thus obtained DNA is inserted into a plasmid vector. A plasmid vector to be used at this time is preferably an expression plasmid vector having a multi-cloning site, however, other plasmid vector which is capable of expressing an enzyme and has restriction enzyme sites can be used. A plasmid can be constructed by: attaching an appropriate restriction enzyme site on a terminal of a fragment; and ligating the site with the same restriction enzyme site present on the plasmid vector.

Further, a promoter to be used for expression of the DNA which has been inserted in the plasmid is not particularly limited as long as the DNA is expressed in a host microorganism. For example, a lac promoter, tac promoter, or the like can be used.

Thus prepared recombinant plasmid vector can be introduced into a host microorganism. A host microorganism to be used at this time is not particularly limited as long as the recombinant plasmid vector is stable and autonomously replicable. A host microorganism which is generally used for gene recombination such as a microorganism belonging to the genus Escherichia or the genus *Bacillus* is preferably used, and *Escherichia coli* is more preferably used.

As a method of introducing the recombinant plasmid vector into the host microorganism, a method of introducing a recombinant DNA in the presence of an calcium ion or a competent cell method may be performed when the host microorganism is a microorganism belonging to the genus *Escherichia*, and the competent cell method, a protoplast method, an electroporation method, or a microinjection method can be used when the host microorganism is a microorganism belonging to the genus *Bacillus*. Selection of the presence or absence of a desirable recombinant DNA introduced into a host microorganism may be performed by: culturing the host microorganisms of interest in a selection medium based on a drug-resistance marker contained in the recombinant plasmid vector; and selecting the host microorganisms which is grown.

Next, a medium to be used for the expression and induction of the enzyme is not particularly limited as long as the host microorganism stably grows in the medium. Examples of such a medium include Nutrient Broth and L-Broth. Furthermore, depending on the kind of the plasmid vector, an inducer such as isopropyl thiogalactopyranoside (IPTG) may be added in order to express a DNA in the medium or the inducer may be added during culture.

A host microorganism introduced with the recombinant plasmid vector having thus prepared DNA is cultured to express the DNA of the present invention. The microorganism having the expressed enzyme of the present invention is subjected to centrifugal separation. The medium is removed and then the microorganism as a pellet is washed with water, followed by centrifugal separation, to thereby obtain washed cells. The washed cells are suspended in water or an appropriate solution, and the suspended cells are disrupted. After disruption, centrifugal separation is performed. Thus, a solution containing a recombinant enzyme derived from the DNA of the present invention in the supernatant can be obtained.

The cells expressing the recombinant enzyme can be subjected to a reaction as a cell suspension obtained by adding the cells as they are to a reaction solution after being washed. However, a solution containing the enzyme which had been present in the cells prepared by disrupting the cells and extracting the enzyme is preferably used. In addition, the extract can be used after purification. The purification includes an ammonium sulfate fractionation treatment, or the purification can be performed by column chromatography using a linear gradient of a salt concentration or a temperature treatment after adsorption to an ion exchange resin. Furthermore, the enzyme of the present invention can be used as an immobilized enzyme or immobilized cells. A general immobilizing method such as a gel embedding method or an ion exchange resin adsorbing method can be applied as an immobilizing method.

Meanwhile, an enzyme which oxidizes myo-inositol and produces scyllo-inositol in the presence of $NAD^+$ or $NADP^+$ is preferably used as myo-inositol 2-dehydrogenase.

In the production method, a known $NAD^+$ or $NADP^+$-dependent myo-inositol 2-dehydrogenase can be used. For example, a commercially available enzyme, an enzyme produced by purification from cultured cells of *Bacillus subtilis* or *Bacillus halodurans*, or a recombinant enzyme expressed by genetic engineering based on known gene sequence may be used.

Examples of the amino acid sequence of a known myo-inositol 2-dehydrogenase are registered in the protein database of National Center for Biotechnology Information (NCBI) under an accession numbers of 2636516, 17982589, 23464076, 10174936, 17742455, 50120397, 28853468, and 13422633. Also, information of nucleotide sequence encoding those amino acid sequences can be obtained by referring to CDS of the accession numbers.

The cells expressing the recombinant enzyme can be subjected to a reaction as a cell suspension by adding the cells as they are to a reaction solution after being washed. However, a solution containing an enzyme which had been present in the cells prepared by disrupting the cells and extracting the enzyme is preferably used. In addition, the extract of the present invention can be used after purification. The purification includes an ammonium sulfate fractionation treatment, or the purification can be performed by column chromatography using a linear gradient of a salt concentration or a temperature treatment after adsorption to an ion exchange resin. Furthermore, the enzyme of the present invention can be used as an immobilized enzyme or immobilized cells. A general immobilizing method such as a gel embedding method or an ion exchange resin adsorbing method can be applied to an immobilizing method.

When the recombinant enzyme is used, myo-inositol 2-dehydrogenase and the enzyme of the present invention can be simultaneously expressed by means of genetic engineering, an enzyme solution prepared as such can be used.

The ratio of the activity (U) between the myo-inositol 2-dehydrogenase and the scyllo-inositol dehydrogenase in the present reaction system is defined by the number of units. When the scyllo-inosose is used as the substrate at 36° C., a rate at which 1 µmol of NADH or NADPH is consumed per 1 minute is defined as 1 U. In this case, it is desirable that the ratio of the activity (U) of both enzymes would be 1:10 to 10:1, preferably 1:2 to 2:1.

The present reaction system requires the co-enzyme $NAD^+$ or $NADP^+$. It is shown that the coenzymes are recycled in the reaction solution since the co-enzymes are converted into NADH or NADPH, and NADH or NADPH are again converted into $NAD^+$ or $NADP^+$. $NAD^+$ or $NADP^+$ and NADH or NADPH differs in pH stability in a solution. $NAD^+$ or $NADP^+$ is stable at pH of 8.0 or less, and NADH or NADPH is stable at pH of 8.0 or more. Therefore, the pH of the present reaction system is preferably maintained at about pH 8.0.

Any one of $NAD^+$, NADH, $NADP^+$, and NADPH, or a mixture thereof can be used as the co-enzyme to be used in the present enzymatic reaction. However, $NAD^+$ or $NADP^+$ is desirable in view of the stability. It is desirable to add it at a concentration of 0.0001 to 0.1%, preferably 0.004 to 0.01%.

In addition, reaction rate of the present reaction significantly increases by adding scyllo-inosose, an intermediate of the present reaction system, to the reaction solution. Thus, scyllo-inosose is desirably added to become 0.01 to 3%, preferably 0.2 to 0.5% in the reaction solution.

Further, myo-inositol 2-dehydrogenase and scyllo-inositol dehydrogenase can react at pH 8.0. Therefore, the pH of the solution for the enzymatic reaction is adjusted to pH ranging from 6.0 to 8.5, and they are reacted with each other. However, it is desirable that the pH is preferably 7.7 to 8.3, more preferably 8.0, in view of the stability of $NAD^+$ or $NADP^+$ and scyllo-inosose. If necessary, a buffer may be added to the reaction to thereby maintain the pH during the reaction. The kind of the buffer to be added is not particularly limited, however, a buffer having a buffering ability at about pH 8.0 is desirable. More preferably, a phosphate buffer, Tris buffer, or the like is exemplified.

Furthermore, the myo-inositol 2-dehydrogenase is activated by $Mg^{2+}$ ion and the scyllo-inositol dehydrogenase is activated by $Co^{2+}$ ion. Thus, the addition of those metal ions increases the reaction rate. Therefore, it is desirable that Co salt and/or Mg salt is added to be 0.01 to 5.0 mM, preferably 0.2 to 2.0 mM in the reaction solution. Any salt which dissolves in water can be used as Co salt or Mg salt, and examples thereof include salts of hydrochloride and sulfate.

It is desirable to use the myo-inositol, the substrate to be used in the present invention, at a concentration of 1 to 30%, preferably 5 to 22% in the reaction solution. As the reaction proceeds, scyllo-inositol which is oversaturated by more than 1.6% precipitates as a crystal, resulting in reduction of myo-inositol. Therefore, an amount of myo-inositol corresponding to the reduction is added to the reaction solution to maintain the myo-inositol at a constant concentration, to thereby allow continuous reaction.

The reaction temperature is not particularly limited as long as the reaction proceeds. However, the reaction is preferably performed at 20 to 50° C., more preferably 35 to 40° C. in view of the solubility of the substrate, the stability of $NAD^+$ or $NADP^+$, and the heat-stability of the enzyme. Stirring is necessary in a method in which the cells are suspended since it is a heterogeneous reaction. Stirring is not necessary when the extracted enzyme is used since it is a homogenous solution, but stirring is preferably performed to make the temperature uniform.

During the enzymatic reaction, scyllo-inositol which is a reactant can precipitate as a crystalline scyllo-inositol when the concentration of the scyllo-inositol becomes equal to or larger than its solubility. The reaction does not need to be terminated when a solid-liquid separation method such as filtration or decantation is used, and the reaction can be continued by adding myo-inositol into a solution such as a filtrated solution again.

When the enzymatic reaction needs to be terminated, the enzymatic reaction itself may be terminated. Methods including heating, changing pH, addition of a denaturing agent for a protein, or the like can be used. The heating is preferable in view of the subsequent step of purification of the scyllo-inositol. For example, the reaction solution can be heated to 70 to 120° C., preferably 80 to 90° C. for 10 to 20 minutes.

In addition, the termination of the enzymatic reaction can be performed by separating the enzyme. The enzyme can be separated by passing the reaction solution through an ion exchange resin column. When an immobilized enzyme is used, the reaction solution is subjected to centrifugal separation or a filtration operation to thereby collecting the immobilized enzyme.

After the termination of the reaction or during the reaction, oversaturated scyllo-inositol precipitates as a crystal. The crystalline scyllo-inositol can be isolated by means of an operation such as filtration or centrifugal separation. When the crystalline scyllo-inositol co-exists with cells and insoluble denatured proteins, the cells and insoluble denatured proteins can be removed by dissolving the crystalline scyllo-inositol in water followed by an operation such as filtration or centrifugal separation.

A method of purifying thus obtained crystalline scyllo-inositol can be performed as follows. The point to be noted at this stage is the removal of neo-inositol in the crystalline scyllo-inositol. Neo-inositol is a substance generated such that: the fifth position of a part of myo-inositol is oxidized by scyllo-inositol dehydrogenase to generate neo-inosose; and the generated neo-inosose is reduced by the myo-inositol 2-dehydrogenase. In the present reaction system, a trace amount of the substance generates. Also, the neo-inositol is a substance having a low water-solubility of 0.5% and is apt to be precipitated as a crystal with the scyllo-inositol.

However, a scyllo-inositol solution obtained by dissolving the crystalline scyllo-inositol in water again contains almost no myo-inositol. Scyllo-inositol which contains a trace amount of the neo-inositol can be obtained by means of an operation such as filtration or centrifugal separation for isolating a crystalline scyllo-inositol to be generated by recon-centration of the scyllo-inositol solution. In addition, for higher purification, a recrystallized scyllo-inositol, which is recrystallized through concentration of the liquid after being purified by passing through a desalting column or activated carbon column, is isolated by using an operation such as filtration or centrifugal separation, to yield a pure scyllo-inositol containing no neo-inositol.

A column employing an ion exchange resin is preferable for the desalting column. For the ion exchange resin to be used at this time, any one of a strong basic ion exchange resin and a weak basic ion exchange resin, or a combination thereof, or any one of a strong acidic ion exchange resin and a weak ion exchange resin, or a combination thereof can be used. As a manner in which the ion exchange resin is reacted, a method comprising passing a solution through an ion exchange resin loaded in a column is optimum. The solution may also be desalted by filtration after being mixed in batch-wise manner and stirred with the ion exchange resin.

The activated carbon column is used for decolorization. A method comprising passing the solution through the activated carbon loaded in a column can be used. The solution may be decolorized by filtration after being mixed in batch-wise manner and stirred with the activated carbon.

Next, after the termination of the enzymatic reaction, a method of purifying the soluble scyllo-inositol which dissolves in the reaction solution can be performed as follows. The point to be noted at this stage is the removal of the myo-inositol and neo-inositol which is different from the case of the crystalline scyllo-inositol.

The soluble scyllo-inositol is dissolved together with the myo-inositol (raw material) and neo-inositol, and can be obtained as a solution by means of an operation such as filtration or centrifugal separation. Since the solution contains soluble peptides and salts in addition to the myo-inositol and neo-inositol, it is purified by passing through a desalting column or activated carbon column followed by being concentrated to a degree at which no myo-inositol precipitates (the concentration of the myo-inositol should be smaller than 21%). Then, crystalline scyllo-inositol to be precipitated can be isolated by an operation such as filtration or centrifugal separation. If necessary, a water-miscible organic solvent can be added for crystallization. Examples of such an organic solvent include methanol, ethanol, and propanol.

Meanwhile, as described hereinbelow, the scyllo-inositol may be separated and purified by a method comprising: adding boric acid and NaCl to the obtained solution containing scyllo-inositol, to thereby form a scyllo-inositol/boric acid complex; filtrating and separating the complex; allowing the boric acid to be released using an acid; and crystallizing the scyllo-inositol by adding an organic solvent such as methanol.

4. Method of Producing Scyllo-inositol from a Liquid Mixture Containing Scyllo-inositol and Neutral Sugars Other than Scyllo-inositol Furthermore, the present invention relates to a method of producing the scyllo-inositol from a liquid mixture containing the scyllo-inositol and neutral sugars other than the scyllo-inositol.

<4-1>

An embodiment of the method of the present invention is a method of producing a purified scyllo-inositol, comprising: a first step of forming a scyllo-inositol/boric acid complex by adding boric acid and a metal salt in an amount twice or more than that of the scyllo-inositol dissolved in a liquid mixture containing the scyllo-inositol and neutral acid other than the scyllo-inositol and by adjusting the pH of the liquid mixture to 8.0 to 11.0; a second step of separating the complex from the liquid mixture; a third step of cleaving into scyllo-inositol and boric acid by dissolving the separated complex in an acid; and a fourth step of isolating and purifying the scyllo-inositol from an acidic solution or an acidic suspension obtained from the third step.

The first step of the production method is a step of forming a scyllo-inositol/boric acid complex by adding boric acid and a metal salt in an amount twice or more than that of the scyllo-inositol dissolved in a liquid mixture containing the scyllo-inositol and neutral acid other than the scyllo-inositol; and adjusting the pH of the liquid mixture to 8.0 to 11.0.

As used herein, the "liquid mixture containing scyllo-inositol and neutral sugars other than the scyllo-inositol" may be a solution or a suspension. Further, it may be one which further contains substances other than the "scyllo-inositol and neutral sugars other than the scyllo-inositol", or may be one which already contains a small amount of the scyllo-inositol/boric acid complex. Preferably, the neutral sugars to be contained in the liquid mixture include neutral sugars such as tetrose, pentose, hexose, and heptose. Examples thereof include: aldose such as glucose, fructose, and galactose; ketose; various isomers of inositol; and polyalcohols such as glycerol and ethylene glycol. Here, examples of the isomers of inositol include: myo-inositol, D-chiro-inositol, L-chiro-inositol, epi-inositol, muco-inositol, allo-inositol, cis-inositol, and neo-inositol.

Of those, myo-inositol can be particularly preferably used. In this case, the "liquid mixture containing scyllo-inositol and neutral sugars other than the scyllo-inositol" includes, for example, a liquid mixture containing scyllo-inositol and myo-inositol which is obtained by reduction of scyllo-inosose as described hereinbelow.

For the scyllo-inosose to be used for the reduction reaction, for example, one obtained by oxidizing myo-inositol using a microorganism in a medium or solution can be used (JP-A-2003-102492). The scyllo-inosose obtained by the microbial oxidation may be used by dissolving the purified one, or a cultured filtrate thereof may be used. Meanwhile, scyllo-inosose prepared by oxidizing myo-inositol using a platinum catalyst can be used.

A reducing agent to be used for reduction of the scyllo-inosose into the scyllo-inositol is not particularly limited as long as it is a reducing agent capable of reducing scyllo-inosose into scyllo-inositol in water. Examples thereof include sodium borohydride, lithium borohydride, potassium borohydride, trimethoxy sodium borohydride, and cyanated sodium borohydride.

The reduction reaction of the scyllo-inosose can be performed, for example, by adding a powder or solution of a reducing agent to a solution containing the scyllo-inosose dissolved at a concentration of 20% or less (w/v). The solution is preferably stirred at this time. The heat of reaction may generate owing to the reduction reaction, therefore the reaction solution is preferably controlled to have a temperature of 50° C. or lower in order to prevent decomposition of the generated inosose. Furthermore, when a reducing agent such as sodium borohydride is used, a part of the reducing agent may be decompose to generate a hydrogen gas. Therefore, an antifoaming agent or the like is preferably added to reduce foam formation of the hydrogen gas.

In a liquid mixture of the scyllo-inositol and myo-inositol obtained from the reduction of the scyllo-inosose, the scyllo-inositol starts to gradually crystallize when its concentration exceeds about 1.6% (w/v). Generally, reduction of 5% (w/v) scyllo-inosose solution generates about 3% (w/v) of the myo-inositol and about 2% (w/v) of the scyllo-inositol. However, when the solution is left at room temperature for several hours, about 0.4% of an oversaturated part of the scyllo-inositol starts to crystallize. Therefore, when the liquid mixture of the scyllo-inositol and myo-inositol obtained from the reduction of the scyllo-inosose is used, the step of forming a scyllo-inositol/boric acid complex is preferably performed prior to the generation of the crystal of the scyllo-inositol itself. The step of forming a scyllo-inositol/boric acid complex is preferably performed immediately after the reduction reaction of the scyllo-inosose.

The first step is performed by adding boric acid and metal salts into a "liquid mixture containing scyllo-inositol and neutral sugars other than the scyllo-inositol" such as the above-described "liquid mixture containing scyllo-inositol and myo-inositol" in an amount twice or more moles, preferably twice or more moles but three times or less moles larger than that of the scyllo-inositol dissolved in the liquid mixture, respectively, and after they are dissolved, adjusting the liquid mixture to be alkaline at pH of 8.0 to 11.0, preferably pH of 9.0 to 10.0. The term "twice moles" as used herein refers to a number of moles of twice. The pH of the reaction solution can be adjusted using a base such as NaOH, KOH, $Na_2CO_3$, or $K_2CO_3$.

Here, examples of metal salts to be added include one or more kinds metal salts selected from the group consisting of NaCl, $NaHCO_3$, $Na_2CO_3$, $Na_2SO_4$, $NaHSO_4$, $NaH_2PO_4$, $Na_2HPO_4$, $Na_3PO_4$, borax, KCl, $KHCO_3$, $K_2CO_3$, $K_2SO_4$, $KHSO_4$, $KH_2PO_4$, $K_2HPO_4$, $K_3PO_4$, $MgCl_2$, $MgCO_3$, and $MgSO_4$. The amount of boric acid to be added, or total amount of boric acid if the liquid mixture already contains boric acid, is twice or more moles, preferably twice or more but three times or less moles that of the dissolved scyllo-inositol.

The first step is preferably carried out with stirring for efficiently dissolving the boric acid and metal salts in the liquid mixture and making the solution homogenous upon the adjustment of pH. The step is preferably performed at a temperature ranging from 5° C. to 85° C., preferably 15 to 40° C. Time needed for the step is not particularly limited as long as a required amount of the scyllo-inositol/boric acid complex is formed, however, 12 to 76 hours are preferable in order to collect it at an yield of 90% or higher.

Most of the scyllo-inositol/boric acid complex exists as a precipitate in the liquid mixture since it has solubility of 0.01% (w/v) or less to water as confirmed by means of NMR. In the second step, the scyllo-inositol/boric acid complex is separated from the liquid mixture. A general solid separation operation can be applied to the step, for example, a filtration operation or centrifugal separation operation may be applied. The scyllo-inositol left in the liquid mixture in which the scyllo-inositol/boric acid complex has been separated by the above step has a concentration of 0.2% (w/v) or less. Therefore, most of the scyllo-inositol in the liquid mixture before the initiation of the reaction can be collected in a form of the scyllo-inositol/boric acid complex. Meanwhile, neutral sugars such as the myo-inositol exist in a dissolved state in a solution. Therefore, the neutral sugars exist in a filtrate upon a filtration operation, and thus the neutral sugars and the scyllo-inositol can be separated by the step.

The separated scyllo-inositol/boric acid complex can be dried and isolated as a powder. If necessary, it can be also isolated as a crystal by means of recrystallization using hot water.

Next, the third step involves dissolution of the separated scyllo-inositol/boric acid complex into an acid. The dissolution cleaves the scyllo-inositol/boric acid complex into scyllo-inositol and boric acid, and metal ions bound to the complex also dissociate therefrom in the solution. The kind of an acid to be used for the dissolution in the step is not particularly limited as long as it can dissolve the complex, however, an acid which does not form a salt having a low solubility depending on the kind of the metal ion is desirable. Preferably, mineral acids such as hydrochloric acid, sulfuric acid, nitric acid, and phosphoric acid can be used, and hydrochloric acid can be more preferably used. Since those acids each gives rise to a neutralization reaction with the metal ions generated by the dissolution, it is preferably adjusted so that a solution containing the scyllo-inositol/boric acid complex finally becomes an acidic solution of 0.1 N or higher. Also, to efficiently dissolve the scyllo-inositol/boric acid complex, the complex is preferably dissolved with an acid of 1 N or higher to finally make an acidic solution of 0.1 N or higher.

The fourth step involves isolation and purification of the scyllo-inositol from the acidic solution or acidic suspension obtained from the third step. The method of isolating and purifying the scyllo-inositol from the acidic solution is not particularly limited. However, for example, a method comprising using a resin such as an ion exchange resin as described hereinbelow or a method utilizing the difference in solubility to an organic solvent can be used.

Further, a method comprising vacuum distillation as an ester of a lower alcohol and boric acid by adding a lower alcohol after releasing boric acid may be used (Journal of Organic Chemistry, vol. 23, p. 329-330, 1958).

Of those methods, the method of isolating and purifying the scyllo-inositol using an ion exchange resin can be performed as follows. In this case, the solution obtained from the third step is preferably an acidic solution of 0.1 N or higher in which the complex completely dissolves therein. Also, the acidic solution is preferably prepared by adding an acid in an amount such that a ratio of the scyllo-inositol/boric acid complex therein becomes 2.5 (w/v) % or less, in order not to precipitate free scyllo-inositol.

First, such acidic solution is brought into contact with a strong acidic ion exchange resin to thereby remove metal ions. The strong acidic ion exchange resin to be used is not particularly limited as long as it adsorbs the metal ions, and an example thereof includes an ion exchange resin having a sulfate group. An example thereof includes Duolite C20 $H^+$ type (manufactured by Sumitomo Chemical Co., Ltd.). The contact may be performed by an operation comprising batch-wise addition of the strong acidic ion exchange resin into a given amount of the solution and then stirring. However, it is preferable that the solution is passed through the strong acidic ion exchange resin loaded in a column.

Next, the solution from which the metal ions are removed by means of the strong acidic ion exchange resin is brought into contact with a strong basic ion exchange resin or a boric acid-adsorbing resin in order to remove boric acid. Those resins are not particularly limited as long as they adsorb boric acid. An example of the strong basic ion exchange resin includes a resin having a quaternary ammonium group, and an example of the boric acid-adsorbing resin includes a resin having an N-methylglucamine group. A specific example of the strong basic ion exchange resin includes Duolite A116 $OH^-$ type (manufactured by Sumitomo Chemical Co., Ltd.). A specific example of the boric acid-adsorbing resin includes Duolite ES371N (manufactured by Sumitomo Chemical Co., Ltd.). The contact may be performed by an operation comprising batch-wise addition of the ion exchange resin into a given amount of the solution and then stirring. However, it is preferable that the solution is added to the ion exchange resin loaded in a column.

The order of the resins with which the solution is contacted is not random because the boric acid and scyllo-inositol dissociate from each other in an acidic state. The solutions are contacted with the strong acidic ion exchange resin, the strong basic ion exchange resin, and the boric acid-adsorbing resin, in this order.

A solution in which the metal ions and boric acid are removed by being contacted with those resins contains only scyllo-inositol that is a neutral sugar. Therefore, by concentrating the solution using a general method to precipitate the scyllo-inositol, a crystal or powder of the purified scyllo-inositol can be isolated.

Further, in the fourth step, in a case where the scyllo-inositol is isolated and purified using the difference in solubility to an organic solvent, it can be performed as follows. In the method, a solution obtained by the dissolution with the acid used in the third step may be a dissolved solution or a suspension because the purification operation using the ion exchange resins or the like is not performed until the addition of the organic solvent after the dissolution. In the third step, in order to facilitate the scyllo-inositol to be precipitated after dissolution, the acid is preferably added in such an amount that the ratio of the scyllo-inositol/boric acid complex is 2.5% (w/v) or more, preferably 3.0% to 10% (w/v), more preferably 4.0% to 6.0% (w/v).

First, a water-soluble organic solvent is added to the obtained acidic solution or suspension to allow free scyllo-inositol to be precipitated. The organic solvent to be used is not particularly limited as long as it is a solvent which allows the scyllo-inositol to be precipitated while boric acid is dissolved and metal salts consisting of the acid and the salt are dissolved. Examples of such an organic solvent include ethanol and methanol.

The amount of the organic solvent is as follows: when ethanol is used, ethanol is preferably added in an amount 0.3 to 3 times larger, more preferably 0.6 to 1.5 times larger than that of the acidic solution. When methanol is used, methanol is preferably added in an amount 0.3 to 5 times larger, more preferably 0.9 to 2 times larger than that of the acidic solution. In particular, the organic solvent is efficiently added in the above amount when the metal salt to be used to form the scyllo-inositol/boric acid complex is one or more of NaCl, $NaHCO_3$, and $Na_2CO_3$. In addition, a liquid mixture added with the aqueous organic solvent is preferably adjusted to be an acidic solution of 0.1 N or more.

In the fourth step, when a mixture is a homogenous solution, it is not necessary to perform stirring, but when a mixture is a suspension, it is preferable to perform stirring. The temperature of mixing is not particularly limited as long as it is a temperature at which only scyllo-inositol precipitates, however a temperature of –10° C. to 50° C. is preferable and a temperature of 4° C. to 35° C. is more preferable. The time of mixing is preferably 10 minutes to 24 hours, more preferably 3 to 5 hours.

Such operation allows only scyllo-inositol to be precipitated. The precipitated scyllo-inositol can be separated from the solution by means of filtration or a general solid-liquid separation operation such as centrifugal separation. Thus obtained scyllo-inositol is pure, however, the scyllo-inositol can be obtained as a crystal by means of a method such as recrystallization if necessary. The precipitated scyllo-inositol may be further purified using an ion exchange resin or the like after being dissolved in water, to thereby increase its purity.

<4-2> Method of Producing Scyllo-inositol from Scyllo-inosose without going through Scyllo-inositol/Boric Acid Complex Next, another embodiment will be described which comprises a method of producing scyllo-inositol from a liquid mixture containing the scyllo-inositol and neutral sugars other than the scyllo-inositol.

This method is a method of producing scyllo-inositol comprising: a first step of obtaining a liquid mixture containing myo-inositol and scyllo-inositol by reducing scyllo-inosose using a metal salt of boron hydride in a solution containing scyllo-inosose; a second step of dissolving a scyllo-inositol/boric acid complex in the liquid mixture by adding an acid to the liquid mixture and of adjusting the solution to be an acidic solution of 0.01 N or more; and a third step of allowing only scyllo-inositol to be precipitated by adding a water-soluble organic solvent to the acidic solution in such an amount that myo-inositol is not precipitated.

When scyllo-inosose is reduced using a metal salt of boron hydride in a solution containing the scyllo-inosose, boric acid and a metal ion exist as well as scyllo-inositol and myo-inositol which are generated by the reduction. Therefore, a part of the scyllo-inositol forms a water-insoluble scyllo-inositol/boric acid complex, to thereby reduce its yield when the scyllo-inositol is purified only from the solution component. An object of a second embodiment of the present invention is to precipitate and purify only scyllo-inositol from an acidic solution obtained by dissolving into an acid the scyllo-inositol/boric acid complex which has been generated in a small amount in a liquid mixture containing myo-inositol and scyllo-inositol obtained by the reduction of the scyllo-inosose.

In a first step, the "solution containing scyllo-inosose" includes, for example, a solution obtained by oxidizing myo-inositol using a microorganism in a medium or solution (JP-A-2003-102492). Scyllo-inosose obtained by the microbial oxidation may be used in a dissolved state after being purified, or a culture filtrate may also be used. The "solution containing scyllo-inosose" may further contain substances other than the scyllo-inosose, such as a culture filtrate. In addition, there may be used a scyllo-inosose obtained by dissolving a scyllo-inosose which has been prepared by oxidizing myo-inositol with a platinum catalyst.

The metal boron hydride to be used for the reduction is not particularly limited as long as it is a reducing agent capable of reducing scyllo-inosose into scyllo-inositol in an aqueous system and capable of releasing boron. Examples thereof include sodium borohydride, lithium borohydride, and potassium borohydride.

The reduction reaction of scyllo-inosose can be performed, for example, by adding a powder or solution of a reducing agent to a solution containing the scyllo-inosose dissolved at a concentration of 20% or less (w/v). The solution is preferably stirred at this time. The heat may generate owing to the reduction reaction, therefore the reaction solution is desirably controlled to have a temperature of 50° C. or lower in order to prevent decomposition of the generated inosose. Furthermore, a part of the reducing agent may be decomposed to generate a hydrogen gas. Therefore, an antifoaming agent or the like is preferably added to reduce foam formation of the hydrogen gas.

As described above, scyllo-inosose is reduced into scyllo-inositol and myo-inositol and the scyllo-inositol and myo-inositol exist in a solution in a mixed state. In this case, the scyllo-inositol starts to gradually crystallize when its concentration exceeds about 1.6% (w/v). Typically, reduction of 5% (w/v) of scyllo-inosose solution generates about 3% of myo-inositol and about 2% (w/v) of scyllo-inositol. In addition, when the solution is left at room temperature for several hours, about 0.4% (w/v) of an oversaturated portion of the scyllo-inosose starts to be crystallized. Furthermore, a liquid mixture composed of scyllo-inositol and myo-inositol which is obtained by the reduction of the scyllo-inosose also contains boric acid, therefore a part of the scyllo-inositol starts to from a scyllo-inositol/boric acid complex. In the production method according to the second embodiment of the present invention, the second step may be performed immediately after the first step, or the second step may be performed after being left for a while after the first step since the scyllo-inositol/boric acid complex is dissolved by an acid treatment.

In the second step, a "liquid mixture containing myo-inositol and scyllo-inositol" obtained in the first step is added with an acid to dissolve a scyllo-inositol/boric acid complex in the liquid mixture, and then the solution is adjusted to be an acidic solution of 0.01 N or more. In this case, a mineral acid such as hydrochloric acid, sulfuric acid, nitric acid, or phosphoric acid can be used as the acid. Hydrochloric acid or sulfuric acid is preferably used.

In the third step, the acidic solution obtained in the second step is added with a water-soluble organic solvent in such an amount that only scyllo-inositol is precipitated while myo-inositol is not precipitated. The aqueous organic solvent to be used at this time is not particularly limited as long as it is an organic solvent which enables the precipitation of scyllo-inositol and maintains the state where myo-inositol is dissolved. Ethanol, methanol, or 1-propanol is preferable.

The amount such that only scyllo-inositol is precipitated while myo-inositol is not precipitated means an amount of 0.2 to 0.4 times for ethanol, 0.2 to 0.8 times for methanol, or 0.2 to 0.4 times for 1-propanol as compared to the amount of the acidic solution. Preferably, the amount is 0.35 to 0.45 times for ethanol, 0.45 to 0.55 times for methanol, or 0.35 to 0.45 times for 1-propanol as compared to the amount of the acidic solution.

When a water-soluble organic solvent is mixed, if a mixture is a homogenous solution, it is not necessary to perform stirring, but if the mixture is a suspension, it is preferable to perform stirring. The temperature upon the mixing is not particularly limited as long as it is a temperature at which only scyllo-inositol is precipitated, however a temperature of −10° C. to 50° C. is preferable and a temperature of 4° C. to 35° C. is more preferable. The time of mixing is preferably 15 to 76 hours, more preferably 20 to 24 hours.

By adding a water-soluble organic solvent under such condition, only scyllo-inositol is precipitated. Thus precipitated scyllo-inositol can be extracted as a solid by means of filtration or a common solid-liquid separation operation such as centrifugal separation. The solid is composed of almost pure scyllo-inositol, however, it can be also obtained as a crystal by a method such as recrystallization if necessary. The precipitated scyllo-inositol may be further purified using an ion exchange resin or the like after being dissolved in water, to further increase its purity.

EXAMPLES

Hereinafter, the present invention will be specifically described by referring to examples.

Example 1

<Method of Producing Scyllo-inositol (Small Scale)>

3 L of a liquid medium containing 10.0% myo-inositol, 1.0% yeast extract, and 1.0% sucrose was adjusted to pH 7.0 with 1N NaOH, and the medium was dispensed in 100 ml aliquots into 30 pieces of 500 ml-volume baffled conical flasks, followed by sterilization using an autoclave. One platinum loop of a slant culture of *Acetobacter* sp. AB10281 strain (FERM BP-10119) was inoculated to each of the conical flasks, and the microorganism was cultured at 27° C. for 5 days in a rotary shaker. After the culture, 250 ml of water was added to each of the conical flasks, and the mixture was stirred for 1 hour in a rotary shaker to dissolve crystalline scyllo-inositol generated in the culture solution. The culture solution was collected and centrifuged (8,000 rpm 20 minutes), and the obtained supernatant was defined as a culture supernatant solution (10.2 L).

The culture supernatant solution was analyzed by high-performance liquid chromatography under the following conditions. The result revealed that 12.6 mg/ml (129 g, conversion rate 43%) of scyllo-inositol was generated in the culture supernatant solution. In the culture supernatant solution, 2.1 mg/ml of scyllo-inosose remained, while myo-inositol was not detected.

The analysis conditions of high-performance liquid chromatography are as follows.
Column: Wakosil 5NH$_2$ (4.6×250 mm)
Column temperature: 40° C.
Detector: RI DETECTOR ERC-7515A (ERMA CR.INC.)
Injection volume: 5 µl
Solvent: Acetonitrile-Water=4:1
Flow rate: 2 ml/min
Elution time: Scyllo-inosose; 11.6 minutes
Myo-inositol; 17.8 minutes
Scyllo-inositol; 18.2 minutes The above-described conversion rate of scyllo-inositol was calculated by the following equation.

Conversion rate (%)={(Number of moles of scyllo-inositol in culture supernatant)/(Number of moles of myo-inositol before culture)}×100

Next, the culture supernatant solution was passed through a column formed by connecting a column (inner diameter 5 cm, length 40 cm) filled with 500 ml of a strong acidic cation exchange resin, Duolite (registered trademark) C-20 (H$^+$ type) (manufactured by Sumitomo Chemical Co., Ltd.) with a column (inner diameter 5 cm, length 16 cm) filled with 200 ml of activated carbon, and then 500 ml of ion-exchanged water was passed through the column to wash it. The flow-through solution and the washing solution were then passed through a column (inner diameter 7 cm, length 40 cm) filled with 1,000 ml of a strong basic anion exchange resin, Duolite (registered trademark) A116 (OH$^-$ type) (manufactured by Sumitomo Chemical Co., Ltd.), and then 1,000 ml of ion-exchanged water was passed through the column to wash it. It was found that the obtained flow-through solution and the water-washing solution included few impurities other than the above-described scyllo-inositol.

The solution obtained above was concentrated to about 700 ml under reduced pressure, and 3-fold volume of ethanol was added thereto. Then, the mixture was allowed to stand at 5° C. overnight, and the resultant colorless crystals of pure scyllo-inositol were filtered and dried, to thereby yield 118 g of scyllo-inositol. The purification recovery yield was 92%, and the total recovery rate of scyllo-inositol from myo-inositol was 39%.

Example 2

<Method of Producing Scyllo-inositol (Large Scale)>

40 L of a liquid medium containing 10.0% myo-inositol, 1.0% yeast extract, and 1.0% sucrose was poured in a 50-L jar fermentor and adjusted to pH 7.0 with 1N NaOH, followed by sterilization using an autoclave. 400 ml of *Acetobacter* sp. AB10281 (FERM BP-10119), which had been cultured in a medium having the same composition (conical flask), was inoculated and cultured at 27° C. for 5 days at an aeration rate of 1 vvm and an agitation of 200 rpm. After the culture, 60 L of hot water (about 50° C.) was added to about 40 L of the collected culture solution, and the mixture was stirred for 1 hour to dissolve crystalline scyllo-inositol which had been present in the culture solution. The culture solution was subjected to continuous centrifugation (8,000 rpm) to remove the cells, and the resultant solution was defined as a solution from which the cultured microorganism had been removed (about 100 L).

The solution from which the cultured microorganism had been removed was analyzed by high-performance liquid chromatography. The result revealed that 16.8 mg/ml (1.68 kg, conversion rate 42%) of scyllo-inositol was generated in the solution from which the cultured microorganism had been removed. In the solution from which the cultured microorganism had been removed, 2.9 mg/ml of scyllo-inosose remained, while myo-inositol was not detected. The analysis condition for the high-performance liquid chromatography is the same as that of Example 1.

Next, 400 g of sodium hydroxide was added to 100 L of the obtained solution, and the mixture was heated with stirring at 98° C. for 1 hour. Subsequently, 560 g of sodium hydroxide, 1,340 g of boric acid, and 1,260 g of NaCl were added and dissolved while the mixture was hot. After the stirring was stopped, the heat of the solution was released, and the solution was allowed to stand until the temperature reached 23° C. (about 24 hours).

Next, the solution was filtered to isolate crystals of a scyllo-inositol/boric acid complex formed in the liquid, and the crystals were washed with water until they became white. The resultant crystals (about 3.9 kg) were taken out to another container, and 5.9 L of water and 1.95 L of 37% hydrochloric acid were added thereto, followed by stirring. 30 minutes later, to precipitate scyllo-inositol which was released from boric acid by such procedure, 9.4 L of methanol was added, and the mixture was further stirred for 1 hour.

Next, the solution was filtrated to isolate crystallized scyllo-inositol in the liquid, and the crystals were washed with 1 L of 50% methanol. The resultant fine powder crystals (about 1.8 kg) were taken out to another container, and 10 L of water was added thereto, followed by boiling with stirring for 1 hour. Thereafter, the solution was cooled to 20° C. with stirring and then filtered, to thereby yield fine crystals of scyllo-inositol. After drying, 1.35 kg of colorless crystal of pure scyllo-inositol was obtained. The purification recovery yield was 80%, while the total recovery rate of scyllo-inositol from myo-inositol was 34%.

Example 3

<Identification of Scyllo-inositol-producing Microorganisms Based on the Nucleotide Sequence of 16SrRNA>

The nucleotide sequences of 16SrRNA were analyzed for 4 microbial strains consisting of 3 natural isolated strains, AB10285, AB10286, and AB10287, each having an ability to convert myo-inositol into scyllo-inositol, and AB10281 obtained from AB10253, in accordance with the conventional method. More specifically, a genomic DNA was extracted from the cultured cells, and then corresponding DNA fragments were prepared by the PCR using primers that were designed so as to amplify about 1.6 kbp of 16SrRNA, followed by analysis of about 1.3 kbp of sequences (Hokkaido System Science Co., Ltd.). The results of the sequences were inquired against database to identify related species.

Table 2 shows the inquiry results, homologies, and conversion rates into scyllo-inositol in culturing the microorganisms in the same way as Example 1.

Identification of Microbial Strains by Analysis of 16SrRNA Nucleotide Sequence

TABLE 2

| Strain name | Name of identified microorganisms | Homology | Conversion rate |
|---|---|---|---|
| AB10281 | *Acetobacter cerevisiae*, *Acetobacter malorum* | 99.93% | 40.0% |
| AB10285 | *Acetobacter cerevisiae*, *Acetobacter malorum* | 99.78% | 4.5% |
| AB10286 | *Burkholderia andropogonis* | 98.12% | 2.6% |
| AB10287 | *Burkholderia andropogonis* | 98.04% | 1.4% |

The results revealed that 4 microbial strains each having an ability to convert myo-inositol into scyllo-inositol may be broadly divided into 2 groups. As the first group, AB10281 and AB10285 were identified as *Acetobacter cerevisiae* or *Acetobacter malorum*, while the second group, AB10286 and AB10287, were identified as *Burkholderia andropogonis*.

Example 4

<Isolation of NAD$^+$-independent Myo-inositol 2-dehydrogenase from *Acetobacter* sp. AB10253>

3 g of myo-inositol, 1 g of yeast extract (FNI205: manufactured by Lallemand BI), and 0.5 g of glucose were added to 500 ml-volume baffled conical flask and dissolved in water so that the mixture has a volume of 100 ml, and the solution was adjusted to pH 5.0, followed by sterilization using an autoclave. According to such procedures, 4 pieces of flasks of a medium were prepared. One platinum loop of *Acetobacter* sp. AB10253 from a slant was added to each medium, and the microorganism was precultured at 27° C. for 2 days using a rotary shaker.

Next, 1.2 kg of myo-inositol, 0.4 kg of yeast extract (FNI205: manufactured by Lallemand BI), and 0.2 kg of glucose were added to 50-L jar fermentor and dissolved in water so that the mixture has a volume of 40 L. The solution was adjusted to pH 5.0, followed by sterilization using an autoclave. About 400 ml of a microbial solution of the precultured *Acetobacter* sp. AB10253 was added thereto, and the microorganism was cultured at 27° C. for 3 days at an aeration rate of 1 vvm and an agitation of 200 rpm.

After the culture, the cells were obtained as precipitates using a continuous centrifugator. The obtained cells were resuspended in 2 L of water, and washed cells were obtained by centrifugation and suspended in 2 L of 20 mM Tris buffer (pH 7.0). Next, ultrasonic waves were applied to the suspension to disrupt the cells. The cell lysis solution was centrifuged to precipitate the disrupted cells, and the disrupted cells were obtained as precipitates. The precipitates were suspended by adding 500 ml of 20 mM Tris buffer (pH 7.0), 0.6% Triton X-100 (manufactured by Kodak), and enzymes were extracted at 15° C. for 3 hours. Thereafter, the suspension was centrifuged, and 420 ml of the supernatant (crude enzyme solution) was taken out.

420 ml of the crude enzyme solution was concentrated to 150 ml using an ultrafilter (MW 30,000 cut off), and the concentrated solution was passed through a 400 ml-DEAE Toyopearl column equilibrated with 20 mM Tris buffer (pH 7.0) to adsorb proteins. Next, a solution with a linear concentration gradient from 0 mM to 500 mM NaCl in 20 mM Tris buffer (pH 7.0) containing no surfactant (total volume 1.6 L) was passed through the protein-adsorbed column at a rate of 10 ml/min to elute the proteins. The eluate was fractionated into 40 ml fractions. Next, 600 ml of 20 mM Tris buffer (pH 7.0) containing no surfactant was passed through the column again for washing, and then a solution with a linear concentration gradient from 0 mM to 500 mM NaCl in 20 mM Tris buffer (pH 7.0) containing 0.1% Triton X-100 (total volume 1.6 L) was passed through the column at a rate of 10 ml/min to elute the proteins. The eluate was fractionated into 40 ml fractions.

The enzyme activity of each fraction was measured by a standard method: that is, the change in absorbance at 600 nm of 1 ml of a solution containing 50 μl of the protein solution, 100 mM phosphate buffer (pH 5.0), 5 mg of myo-inositol, and 0.4 mg of 2,4-dichloroindophenol (oxidized DCIP) was calculated into a reaction rate, and an activity to oxidize 1 μmol of myo-inositol per minute was defined as one unit.

The results revealed that the target enzyme was eluted in fractions of solutions containing 20 mM Tris buffer (pH 7.0)

containing 0.1% Triton X-100 and 100 to 170 mM NaCl. Next, those fractions (240 ml) were collected and concentrated to 30 ml using an ultrafilter (MW 30,000 cut off), and 100 ml of 20 mM Tris buffer (pH 7.0) containing 0.1% Triton X-100 was added thereto. The solution was further concentrated to 30 ml, and 70 ml of 20 mM Tris buffer (pH 7.0) was added to the concentrated solution for desalting.

Next, the thus-prepared enzyme solution was passed through 100 ml-hydroxyapatite column equilibrated with 20 mM Tris buffer (pH 7.0) containing 0.1% Triton X-100 to adsorb proteins. Subsequently, a solution with a linear concentration gradient from 0 mM to 500 mM phosphate buffer (pH 7.0) in Tris buffer (pH 7.0) containing 0.1% Triton X-100 (total volume 400 ml) was passed through the protein-adsorbed column at a rate of 3 ml/min to elute the proteins. The eluate was fractionated into each of 10 ml-fractions, and the enzyme activity of each fraction was measured.

The results revealed that the target enzyme was eluted in fractions of solutions containing 20 mM Tris buffer (pH 7.0) containing 0.1% Triton X-100 and 100 to 170 mM phosphate buffer. The thus-obtained enzyme solution was found to contain almost pure $NAD^+$-independent myo-inositol 2-dehydrogenase. Next, the fractions (40 ml) were collected and concentrated to 5 ml using an ultrafilter (MW 30,000 cut off), and 100 ml of 20 mM Tris buffer (pH 7.0) was added. The solution was further concentrated to 5 ml, followed by desalting.

The thus-prepared concentrated solution was again passed through 20 ml-DEAE Toyopearl column (manufactured by Tosoh Corporation) equilibrated with 20 mM Tris buffer (pH 7.0) containing 0.1% Triton X-100 to adsorb proteins. Next, a solution with a linear concentration gradient from 50 mM to 250 mM NaCl in 20 mM Tris buffer (pH 7.0) containing 0.1% Triton X-100 (total volume 160 ml) was passed through the protein-adsorbed column at a rate of 1 ml/min to elute the proteins. The eluate was fractionated into each of 4 ml-fractions. After the fractionation, the enzyme activity of each fraction was measured, and each fraction having the activity was subjected to SDS electrophoresis.

As a result, SDS electrophoresis revealed the bands of proteins that correlate with the enzyme activity of the target enzyme. Removal of bands of proteins derived from fractions having no activity revealed that the target enzyme was an enzyme containing at least proteins having molecular weights of about 76 k Dalton and about 46 k Dalton.

Meanwhile, the fractions having the enzyme activity had red color, and the UV spectrum pattern revealed that the fractions contained cytochrome C. Moreover, the content of the target protein and the absorbance of cytochrome C revealed that 1 mol of the target enzyme contains 1 mol of cytochrome C.

For measurement of the optimum pH, the enzyme activity was measured while changing a buffer and pH value. As the buffer, there were used 100 mM phosphate buffer (pH 3 to 8), 100 mM Tris buffer (pH 7 to 8), and 100 mM carbonate buffer (pH 8 to 11). The results revealed that the target enzyme has the maximum activity at pH 4.5 to 5.5. Moreover, in measuring standard enzyme activity (100 mM phosphate buffer (pH 5.0)), various heavy metal ions ($Sn^{2+}$, $Mn^{2+}$, $Mg^{2+}$, $Cu^{2+}$, Fe, $Zn^{2+}$, $Co^{2+}$, $Pb^{2+}$, $Ca^{2+}$, $Cd^{2+}$, and $Ni^{2+}$) were added, and it was revealed that the target enzyme is specifically inhibited by $Sn^{2+}$ ion. The enzyme activity was inhibited in the presence of 1 mM $Sn^{2+}$ ion to 1% or less of the activity in the absence of $Sn^{2+}$ ion.

Meanwhile, it was confirmed that the target enzyme is an enzyme extracted with Triton X-100 from a membrane fraction, and the extracted enzyme oxidizes myo-inositol in the presence of reduced DCIP, while no oxygen absorption occurs in the absence of reduced DCIP. The facts mean that the enzyme is coupled to the electron transport system of the cell membrane in a living body to deprive electrons from myo-inositol to generate scyllo-inositol.

The substrate specificity of the target enzyme was determined by measuring the enzyme activity in a solution containing various sugars instead of myo-inositol at a final concentration of 50 mM. Meanwhile, the Km value was measured by measuring the enzyme activity for each sugar to which this enzyme shows the activity while changing the concentration of the sugar. Moreover, the oxidization reaction products were analyzed by HPLC to determine what substances were generated. The measurement was performed under the following HPLC conditions: there were used Wakosil 5NH2 column Φ 4.6×250 mm (column temperature 40° C.) as a column, 80% acetonitrile as a mobile phase (flow rate 2 ml/min), and RI detector as a detector.

As a result, the target enzyme was found to react with D-chiro-inositol (relative activity 100%: Km=8.8 mM), muco-inositol (relative activity 68%: Km=14.5 mM), and myo-inositol (relative activity 53%: Km=20 mM) to convert them into D-chiro-1-inosose, L-chiro-2-inosose, and scyllo-inosose, respectively. The enzyme was found not to react with allo-inositol, scyllo-inositol, L-chiro-inositol, and glucose.

Example 5

<Conversion of Myo-inositol into Scyllo-inosose by $NAD^+$-independent Myo-inositol 2-Dehydrogenase>

In the same way as Example 4, purification was performed using a 40 L-jar fermentor, and 5 ml of an enzyme solution obtained by purification and desalting with a 100-ml hydroxyapatite column was defined as an enzyme solution, which was used in the following conversion reaction.

30 g of myo-inositol (166.7 mmol) and 15 ml of 1 M phosphate buffer (pH 5.0) were added to 400 ml-centrifuge tube, and the mixture was diluted to 300 ml with water to dissolve myo-inositol. 1 ml of an enzyme solution at 30° C., and 8 g of reduced DCIP (Na salt) was gradually added to the solution with stirring. After disappearance of the blue color derived from reduced DCIP, white insoluble matters generated with the disappearance of the blue color (oxidized DCIP) were precipitated by centrifugation, and the supernatant was transferred to a new 400 ml-centrifuge tube. Then, the solution was adjusted to pH 5.0 with 1N phosphoric acid, and 8 g of reduced DCIP (Na salt) was further added with stirring. The procedure was repeated 6 times to add a total of 48 g of reduced DCIP (Na salt), and at the time of the disappearance of the blue color, 3 g of reduced DCIP (Na salt) was finally added. The mixture was allowed to stand for 1 hour and centrifuged, and the supernatant was taken. Such procedures yielded 292 ml of the supernatant. The procedures took 8 hours.

Next, the resultant supernatant was passed through a column filled with 100 ml of a strong acidic ion exchange resin (Duolite C20, $H^+$ type) at a flow rate of 1.5 ml/min, and the resultant eluate was passed through a column filled with 150 ml of a weak base ion exchange resin (Duolite 368S, OH-type). Moreover, the resultant eluate was passed through a column filled with 50 ml of activated carbon. The resultant eluate was concentrated, to thereby yield 26.5 g (148.9 mmol) of white powder (yield 89%). The substance was analyzed by NMR and HPLC, and the substance was found to contain 99% scyllo-inositol and 1% myo-inositol.

Example 6

<Screening of *Acetobacter* sp. AB10253 from Mutants Based on NAD$^+$-independent Myo-inositol 2-dehydrogenase Activity>

5 ml of a liquid medium (pH 5.0) containing 1% yeast extract (manufactured by Difco Laboratories) and 0.5% glucose in a test tube was sterilized, and one platinum loop of *Acetobacter* sp. AB10253 from a slant was added thereto, followed by shaking culture at 27° C. for 16 hours. 2.5 ml of a culture solution was taken to a sterilized tube and centrifuged at 3,000×g to collect the cells. The supernatant was discarded, and the cells were resuspended in 2.5 ml of 200 mM phosphate buffer solution (pH 8.0), followed by centrifugation at 3,000×g to collect the cells. The supernatant was discarded, and the cells were resuspended in 2.5 ml of 200 mM phosphate buffer (pH 8.0). 2.0 ml of the suspension was poured into a sterilized 100 ml-conical flask, and 0.5 ml of 40% glucose solution and 7.5 ml of 200 mM phosphate buffer (pH 8.0) were added and mixed. To the mixture, 20 µl of ethyl methanesulfonate was added, and shaking culture was performed at 30° C. for 45 minutes. After the treatment, 1 ml of the mixture was taken out to a sterilized tube and centrifuged at 3,000×g to collect cells. The supernatant was discarded, and the cells were suspended in 2.5 ml of 200 mM phosphate buffer (pH 7.0), followed by centrifugation at 3,000×g to collect cells. The supernatant was discarded, and the cells were resuspended in 2.5 ml of 200 mM phosphate buffer (pH 7.0), to thereby yield a solution containing a mutation-treated microorganism.

Next, the mutation-treated *Acetobacter* sp. AB10253 was inoculated by spreading 0.12 ml of the solution containing the mutation-treated microorganism on an agar medium prepared by solidifying a sterilized medium (pH 5.0) containing 3% myo-inositol, 1% yeast extract (manufactured by Difco Laboratories), 0.5% glucose, and 1.5% agar in 9-cm dish, and culture was performed at 27° C. for 2 days. Those procedures reduced the viable count to about 1.6%. Meanwhile, about 95 to 125 colonies were formed per dish.

After the culture, over the colonies formed in the 9-cm dish, 10 ml of a viscous solution was slowly poured, which had been prepared by sterilizing with filtration a solution having a composition of 100 mM phosphate buffer, 1% myo-inositol, and 0.4% oxidized DCIP and adding thereto equal volume of 1% agar solution sterilized with an autoclave while it was hot, followed by cooling to 36° C. so as to inhibit solidification of the agar. The agar medium that had been subjected to such treatments was slowly cooled at 27° C. to be solidified and layered over the colonies formed in the 9-cm dish.

After the treatment, the dish was incubated at 27° C., and then it was observed that the blue color of oxidized DCIP that had spread all over the agar medium gradually began to become transparent only around the colonies depending on the degree of the NAD$^+$-independent myo-inositol 2-dehydrogenase activity. At that time, the colonies at the position where the color more rapidly became transparent were scratched by a sterilized needle and subcultured in a fresh medium. All of the 2,154 colonies were subjected to a primary selection, to thereby obtain 22 strains having high NAD$^+$-independent myo-inositol 2-dehydrogenase activity.

Next, for the secondary selection, the thus-obtained 22 strains of bacteria that formed colonies were individually inoculated to 5 ml of a sterilized liquid medium (pH 5.0) containing 3% myo-inositol, 1% yeast extract (manufactured by Difco Laboratories), and 0.5% glucose in a test tube. Shaking culture was performed at 27° C. for 3 days, and then 1 ml of the culture solution was taken out to a test tube, followed by centrifugation at 3,000×g to collect the cells. The supernatant was discarded, and 1 ml of a solution containing 10% myo-inositol, 50 mM phosphate buffer (pH 5.0) was added to the test tube containing the cells, followed by shaking culture at 27° C. for 4 hours. Then, centrifugation was performed at 16,000×g, and the conversion rate of myo-inositol into scyllo-inosose in the supernatant was measured by HPLC. On the other hand, 0.5 ml of the culture solution (5 ml) was taken out into a sterilized tube and centrifuged at 3,000× g, and the supernatant was discarded. The cells obtained as precipitates were washed with water, and the NAD$^+$-independent myo-inositol 2-dehydrogenase activity was measured.

As a result, in 3 strains (strain No. E6-55, H2-68, and B7-14) among the 22 mutant strains, the NAD$^+$-independent myo-inositol 2-dehydrogenase activity increased 1.3-fold or more after the mutation, and the activity increased 1.6-fold, 2.2-fold, and 2.8-fold, respectively. Meanwhile, the conversion rate of myo-inositol into scyllo-inosose increased 1.1-fold, 1.4-fold, and 1.5-fold, respectively, and the conversion rate of myo-inositol into scyllo-inosose of the strains having 1.3-fold or less NAD$^+$-independent myo-inositol 2-dehydrogenase activity was equal to that of the microorganism before mutation. The results revealed that screening based on the NAD$^+$-independent myo-inositol 2-dehydrogenase activity correlates with increase in the conversion rate of myo-inositol into scyllo-inosose.

Example 7

<Production of Scyllo-inosose by Conversion of Myo-inositol into Scyllo-inosose Using the Mutant Strain (B7-14)>

10 g of myo-inositol, 1 g of yeast extract (FNI205: manufactured by Lallemand BI), and 0.5 g of glucose were added to a 500 ml-volume baffled conical flask and dissolved in water so that the mixture has a volume of 100 ml, and the solution was adjusted to pH 5.0, followed by sterilization using an autoclave. According to such procedures, 20 flasks of a medium (corresponding to 2 L: myo-inositol 200 g (1.11 mmol)) were prepared. One platinum loop of the mutant strain (B7-14) from a slant was added to each medium, and the bacterium was cultured at 27° C. for 3 days using a rotary shaker.

After the culture, the culture solution was centrifuged, and the resultant supernatant was passed through a column filled with 500 ml of a strong acidic ion exchange resin (Duolite C20, H$^+$ type) at a flow rate of 10 ml/min. The obtained eluate was passed through a column filled with 900 ml of a weak base ion exchange resin (Duolite 368S, OH$^-$ type), and the resultant eluate was further passed through a column filled with 50 ml of activated carbon. The resultant eluate was concentrated, to thereby yield 162 g (0.91 mol) of white powder (yield 82%). The substance was analyzed by NMR and HPLC, and it was found that the substance contained 91% of scyllo-inosose, 3% of myo-inositol, and 6% of scyllo-inositol (scyllo-inosose of purity of 91%).

Example 8

<Production of Scyllo-inositol by Conversion and Chemical Reduction of Myo-inositol into Scyllo-inosose Using the Mutant Strain (B7-14)>

10 g of myo-inositol, 1 g of yeast extract (FNI205: manufactured by Lallemand BI), and 0.5 g of glucose were added to a 500 ml-volume baffled conical flask and dissolved in water so that the mixture has a volume of 100 ml, and the solution was adjusted to pH 5.0, followed by sterilization using an autoclave. According to such procedures, 20 flasks of a medium (corresponding to 2 L: myo-inositol 200 g (1.11 mmol)) were prepared. One platinum loop of the mutant strain (B7-14) from a slant was added to each medium, and the bacterium was cultured at 27° C. for 3 days using a rotary shaker.

After the culture, the culture solution was centrifuged at 8,000×g, and about 2 L of the resultant supernatant was adjusted to pH 7.5 with 5N NaOH solution. 9.2 g of $NaBH_4$ was added to the solution with stirring to perform a reduction reaction. The temperature of the reaction solution was raised to 37° C. by the reaction heat. 30 minutes later, insoluble matter gradually appeared, and 1.2 L of water was added thereto to dissolve almost all of the generated insoluble matter. The solution was filtered to remove the insoluble matter, and the filtrate was passed through a column filled with 500 ml of a strong acidic ion exchange resin (Duolite C20, $H^+$ type) at a flow rate of 10 ml/min. The resultant eluate was passed through a column filled with 900 ml of a strong base ion exchange resin (Duolite A116, $OH^-$ type), and the resultant eluate was further passed through a column filled with 300 ml of activated carbon. The resultant eluate was concentrated, to thereby yield 145 g of white powder. The substance was analyzed by HPLC, and it was found that the substance contained 36% of scyllo-inositol and 64% of myo-inositol.

The resultant white powder was suspended in water so as to have a volume of 470 ml, and the suspension was heated to 70° C. to thoroughly dissolve myo-inositol. The suspension was cooled to 30° C. with stirring, and the white solution was filtered to collect the insoluble matter. The insoluble matter was washed with a small amount of water and dried, to thereby yield 44.2 g of powder. The substance was analyzed by HPLC, and it was found that the substance contained 98% of scyllo-inositol and 2% of myo-inositol. Furthermore, 700 ml of water was added to the resultant powder, and the mixture was heated to 85° C. to dissolve all of them. The mixture was gradually cooled to 30° C. with stirring, and 700 ml of ethanol was added thereto. The mixture was allowed to stand overnight at room temperature, and then the resultant crystals were collected by filtration and dried, to thereby yield 40.1 g (222.8 mmol) of crystals (yield 20%). The crystals were analyzed by NMR and HPLC, and it was found that the obtained substance was scyllo-inositol having a purity of 99.9% or more.

Example 9

<Purification of Scyllo-inositol Dehydrogenase Produced by *Acetobacter* sp. AB10281 FERM BP-10119>

3 L of a liquid medium containing 10.0% of myo-inositol, 1.0% of yeast extract, and 1.0% of sucrose was adjusted to pH 7.0 with 1N NaOH, and the medium was dispensed in 100 ml aliquots into 30 pieces of 500 ml-volume baffled conical flasks, followed by sterilization using an autoclave. One platinum loop of a slant culture of *Acetobacter* sp. AB10281 FERM BP-10119 was inoculated to each conical flask, and the microorganism was cultured at 27° C. for 5 days using a rotary shaker (180 rpm). After the culture, 250 ml of water was added to each conical flask, and the mixture was stirred for 1 hour using a rotary shaker to dissolve crystalline scyllo-inositol that had been present in the culture solution. The culture solution was collected and centrifuged (8,000 rpm, 20 minutes), to thereby yield cells (wet weight 75 g).

The cells were suspended in 300 ml of water and were disrupted by ultrasonic wave at 10° C. or less. The lysis solution indicated pH 4.8, and the solution was adjusted to pH 7.0 with 1N NaOH. Then, the solution was centrifuged (16,000 rpm, 20 minutes) to separate the supernatant. Next, $MgSO_4$ was added so that the supernatant contains 2 mM $Mg^{2+}$, and the solution was charged onto a Blue-Toyopearl column (manufactured by Tosoh Corporation: 20 ml). Then, 50 ml of 20 mM Tris buffer (pH 7.0) supplemented with 2 mM $Mg^{2+}$ was passed through the column to wash it. Thereafter, 50 ml of 20 mM Tris buffer (pH 7.0) supplemented with 1 M KCl was passed through the column to elute adsorbed proteins. Next, the eluate was concentrated using an ultrafilter (MW 30,000 cut off), and 50 ml of 20 mM Tris buffer (pH 7.0) was added to the concentrated solution, followed by concentration again, to thereby yield a desalted concentrated solution. Subsequently, the desalted concentrated solution was charged onto a DEAE Toyopearl column (Tosoh Corporation: 20 ml), and elution was performed with a solution with a linear concentration gradient from 0 mM to 500 mM NaCl in 20 mM Tris buffer (pH 7.0). Then, the eluate was fractionated into fractions. The scyllo-inositol dehydrogenase activity of each of the fractionated solutions was measured, and three fractions, an unadsorbed fraction (SIDH1), a fraction eluted with 200 mM NaCl (SIDH2), and a fraction eluted with 300 mM (SIDH3), were found to have the activity.

The activity was measured as follows: 5 µl of a reaction solution (200 mM Tris buffer (pH 8.0), 2% of NADPH, and 1% of scyllo-inosose) and 5 µl of an enzyme solution were mixed and allowed to react at 36° C. for 30 minutes, and then 500 µl of water was immediately added, followed by measurement of the absorbance at 340 nm. The decrease in the absorbance at 340 nm was measured based on a blank value for a test solution obtained by using water instead of the enzyme solution. The enzyme solution was diluted as required.

The above-described column-unadsorbed fraction was further charged onto a CM Toyopearl column (Tosoh Corporation: 20 ml), and elution was performed with a solution with a linear concentration gradient from 0 mM to 500 mM NaCl in 20 mM Tris buffer (pH 7.0). Then, the eluate was fractionated into fractions. The scyllo-inositol dehydrogenase activity in each of the fractionated solutions was measured, and the unadsorbed fraction was found to have the activity. The fraction eluted with 200 mM NaCl and the fraction eluted with 300 mM were separately desalted with an ultrafilter again, and elution was performed with a solution with a linear concentration gradient from 200 mM to 300 mM NaCl in 20 mM Tris buffer (pH 7.0). Then, the eluate was fractionated into fractions and purified. Then, those three enzyme solutions having the scyllo-inositol dehydrogenase activity were separately concentrated using an ultrafilter, and the concentrated solutions were charged onto a gel filtration column (Tosoh Corporation: 2000 SWXL), respectively. Then, the eluates were purified with 20 mM phosphate buffer (pH 7.0) supplemented with 200 mM NaCl. The thus-purified enzyme solutions were subjected to slab-gel SDS electrophoresis, and the gel after the electrophoresis was stained with a Coomassie brilliant blue staining solution (Rapid CBB KANTO: manufactured by Kanto Chemical Co., Inc.), and then it was decolored. The purity of the bands of interest was measured by measuring the blue bands of proteins using a densitometer (manufactured by ATTO Corporation), and it was found that purity of each fraction was 85% or more.

Example 10

<Purification of the Enzyme of the Present Invention Produced by *Escherichia coli* K12 ATCC10798 and Analysis of its N-terminal>

3 L of LB broth medium (1% Bacto-tryptone, 0.5% yeast extract, 1% NaCl, pH 7.0) containing 0.5% L-sorbose was dispensed in 100 ml aliquots into 30 pieces of 500-ml Sakaguchi flasks, followed by sterilization using an autoclave. One platinum loop of a slant culture of *Escherichia coli* K12 was inoculated to each conical flask, and the microorganism was cultured at 36° C. for 1 day using a recipro shaker (135 rpm). After the culture, the culture media were collected and centrifuged (8,000 rpm, 20 minutes), to thereby yield cells (wet weight 32 g). The cells were suspended in 100 ml of water and were disrupted by ultrasonic waves at 10° C. or less. The lysis solution indicated pH 6.8, and the solution was adjusted to pH 7.0 with 1N NaOH solution and then centrifuged (16,000 rpm, 20 minutes) to separate the supernatant. Next, $MgSO_4$ was added so that the supernatant contains 2 mM $Mg^{2+}$, and the solution was charged onto a Blue-Toyopearl column (Tosoh Corporation: 20 ml). Then, 50 ml of 20 mM Tris buffer (pH 7.0) supplemented with 2 mM $Mg^{2+}$ was passed through the column to wash it. Subsequently, 50 ml of 20 mM Tris buffer (pH 7.0) supplemented with 1 M KCl was passed through the column to elute adsorbed proteins. Next, the eluate was concentrated using an ultrafilter (MW 30,000 cut off), and 50 ml of 20 mM Tris buffer (pH 7.0) was added to the concentrated solution, followed by concentration again, to thereby yield a desalted concentrated solution. Next, the desalted concentrated solution was charged onto a DEAE Toyopearl column (Tosoh Corporation: 20 ml), and elution was performed with a solution with a linear concentration gradient from 0 mM to 500 mM NaCl in 20 mM Tris buffer (pH 7.0). The eluate was fractionated into fractions. The scyllo-inositol dehydrogenase activity of each of the fractionated solutions was measured, and it was found that the fraction eluted with 300 mM had the activity.

The activity measurement was performed in the same way as in the above Example 9, and the decrease in the absorbance at 340 nm was measured. The enzyme solution was diluted as required.

The fraction eluted with 300 mM NaCl was desalted using an ultrafilter again, and the resultant was charged onto a DEAE Toyopearl column (Tosoh Corporation: 20 ml). Then, elution was performed with a solution with a linear concentration gradient from 250 mM to 350 mM NaCl in 20 mM Tris buffer (pH 7.0), and purification was performed by repeating the operation of fractionating the eluate three times to remove contaminant proteins. Furthermore, the enzyme solution having the scyllo-inositol dehydrogenase activity was concentrated using an ultrafilter, and the concentrated solution was charged onto a gel filtration column (Tosoh Corporation: 2000 SWXL). The eluate was purified with 20 mM phosphate buffer (pH 7.0) supplemented with 200 mM NaCl.

The thus-purified enzyme solution was subjected to slab-gel SDS electrophoresis, and then the gel was taken out, and the proteins were transferred to a PVDF membrane (Immobilon PSQ: manufactured by Millipore Corporation) having the same size as that of the gel using a semidry electroplotter (manufactured by Funakoshi Co., Ltd.). Then, the PVDF membrane was taken out and stained with a Coomassie brilliant blue staining solution (Rapid CBB KANTO: manufactured by Kanto Chemical Co., Inc.), and then it was decolored. The purity was measured using a densitometer in the same way as Example 9, and the purity was 40%. Moreover, the portion corresponding to the target protein was cut off to remove unwanted proteins present around the portion, to thereby yield an enzyme of the present invention having a high purity.

Next, the enzyme of the present invention having a high purity which exists on the PVDF membrane was analyzed using an N-terminal amino acid analyzer (Hewlett-Packard Company). As a result, a sequence of serine-aspartic acid-asparagine-isoleucine-arginine was detected. DNA encoding a protein having such a sequence was searched from the database on the entire sequence of *Escherichia coli* (database name "Colibri"), and the ydgJ gene (or b1624 gene) was matched. The gene product of the ydgj gene had been predicted as one of oxidoreductases, but its substrate and product were unknown.

Example 11

<Isolation and Expression of the DNA of the Present Invention Derived from *Escherichia coli* K12 ATCC10798>

To obtain the ydgj gene that was assumed to encode the enzyme of the present invention, first, the entire genome of *Escherichia coli* K12 to be used as templates was extracted as follows. One platinum loop of *Escherichia coli* K12, which had been cultured in LB slant medium (1% bacto-tryptone, 0.5% yeast extract, 1% NaCl, pH 7.0, 1.5% agar), was inoculated to 100 ml of LB flask medium (1% bacto-tryptone, 0.5% yeast extract, 1% NaCl, pH 7.0) and aerobically cultured for 8 hours at 36° C., followed by collection of cells. To the pellet of the cells were added 15 ml of Saline-EDTA solution (0.15 M NaCl, 0.1 M EDTA, pH 8.0) and 50 mg of lysozyme, and the cells were suspended, followed by reaction at 37° C. for 2 hours. After the treatment, 0.5 ml of 25% SDS solution was added to the solution to completely lyse the cells, and 3 ml of phenol was added to denatured proteins, followed by centrifugation. The supernatant was taken out, and 20 ml of 2-propanol was added to the solution to yield crude genomic DNA. The yielded crude genomic DNA was precipitated by centrifugation, and the supernatant was removed, followed by drying under reduced pressure. The dried crude genomic DNA was further dissolved in 3 ml of TE solution (10 mM Tris-HCl, 1 mM EDTA, pH 8.0), and then 0.01 mg of RNase was added, followed by reaction at 36° C. for 2 hours to degrade RNA. Then, 0.01 mg of proteinase K was added, and the mixture was allowed to react at 36° C. for 2 hours to degrade proteins. Next, 1 ml of phenol-chloroform mixed solution (1:1) was added, and the mixture was slowly stirred to denature RNAase and proteinase K. The mixture was separated into two phases by centrifugation, and the upper layer (an aqueous phase) was taken out and was adjusted to pH 5.2 by adding 0.3 ml of 3 M sodium acetate solution. To the solution was added with 3 ml of 2-propanol to yield genomic DNA. The obtained genomic DNA was precipitated by centrifugation, and the supernatant was removed, followed by drying under reduced pressure. The dried genomic DNA was dissolved in 3 ml of TE solution, and the process from the operation of adding 1 ml of the phenol-chloroform mixed solution (1:1) to the operation of dissolving DNA in 3 ml of the TE solution was repeated again, followed by centrifugation. In the same way as above, equal volume of 2-propanol was added to the supernatant at pH 5.2, to thereby prepare a solution of genomic DNA of *Escherichia coli* K12. The thus-obtained genomic DNA was used as a template DNA solution for PCR.

A fragment that is derived from *Escherichia coli* K12 and contains a ribosome binding site (RBS) of the ydgJ gene was cloned, and PCR was performed using primers having the following sequences to express the gene as a recombinant enzyme.

```
SEQ ID No. 15:
ydgj-F      5'-cattcaagcttaatgagaggcaatgacatgagc
            g-3'

SEQ ID No. 16:
ydgj-R      5'-tcggaattcttcatgcaaggcacaaagtcgc-
            3'
```

For PCR, Ex taq reaction solution from Takara Shuzo Co., Ltd. was used, and a solution having a composition of 5 µl of 10× Takara ExTaq Buffer, 4 µl of dNTP mixture, 30 ng of the template DNA, 1 µl of 10 µM primer solution, and 0.5 µl of Takara ExTaq was prepared by adding water so that it has a volume of 50 µl, followed by layering 30 µl of mineral oil. For the reaction, a cycle of the three steps: denaturation (94° C., 30 seconds), annealing (55° C., 1 minute), and elongation (72° C., 1 minute), were repeated 35 times using PCR Amplifier (ASTEC Co., Ltd., PC-700). The above-described PCR amplified a DNA fragment having a size of about 1.0 kbp. After the reaction, the layered mineral oil was extracted with 0.3 ml of hexane, and the hexane layer was removed. This procedure was repeated three times, followed by reduction of the pressure for one minute, to thereby remove the mineral oil. From 50 µl of the thus-obtained reaction solution, PCR fragment was purified using GENECLEAN (Bio101). Specifically, 300 µl of NaI solution included in the kit was added and mixed, and 10 µl of glass beads solution was added and mixed. The mixture was allowed to stand at 4° C. for 15 minutes and centrifuged to precipitate glass beads to which the DNA fragment was adsorbed, and the supernatant was removed. 500 µl of New wash solution included in the kit was further added to suspend the glass beads, and the mixture was centrifuged to remove the supernatant. The washing operation using the New wash solution was repeated three times. Next, the glass beads were dried under reduced pressure, and after the drying, 15 µl of sterilized water was added to suspend them. The mixture was heated to 55° C. for 15 minutes and centrifuged, to thereby yield 12 µl of a supernatant containing the DNA fragment.

An operation of inserting the purified DNA fragment into an expression vector was performed as follows. Specifically, 0.5 µg of an expression plasmid (pUC119: manufactured by Takara Shuzo Co., Ltd.)), 1 µl of restriction enzymes HindIII and EcoRI from Takara Shuzo Co., Ltd., and 2 µl of 10× K buffer, which is a restriction enzyme buffer from Takara Shuzo Co., Ltd., were added to 10 µl of the DNA fragment solution, and sterilized water was added so that the mixture has a volume of 20 µl, followed by mixing. The reaction solution was allowed to react at 36° C. for 2 hours. After the reaction of the restriction enzymes, the DNA fragment and expression vector were isolated with GENECLEAN and ligated with each other. Specifically, 300 µl of the NaI solution included in the kit was added to and mixed in 20 µl of the restriction enzyme reaction solution, and 10 µl of the glass beads solution was added thereto and mixed. The mixture was allowed to stand at 4° C. for 15 minutes and then centrifuged to precipitate glass beads to which the DNA fragment and expression vector were adsorbed, and the supernatant was removed. Then, 500 µl of the New wash solution included in the kit was added to suspend the glass beads, and the suspension was centrifuged to remove the supernatant. The washing operation using the New wash solution was repeated three times. Next, the glass beads were dried under reduced pressure, and after the drying, 15 µl of sterilized water was added to suspend them. The mixture was heated to 55° C. for 15 minutes and centrifuged, to thereby yield 12 µl of a supernatant containing the DNA fragment and expression vector. The procedure removed small DNA fragments that have size of about 50 bp or less and were generated by the-restriction enzymes, to thereby yield the DNA fragment of interest and expression vector.

10 µl of Takara Ligation kit-I solution (Takara Shuzo Co., Ltd.) was added to the 10 µl of the thus-prepared solution, and the mixture was allowed to react at 16° C. for 1 hour. The solution was used to transform the competent cells (Takara Shuzo Co., Ltd.: DH5α). Specifically, 5 µl of a ligation reaction solution was added thereto and mixed in 60 µl of a competent cell solution unfreezed at 4° C., and left at 0° C. for 30 minutes, and then at 42° C. for 45 seconds and 0° C. for 2 minutes. 500 µl of SOC solution (2% bacto-tryptone, 0.5% yeast extract, 10 mM NaCl, 20 mM glucose, 10 mM MgSO$_4$, and 10 mM MgCl$_2$) was added thereto, followed by recovery culture at 36° C. for 1 hour. 100 µl of the culture solution was applied on LB agar medium (1% bacto-tryptone, 0.5% yeast extract, 1% NaCl, pH 7.0, 1.5% agar) containing 50 µg/ml ampicillin, 40 µg/ml X-gal (5-Bromo4-Chloro-3-Indolyl-β-D-Galactoside), and 1 mM IPTG (thiogalactopyranoside). Culture was further performed at 37° C. for 16 hours. The culture yielded *Escherichia coli* transformed by introducing the above-described plasmid as white colonies, and the colonies were selected. The thus-separated colonies of the transformed *Escherichia coli* were cultured in LB liquid medium containing ampicillin (50 µg/ml). From the cultured cells of the transformed *Escherichia coli*, a plasmid DNA was separated and purified using a plasmid purification kit (QIA filter Plasmid Midi Kit, QIAGEN). The thus-obtained plasmid DNA was confirmed to have a DNA fragment having a size of about 1.0 kbp, which corresponds to the ydgj gene of interest.

Next, to confirm the scyllo-inositol dehydrogenase activity, the microbial strains isolated as colonies were transferred to 100 ml of LB medium (1% bacto-tryptone, 0.5% yeast extract, 1% NaCl, pH 7.0) containing 50 µg/ml ampicillin, and they were cultured at 36° C. for 7 hours. 0.3 ml of 200 mM thiogalactopyranoside solution was added to the culture solution, and the cells were further cultured at 36° C. for 3 hours. After completion of the culture, the cells were collected by centrifugation and washed with physiological saline once. Then, the washed cells were suspended in 3 ml of 0.6% Triton X-100 solution, and the cells were disrupted by ultrasonic wave at 4° C. The solution was centrifuged, and 2.8 ml of the supernatant (enzyme solution) was taken out. 1.2 g of ammonium sulfate was added to the supernatant to salt out proteins at 4° C. The salted-out proteins were collected by centrifugation (15,000 rpm, 20 min), and the supernatant was removed. The precipitates were dissolved in 2.5 ml of 20 mM Tris buffer (pH 7.0), and the solution was centrifuged (15,000 rpm, 20 min) again. The supernatant was applied onto Sephadex G-25 column (Pharmacia K.K.: 14 ml) equilibrated with 20 mM Tris buffer (pH 7.0). Elution was performed with 20 mM Tris buffer (pH 7.0), and the eluate was desalted. The procedures yielded 3.5 ml of a crude enzyme solution of ydgJ gene product.

The scyllo-inositol dehydrogenase activity was measured as follows: 5 µl of a reaction solution (200 mM Tris buffer (pH 8.0), 2% of NADPH, and 1% of scyllo-inosose) and 5 µl of an enzyme solution were mixed and allowed to react at 36° C. for 30 minutes, and then 500 μl of water was immediately added, followed by measurement of the absorbance at 340 nm. The decrease in the absorbance at 340 nm was measured based on a blank value for a test solution obtained by using water instead of the enzyme solution. The enzyme solution was diluted as required.

Meanwhile, the enzyme reaction product was measured as follows: 10 mg of scyllo-inosose, 40 mg of NADPH, and 10 U of the enzyme were allowed to react in 1.0 ml of 100 mM Tris buffer (pH 8.0) at 36° C. for 4 hours, and a heat treatment was performed at 80° C. for 10 min, followed by cooling. Then, 100 μl of a strong base cation exchange resin, 100 μl of a strong acid anion exchange resin, and 10 mg of activated carbon were added, and the mixture was stirred and centrifuged. Then, the supernatant was diluted 2-fold, and measurement was performed by HPLC (Shodex Asahipak NH2P-50 4E Φ4.6×250 mm: Shodex) using an RI detector under the condition of a column temperature of 40° C. and a mobile phase flow rate of 1.5 ml (80% acetonitrile). As a result, the ydgJ gene product was found to have a high scyllo-inositol dehydrogenase activity, and 100% of the product was scyllo-inositol obtained by reduction, while myo-inositol that is an isomer thereof was not detected. As a result, the solution of a recombinant enzyme derived from the ydgJ gene was found to have a high scyllo-inositol dehydrogenase activity, and the gene product was scyllo-inositol dehydrogenase. Meanwhile, in the product obtained by the reduction reaction of scyllo-inosose, only scyllo-inositol was detected, and the enzyme was found to stereospecifically reduce scyllo-inosose into scyllo-inositol. Meanwhile, the sequence of the ydgJ gene is shown in SEQ ID NO: 1, and the amino acid sequence corresponding thereto is shown in SEQ ID NO: 2.

Example 12

<Isolation and Expression of a Homologous DNA Estimated from Homology with *Escherichia coli* ydgj Gene, and Properties thereof>

From estimation of the three-dimensional structure of the ydgJ gene product of *Escherichia coli* based on the amino acid sequence, the product was estimated to belong to the family of glucose-fructose oxidoreductases. The family also includes myo-inositol 2-dehydrogenase (EC 1.1.1.18), and the sequence involved in a NAD binding in the amino acid sequence was found to have high homology. Moreover, identification of the amino acid sequence of a site involved in the substrate binding by X-ray structure analysis of glucose-fructose oxidoreductase and search of proteins that have partially the same amino acid sequence and are homologous with the ydgJ gene product revealed that there are homologous proteins in many gram-negative bacteria and gram-positive bacteria.

From those bacteria, homologous DNAs were searched based on the homology of the ydgJ gene of *Escherichia coli*. As a result, the ydgj gene of *Escherichia coli* was found to have homology with Atu4375 gene and Atu3234 gene in genome of *Agrobacterium tumefacience* C58 ATCC33970, BG14057 gene in genome of *Bacillus subtilis* 168 ATCC23857, Xcc3438 gene in genome of *Xanthomonas campestris pv. campestris* ATCC33913, and Atu4375 gene and Atu3234 gene in genome of *Agrobacterium* sp. AB10121 FERM P-17383 that is known as a microorganism having an ability to directly convert myo-inositol into scyllo-inositol. Therefore, those DNAs were isolated and expressed.

To obtain the above-described candidate DNAs, the total genomes of *Agrobacterium tumefacience* C58 ATCC33970, *Bacillus subtilis* 168 ATCC23857, *Xanthomonas campestris pv. campestris* ATCC33913, and *Agrobacterium* sp. AB10121 FERM P-17383 to be used as templates were extracted as follows. For *Agrobacterium tumefacience* C58, *Xanthomonas campestris pv. campestris*, and *Agrobacterium* sp. AB10121, one platinum loop of each of *Agrobacterium tumefacience* C58, *Xanthomonas campestris pv. campestris*, and *Agrobacterium* sp. AB10121 that had been cultured in LB slant medium (1% bacto-tryptone, 0.5% yeast extract, 1% NaCl, pH 7.0, 1.5% agar) was inoculated in 100 ml of an LB flask medium (1% bacto-tryptone, 0.5% yeast extract, 1% NaCl, pH 7.0) and aerobically cultured for 18 hours at 27° C. and collected. 15 ml of Saline-EDTA solution (0.15 M NaCl, 0.1 M EDTA, pH 8.0) and 50 mg of lysozyme were added to the cell pellets to suspend it, followed by reaction at 37° C. for 2 hours. After the treatment, 0.5 ml of 25% SDS solution was added to the solution to completely lyse the cells, and 3 ml of phenol was added to denature proteins. Thereafter, the solution was centrifuged, and the supernatant was taken out. 20 ml of 2-propanol was added to the solution to yield crude genomic DNA. The yielded crude genomic DNA was precipitated by centrifugation, and the supernatant was removed, followed by drying under reduced pressure. Thereafter, dried crude genomic DNA was further dissolved in 3 ml of TE solution (10 mM Tris-HCl, 1 mM EDTA, pH 8.0), and then 0.01 mg of RNAase was added thereto and allowed to react at 36° C. for 2 hours to degrade RNA. Moreover, 0.01 mg of proteinase K was added and allowed to react at 36° C. for 2 hours to degrade proteins. Next, 1 ml of phenol-chloroform mixed solution (1:1) was added, and the mixture was slowly stirred to denature RNAase and proteinase K. The mixture was separated into two phases by centrifugation, and the upper layer (aqueous phase) was taken out and was adjusted to pH 5.2 by adding 0.3 ml of 3 M sodium acetate solution. 3 ml of 2-propanol was added to the solution to yield genomic DNA. The obtained genomic DNA was precipitated by centrifugation, and the supernatant was removed, followed by drying under reduced pressure. The dried genomic DNA was dissolved in 3 ml of TE solution, and the process from the operation of adding 1 ml of the phenol-chloroform mixed solution (1:1) to the operation of dissolving DNA in 3 ml of the TE solution was repeated again, followed by centrifugation. Then, in the same way as above, equal volume of 2-propanol were added to the supernatant at pH 5.2, to thereby prepare solutions of genomic DNAs of *Agrobacterium tumefacience* C58, *Xanthomonas campestris pv. campestris*, and *Agrobacterium* sp. AB10121, respectively. The thus-obtained genomic DNAs were used as template DNA solutions for PCR.

One platinum loop of *Bacillus subtilis* 168 ATCC23857 that had been cultured in an LB slant medium (1% bacto-tryptone, a 0.5% yeast extract, 1% NaCl, pH 7.0, 1.5% agar) was inoculated in 100 ml of LB flask medium (1% bacto-tryptone, 0.5% yeast extract, 1% NaCl, pH 7.0) and aerobically cultured at 36° C. for 18 hours. Then, 1 ml of the medium was added to 100 ml of an LB flask medium prepared as above, and the microorganisms were cultured for 4 hours, followed by collection. After the collection, the total genome was extracted in the same manner as the method used for *Agrobacterium*.

Next, PCR was performed using primers having the following sequences for cloning of Atu4375 gene and Atu3234 gene in the genome of *Agrobacterium tumefacience* C58, Atu4375 gene and Atu3234 gene in the genome of *Agrobacterium* sp. AB10121, and Xcc3438 gene in the genome of *Xanthomonas campestris pv. campestris* (all including RBS), for expressing them as recombinant enzymes.

SEQ ID No. 17:
Atu4375-F    5'-ggcggatcctttgaaagggatagtcatgtcct-3'

SEQ ID No. 18:
Atu4375-R    5'-attggaagcttcgattggctgcgacctag-3'

SEQ ID No. 19:
Atu3234-F    5'-ttgggatcctttcaggggaaatattatggc-3'

SEQ ID No. 20:
Atu3234-R    5'-gccgcaagcttgttttacagcttcac-3'

SEQ ID No. 23:
Xcc3438-F    5'-tcggaattcgcgttgcggtgaatcgttttcaatg-3'

SEQ ID No. 24:
Xcc3438-R    5'-ataagaagcttgctcagtcgctgctgttgccttc-3'

PCR was performed using primers having the following sequences for cloning of BG14057 gene in the genome of *Bacillus subtilis* 168 (including RBS) for expressing it as a recombinant enzyme. The "a" at position 10 from the 5'-terminus is originally "t" but is altered to "a" for expression in *Escherichia coli*.

SEQ ID No. 21:
BG14057-F    5'-aggaattcgatgataacgcttttaaaggggagaa-3'

SEQ ID No. 22:
BG14057-R    5'-tttctgcagtttagtgctccagcataatggttcg-3'

For PCR, Ex taq reaction solution from Takara Shuzo Co., Ltd. was used, and a solution having a composition of 5 µl of 10× Takara ExTaq Buffer, 4 µl of a dNTP mixture, 30 ng of a template DNA, 1 µl of 10 µM primer solution, and 0.5 µl of Takara ExTaq was prepared by adding water so that it has a volume of 50 µl, followed by layering 30 µl of mineral oil. For reaction, a cycle of three steps: denaturation (94° C., 30 seconds), annealing (52° C, 55° C, or 58° C (See Table 3), 1 minute), and elongation (72° C., 1 minute), were repeated 35 times using PCR Amplifier (ASTEC Co., Ltd., PC-700). The above-described PCR amplified a DNA fragment having a size of about 1.1 kbp.

TABLE 3

List of annealing temperature

| Target genes | Annealing temperature |
| --- | --- |
| For Atu4375 gene of *Agrobacterium tumefacience* C58 ATCC33970 | 55° C. |
| For Atu4375 gene of *Agrobacterium* AB10121 FERM P-17383 | 55° C. |
| For Atu3234 gene of *Agrobacterium tumefacience* C58 ATCC33970 | 52° C. |
| For Atu3234 gene of *Agrobacterium* AB10121 FERM P-17383 | 52° C. |
| For BG14057 gene of *Bacillus subtilis* 168 ATCC23857 | 55° C. |
| For Xcc3438 gene of *Xanthomonas campestris* pv. Campestris ATCC33913 | 58° C. |

After the reaction, the layered mineral oil was extracted with 0.3 ml of hexane, and the hexane layer was removed. This procedure was repeated three times, followed by reduction of the pressure for one minute, to thereby remove the mineral oil. From 50 µl of the thus-obtained reaction solution, PCR fragments were purified using GENECLEAN (Bio101). Specifically, 300 µl of the NaI solution included in the kit was added and mixed, and 10 µl of a glass beads solution was added and mixed. The mixture was allowed to stand at 4° C. for 15 minutes and centrifuged to precipitate glass beads to which the DNA fragments were adsorbed, and the supernatant was removed. 500 µl of New wash solution included in the kit was further added to suspend the glass beads, and the mixture was centrifuged to remove the supernatant. The washing operation using the New wash solution was repeated three times. Next, the glass beads were dried under reduced pressure, and after the drying, 15 µl of sterilized water was added to suspend them. The mixture was heated to 55° C. for 15 minutes and centrifuged, to thereby yield 12 µl of a supernatant containing DNA fragments.

An operation of inserting the purified DNA fragment into an expression vector was performed in each of the combinations as follows. Specifically, 0.5 µg of an expression plasmid (pUC118: manufactured by Takara Shuzo Co., Ltd.)), 1 µl of two kinds of restriction enzymes from Takara Shuzo Co., Ltd., and 2 µl of 10× K buffer, which is a restriction enzyme buffer solution from Takara Shuzo Co., Ltd., were added to 10 µl of the DNA fragment solution, and sterilized water was added so that the mixture has a volume of 20 µl, followed by mixing. The reaction solution was allowed to react at 36° C. for 2 hours. As the Atu3234 gene of the AB10121 strain contains a HindIII site, the treatment with restriction enzymes was not conducted, and after isolation, ligated to a pT7Blue vector (manufactured by Novagen).

TABLE 4

List of expression plasmids and used restriction enzymes

| Target genes | Expression plasmids | Used restriction enzymes |
| --- | --- | --- |
| Atu4375 gene of A.tume.C58 | pUC118 | BamH I, Hind III/K buffer |
| Atu4375 gene of AB10121 | pUC118 | BamH I, Hind III/K buffer |
| Atu3234 gene of A.tume.C58 | pUC118 | BamH I, Hind III/K buffer |
| Atu3234 gene of AB10121 | pT7Blue | Not used |
| BG14057 gene of B.sub.168 | pUC118 | EcoR I, Pst I/H buffer |
| Xcc3438 gene of X. camp. | pUC118 | EcoR I, Hind III/K buffer |

After the reaction of the restriction enzymes, DNA fragment and expression vector were isolated with GENECLEAN and ligated with each other. Specifically, 300 µl of the NaI solution included in the kit was added to 20 µl of the restriction enzyme reaction solution and mixed, and 10 µl of the glass beads solution was added and mixed. The mixture was allowed to stand at 4° C. for 15 minutes and then centrifuged to precipitate glass beads to which the DNA fragment and expression vector were adsorbed, and the supernatant was removed. Moreover, 500 µl of the New wash solution included in the kit was added to suspend the glass beads, and the suspension was centrifuged to remove the supernatant. The washing operation using the New wash solution was repeated three times. Next, the glass beads were dried under reduced pressure, and after the drying, 15 µl of sterilized water was added to suspend them. The mixture was heated to 55° C. for 15 minutes and centrifuged, to thereby yield 12 µl of a supernatant containing DNA fragment and expression vector. The procedure removed small DNA fragments generated by the restriction enzymes that have sizes of about 50 bp or less, to thereby yield a DNA fragment of interest and expression vector.

10 µl of Takara Ligation kit-I solution (Takara Shuzo Co., Ltd.) was added to 10 µl of the thus-prepared solution, and the mixture was allowed to react at 16° C. for 1 hour. The solution was used to transform competent cells (Takara Shuzo Co., Ltd.: DH5α). Specifically, 5 μl of a ligation reaction solution was added to 60 μl of a competent cell solution unfreezed at 4° C. and mixed, and left for at 0° C. 30 minutes, then at 42° C. for 45 seconds and 0° C. for 2 minutes. 500 μl of SOC solution (2% bacto-tryptone, 0.5% yeast extract, 10 mM NaCl, 20 mM glucose, 10 mM MgSO$_4$, and 10 mM MgCl$_2$) was added thereto, followed by recovery culture at 36° C. for 1 hour. 100 μl of the culture solution was applied to an LB agar medium (1% bacto-tryptone, 0.5% yeast extract, 1% NaCl, pH 7.0, 1.5% agar) containing 50 μg/ml ampicillin, 40 μg/ml X-gal (5-Bromo4-Chloro-3-Indolyl-β-D-Galactoside), and 1 mM IPTG (thiogalactopyranoside). Culture was further performed at 37° C. for 16 hours. The culture yielded *Escherichia coli* transformed by introducing the above-described plasmid as white colonies, and the colonies were selected. The thus-separated colonies of transformed *Escherichia coli* were cultured in an LB liquid medium containing ampicillin (50 μg/ml). From the cultured cells of the transformed *Escherichia coli*, plasmid DNA was separated and purified using a plasmid purification kit (QIA filter Plasmid Midi Kit, QIAGEN). The thus-obtained plasmid DNA was confirmed to each have a DNA fragment having a size of about 1.0 to 1.1 kbp, which corresponds to the DNA of interest.

Next, to confirm the scyllo-inositol dehydrogenase activity, the microbial strains isolated as colonies were transferred to 100 ml of an LB medium (1% bacto-tryptone, 0.5% yeast extract, 1% NaCl, pH 7.0) containing 50 μg/ml ampicillin, and they were cultured at 36° C. for 7 hours. 0.3 ml of 200 mM thiogalactopyranoside solution was added to the culture solution, and the cells were further cultured at 36° C. for 3 hours. After completion of the culture, the cells were collected by centrifugation and washed with physiological saline once. Then, the washed cells were suspended in 3 ml of 0.6% Triton X-100 solution, and the cells were disrupted by ultrasonic wave at 4° C. The solution was centrifuged, and 2.8 ml of the supernatant (enzyme solution) was taken out. 1.2 g of ammonium sulfate was added to the supernatant to salt out proteins at 4° C. The salted-out proteins were collected by centrifugation, and the supernatant was removed. The precipitates were dissolved in 2.5 ml of 20 mM Tris buffer (pH 7.0), and the solution was centrifuged again. The supernatant was applied onto a Sephadex G-25 column (14 ml) equilibrated with 20 mM Tris buffer (pH 7.0). Elution was performed with 20 mM Tris buffer solution (pH 7.0), and the eluate was desalted. The procedures yielded 3.5 ml of a crude enzyme solution of ydgJ gene product.

The scyllo-inositol dehydrogenase activity was measured as follows: 5 μl of a reaction solution (200 mM Tris buffer (pH 8.0), 2% of NADPH, and 1% of scyllo-inosose) and 5 μl of an enzyme solution were mixed and allowed to react at 36° C. for 30 minutes, and then 500 μl of water was immediately added, followed by measurement of the absorbance at 340 nm. The decrease in the absorbance at 340 nm was measured based on a blank value for a test solution obtained by using water instead of the enzyme solution. The enzyme solution was diluted as required.

Meanwhile, enzyme reaction product was measured as follows: 10 mg of scyllo-inosose, 40 mg of NADPH, and IOU of the enzyme were allowed to react in 1.0 ml of 100 mM Tris buffer (pH 8.0) at 36° C. for 4 hours, and a heat treatment was performed at 80° C. for 10 min, followed by cooling. Then, 100 μl of a strong base cation exchange resin, 100 μl of a strong acid anion exchange resin, and 10 mg of activated carbon were added, and the mixture was stirred and centrifuged. Then, the supernatant was diluted 2-fold, and measurement was performed by HPLC (Shodex Asahipak NH2P-50 4E Φ4.6×250 mm: Shodex) using an RI detector under conditions of a column temperature of 40° C. and a mobile phase flow rate of 1.5 ml (80% acetonitrile). As a result, the Atu4375 gene product and the Atu3234 gene product of *Agrobacterium tumefacience* C58, the BG14057 gene product of *Bacillus subtilis* 168, the Xcc3438 gene product of *Xanthomonas campestris pv. campestris*, and the Atu4375 gene product, and the Atu3234 gene product of AB10121 strain were found to have a high enzyme activity, and 100% of the product was scyllo-inositol obtained by the reduction, while myo-inositol that is an isomer thereof was not detected. As a result, recombinant enzymes derived from the above-mentioned genes were found to have a high scyllo-inositol dehydrogenase activity, and the gene products were scyllo-inositol dehydrogenase. Meanwhile, in the products obtained by the reduction reaction of scyllo-inosose, only scyllo-inositol was detected, and the enzymes were found to stereospecifically reduce scyllo-inosose into scyllo-inositol.

The sequence of Atu4375 gene derived from *Agrobacterium tumefacience* C58 is shown in SEQ ID NO: 3, the corresponding amino acid sequence is shown in SEQ ID NO: 4, the sequence of Atu3234 gene is shown in SEQ ID NO: 5, and the corresponding amino acid sequence is shown in SEQ ID NO: 6. Meanwhile, the sequence of BG14057 gene derived from *Bacillus subtilis* 168 is shown in SEQ ID NO: 7, the corresponding amino acid sequence is shown in SEQ ID NO: 8, the sequence of Atu4375 gene derived from AB10121 is shown in SEQ ID NO: 9, the corresponding amino acid sequence is shown in SEQ ID NO: 10, the sequence of Atu3234 gene is shown in SEQ ID NO: 11, the corresponding amino acid sequence is shown in SEQ ID NO: 12, the sequence of Xcc3438 gene derived from *Xanthomonas campestris pv. campestris* is shown in SEQ ID NO: 13, and the corresponding amino acid sequence is shown in SEQ ID NO: 14. Meanwhile, from the results of nucleotide sequence analysis of a plasmid including Atu4375 gene and Atu3234 gene of AB10121 (Hokkaido System Science Co., Ltd.), the homology between Atu4375 gene of *Agrobacterium tumefacience* C58 and Atu4375 gene of AB10121 was 89% for the nucleotide sequence, and 96% for the amino acid sequence, while the homology between Atu3234 gene of *Agrobacterium tumefacience* C58 and Atu3234 gene of AB10121 was 87% for the nucleotide sequence and 95% for the amino acid sequence.

Example 13

<Isolation of the DNA Encoding SIDH1 which is Produced from *Acetobacter* sp. AB10281 FERM BP-10119>

Of the enzymes purified, an enzyme solution containing SIDH1 was applied onto a PVDF membrane (Immobilon PSQ: manufactured by Millipore Corporation), and absorbed to the PVDF membrane. The PVDF membrane was taken out, stained with Coomassie brilliant blue stain (Rapid CBB KANTO: manufactured by KANTO CHEMICAL CO., INC.), decolorized, and dried, followed by analysis with an N-terminal amino acid analyzer (manufactured by Hewlett-Packard Development Company). As a result, from the N-terminal, a sequence: Met-Lys-Arg-Lys-Leu-Arg-Ile-Gly-Leu-Ile-Gly-Ser-Gly-Phe-Met-Gly-Arg-Thr-His-Ala-Phe-Gly-Tyr-Ser was identified. Then a DNA sequence encoding the amino acid sequence was predicted, and the following two kinds of primers were constructed.

SEQ ID NO: 29:
SIDH1-F1          atgaarcgnaarytncgiatyggyytiatygg

SEQ ID NO: 30:
SIDH1-F2          ggyttyatgggycgnacicaygcittyggyta

Next, based on the nucleotide sequences of various scyllo-inositol dehydrogenases obtained in Examples 10 to 12, there were prepared the following two primers including highly consensus regions within the sequences.

SEQ ID NO: 31:
SIDH1-B1          ggyttrtcrmmgayracrtgrstrcc

SEQ ID NO: 32:
SIDH1-B2          artgwrirtgrttgggigt

Meanwhile, as genomic DNA of AB10281 to be used as a template, a solution of genomic DNA of AB10281 was prepared using the cell pellet (wet weight about 400 mg) prepared in Example 9 in the same way as the method of preparing DNA described in Example 12.

For PCR, Ex taq reaction solution from Takara Shuzo Co., Ltd. was used, and a solution having a composition of 5 µl of 10×Takara ExTaq Buffer, 4 µl of dNTP mixture, 30 ng of a template DNA, 1 µl of each 10 µM primer solution (SIDH1-F1 and SIDH1-B1), and 0.5 µl of Takara ExTaq was prepared by adding water so that it has a volume of 50 µl, followed by layering 30 µl of mineral oil. For reaction, PCR Amplifier (ASTEC Co., Ltd., PC-700) was used, and a cycle of three steps: denaturation (94° C., 30 seconds), annealing (50° C., 30 seconds), and elongation (72° C., 1 minute), was repeated 35 times. Electrophoresis revealed that the above-described PCR amplified a DNA fragment having a size of about 0.3 kbp. Moreover, the band at the position of 0.3 kbp was excised from the gel, a part of a homogenized gel solution was used as a template (2 µl), and there was prepared a reaction solution having the same composition as described above except that a combination of primers was changed to SIDH1-F2 and SIDH1-B2. For reaction, PCR Amplifier (ASTEC Co., Ltd., PC-700) was used, and a cycle of three steps: denaturation (94° C., 30 seconds), annealing (46° C., 30 seconds), and elongation (72° C., 1 minute), was repeated 35 times. Electrophoresis revealed that the PCR amplified a DNA fragment having a size of about 0.25 kbp.

The DNA fragment having a size of about 0.25 kbp was excised from the gel, and the PCR fragment was purified using GENECLEAN (manufactured by Bio101). Specifically, in the same way as the purification method described in Example 12 except that the gel was dissolved in NaI solution, 12 µl of a solution of the DNA fragment was obtained.

Next, the purified DNA fragment was ligated to a pT7Blue vector. Specifically, 0.5 µg of the pT7Blue vector and 10 µl of a Takara Ligation kit-I solution (Takara Shuzo Co., Ltd.) were added to 10 µl of the DNA fragment solution, and the mixture was allowed to react at 16° C. for 1 hour. The solution was used to transform competent cells (DH5α, Takara Shuzo Co., Ltd.). The operation of transformation and isolation of a plasmid from transformants were performed in the same way as Example 12.

The obtained plasmid was subjected to nucleotide sequence analysis (Hokkaido System Science Co., Ltd.) using universal primers (R-20 mer and U-19 mer), and about one third of the former half region of the nucleotide sequence of a gene encoding the enzyme was revealed.

Then, to determine the full length of the nucleotide sequence, genomic DNA of AB10281 was completely digested with a restriction enzyme BamHI, and the resultant DNA fragment solution was purified using GENECLEAN (manufactured by Bio101), followed by self-ligation of the fragment. Specifically, 10 µl of Takara Ligation kit-I solution (Takara Shuzo Co., Ltd.) was added to 10 µl of the DNA fragment solution, and the mixture was allowed to react at 16° C. for 1 hour. After the reaction, the DNA was purified using GENECLEAN (manufactured by Bio101), and the solution was used as a template DNA solution for inverse PCR.

Next, based on the revealed about one third of the former half region of the nucleotide sequence, the following three primers were prepared, and inverse PCR was performed.

SEQ ID No: 33:
SIDH1-INV-F       gctcgtcaacgatcctgaaattgat

SEQ ID No: 34:
SIDH1-INV-B       ttcgctgcagcttcatcggaaatat

SEQ ID No: 35:
SIDH1-INVF3       cccttcaatttccgggcgggt

For inverse PCR, Ex taq reaction solution from Takara Shuzo Co., Ltd. was used, and a solution having a composition of 5 µl of 10×Takara ExTaq Buffer, 4 µl of dNTP mixture, 30 ng of a template DNA, 1 µl of each 10 µM primer solution (a combination of SIDH1-INV-F and SIDH1-INV-B, or a combination of SIDH1-INV-F and SIDH1-INV3), and 0.5 µl of Takara ExTaq was prepared by adding water so that it has a volume of 50 µl, followed by layering 30 µl of mineral oil. For reaction, PCR Amplifier (ASTEC Co., Ltd., PC-700) was used, and a cycle of three steps: denaturation (94° C., 30 seconds), annealing (50° C., 1 minute), and elongation (72° C., 2 minutes), was repeated 35 times. Electrophoresis revealed that the above-described PCR amplified DNA fragments having sizes of about 2.7 kbp and about 1.8 kbp. Then, the bands at the positions of about 2.7 kbp and about 1.8 kbp were excised from the gel, and the PCR fragments were purified using GENECLEAN (manufactured by Bio101), to thereby yield 10 µl of DNA fragment solutions. The resultant two DNA fragments were subjected to nucleotide sequence analysis (Hokkaido System Science Co., Ltd.) using the primers used in PCR to determine the entire nucleotide sequence of the genes encoding the enzyme.

Next, PCR was performed using primers having the following sequences for cloning SIDH1 gene (including an RBS site) derived from AB10281 strain for expressing it as a recombinant enzyme.

SEQ ID No: 36:
281SIDH1-F        gctggatcccgcccttattgtgaata

SEQ ID No: 37:
281SIDH1-R        tatgaattcgttatgccttctcatgctgtcg

For PCR, Ex taq reaction solution from Takara Shuzo Co., Ltd. was used, and a solution having a composition of 5 µl of 10× Takara ExTaq Buffer, 4 µl of dNTP mixture, 30 ng of a template DNA, 1 µl of each 10 µM primer solution, and 0.5 µl of Takara ExTaq was prepared by adding water so that it has a volume of 50 µl, followed by layering 30 µl of mineral oil. For reaction, a cycle of three steps: denaturation (94° C., 30 seconds), annealing (55° C., 1 minute), and elongation (72° C., 1 minute), was repeated 35 times using PCR Amplifier (ASTEC Co., Ltd., PC-700). The above-described PCR amplified a DNA fragment having a size of about 1.2 kbp.

The DNA fragment having a size of about 1.2 kbp was purified using GENECLEAN (manufactured by Bio101), to thereby yield 12 µl of a DNA fragment solution. For a procedure to insert the DNA fragment into an expression vector, 0.5 µg of an expression plasmid (pUC 119), 1 µl of restriction enzymes (BamHI, EcoRI) from Takara Shuzo Co., Ltd., and 2 µl of 10× K buffer for restriction enzymes from Takara Shuzo Co., Ltd. were added to 10 µl of the DNA fragment solution, and sterilized water was added so as to have a volume of 20 µl, followed by mixing. The reaction solution was allowed to react at 36° C. for 2 hours.

Collection of the DNA fragment from the reaction solution, purification, ligation reaction, and transformation of competent cells (DH5α, Takara Shuzo Co., Ltd.) were performed in the same way as Example 12. Moreover, the expression of scyllo-inositol dehydrogenase and the activity measurement were performed in the same way as Example 12, and the gene product was identified as scyllo-inositol dehydrogenase.

As a result, the nucleotide sequence of a gene encoding SIDH1 derived from AB10281 strain is shown in SEQ ID NO: 27, while its amino acid sequence is shown in SEQ ID NO: 28.

Example 14

<Study on Properties of the Enzyme of the Present Invention, Various Kinds of Scyllo-inositol Dehydrogenase>

The following method was performed to study the enzymatic properties of SIDH1, SIDH2, and SIDH3 derived from AB10281 strain, which had been obtained by enzyme purification in Example 9; the ydgj gene product derived from *Escherichia coli*, which had been obtained as a recombinant enzyme in Example 11; and the Atu4375 and Atu3234 gene products of *Agrobacterium tumefacience* C58, the BG14057 gene product of *Bacillus subtilis* 168, the Xcc3438 gene product of *Xanthomonas campestris pv. campestris*, and the Atu4375 and Atu3234 gene products of the AB10121 strain, all of which had been obtained as recombinant enzymes in Example 12, and the results are shown in Table 5.

Table 6 shows the homology in the amino acid sequence. The homology of only the amino acids common in all the sequences was low (about 5%), but the homology including amino acids having similar properties was high particularly in NAD or NADP binding domains in about 30% of the sequence of the N-terminal. Moreover, the lysine-proline sequence located forward the center of the sequence involved in binding of nicotinamide, which is an oxidoreduction reaction site of NAD or NADP, was highly conserved. Asparagine at the 27th position toward the C-terminal from the lysine-proline sequence and the aspartic acid-(3 amino acids)-histidine sequence near the center of the sequence were also highly conserved, so that they are considered as important sequences involved in the substrate binding from the estimated three-dimensional structures. In the table, the common sequences are represented by the symbol "*", the amino acids having similar properties are represented by the symbol ":" or the symbol ".", and Asparagine at the 27th position toward the C-terminal from the lysine-proline sequence and the aspartic acid-(3 amino acids)-histidine sequence near the center of the sequence are represented by hatching.

In the comparison of molecular weights, the molecular weight of the enzyme of the present invention derived from AB10281 was calculated based on the results of SDS-PAGE using a molecular weight marker (prestain standard (broad range type): manufactured by Bio-Rad Laboratories, Inc.), while the molecular weights of the other enzymes of the present invention were estimated from the full lengths of the genes. As a result, the molecular weights of the enzymes of the present invention (SIDH1, SIDH2, and SIDH3) derived from AB10281, which had been obtained by enzyme purification, were 46 k Dalton, 42 k Dalton, and 40 k Dalton, respectively. Meanwhile, the molecular weight of the enzyme of the present invention derived from ydgj gene of *Escherichia coli* K-12, which had been obtained as a recombinant enzyme in Example 11, was 38.2 k Dalton; the molecular weights of the enzymes of the present invention derived from Atu4375 gene and Atu3234 gene of *Agrobacterium tumefacience* C58, which had been obtained as recombinant enzymes in Example 12, were 41.3 k Dalton and 42.4 k Dalton, respectively; the molecular weights of the enzymes of the present invention derived from BG14057 gene of *Bacillus subtilis* 168, Xcc3438 gene of *Xanthomonas campestris pv campestris*, and Atu4375 gene and Atu3234 gene of AB10121 were 40.1 k Dalton, 38.5 k Dalton, 41.4 k Dalton, and 42.5 k Dalton, respectively. That is, the enzymes of the present invention, scyllo-inositol dehydrogenase, were found to have molecular weight of 38 to 46 k Dalton.

Association properties of the enzyme of the present invention were determined by: measuring the activity of fractions obtained by fractionation using a gel filtration column (Tosoh Corporation: 2000SWXL); calculating the molecular weight from the corresponding molecular weight fractions; and dividing the calculated values by the molecular weights of the enzyme. The resultant values were represented as integers. As a result, the enzyme of the present invention, scyllo-inositol dehydrogenases, was found to have molecular weight of 80 k to 110 k Dalton, and was considered to form dimmer or trimer in the undenatured conditions.

Coenzyme selectivity of the enzyme of the present invention was determined by: mixing 5 µl of a reaction solution (200 mM Tris buffer (pH 8.0), 2% of NADPH or NADH, and 1% of scyllo-inosose) with 5 µl of an enzyme solution; and allowing the mixture to react at 36° C. for 30 min. After the reaction, 500 µl of water was immediately added thereto, and the absorbance at 340 nm was measured. From the blank value of a test solution prepared by using water instead of the enzyme solution, the decrease in the absorbance at 340 nm was measured. The enzyme solution was diluted as required. The results indicate that scyllo-inositol dehydrogenases of the enzymes of the present invention were able to use both NADPH and NADH as coenzymes, but have the coenzyme relative activity as shown in Table 5. It was revealed that many enzymes have high reactivity with NADPH.

The optimum pH of the enzymes of the present invention was determined by: mixing 5 µl of a reaction solution (200 mM phosphate buffer (pH 5.0 to 9.0), 2% of NADPH, and 1% of scyllo-inosose) with 5 µl of an enzyme solution; and allowing the mixture to react at 36° C. for 30 min. After the reaction, 500 µl of water was immediately added thereto, and the absorbance at 340 nm was measured. From the blank value of a test solution prepared by using water instead of the enzyme solution, the decrease in the absorbance at 340 nm was measured. The enzyme solution was diluted as required. As a result, the enzymes of the present invention, scyllo-inositol dehydrogenase, were found to have optimum pH as shown in Table 5. That is, the enzymes of the present invention were found to react in the wide range of pH 5 to 9. Meanwhile, it was also revealed that there are enzymes having maximum activity at the acidic side (about pH 6), enzymes having maximum activity at the neutral region (about pH 6.5 to 7.5), and enzymes having maximum activity at the alkaline side (about pH 7.5 to 9).

The thermostability of the enzymes of the present invention was determined by: treating an enzyme solution at the predetermined temperature for 10 min; cooling the solution; mixing the enzyme solution with 5 µl of a reaction solution (200 mM phosphate buffer (pH 5.0 to 9.0), 2% of NADPH, and 1% of scyllo-inosose); and allowing the mixture to react at 36° C. for 30 min. Thereafter, 500 µl of water was immediately added thereto, and the absorbance at 340 nm was measured. From the blank value of a test solution prepared by using water instead of the enzyme solution, the decrease in the absorbance at 340 nm was measured. The enzyme solution was diluted as required. The activity of a group treated at 20° C. for 10 min was defined as 100%, and the relative activities were compared. As a result, the thermostability of the enzymes of the present invention, scyllo-inositol dehydrogenase, was found to vary depending on enzymes as shown in Table 5, and the stability was found to vary in the range of 40 to 60° C. depending on the enzymes.

The effects of heavy metal on the enzymes of the present invention were determined by: mixing 5 µl of a reaction solution (200 mM Tris buffer (pH 8.0), 2% of NADPH, 1% of scyllo-inosose, and 2 mM of a heavy metal) with 5 µl of an enzyme solution; and allowing the mixture to react at 36° C. for 30 min. After the reaction, 500 µl of water was immediately added thereto, and the absorbance at 340 nm was measured. From the blank value of a test solution prepared by using water instead of the enzyme solution, the decrease in the absorbance at 340 nm was measured. The enzyme solution was diluted as required. $CaCl_2$, $CoCl_2$, $ZnSO_4$, $MgSO_4$, $SnCl_2$, $NiCl_2$, and $MnSO_4$ were used as metallic salts. The activity of the no addition group was defined as 100%, and the relative activities were compared. As a result, as shown in Table 5, the enzymes of the present invention, scyllo-inositol dehydrogenase, were activated at least in the presence of $Co^{2+}$ ion and inhibited in the presence of $Sn^{2+}$ ion. Most of the enzymes were inhibited in the presence of $Zn^{2+}$ ion, in contrast, the enzyme derived from Bacillus subtilis 168 was activated in the presence of $Zn^{2+}$ ion.

The Km values of the enzymes of the present invention for scyllo-inosose were determined by: mixing 5 µl of a reaction solution (200 mM Tris buffer (pH 8.0), 2% of NADPH, and 0.001 to 2.5% of scyllo-inosose) with 5 µl of an enzyme solution; and allowing the mixture to react at 36° C. for 30 min. After the reaction, 500 fi of water was immediately added thereto, and the absorbance at 340 nm was measured. From the blank value of a test solution prepared by using water instead of the enzyme solution, the decrease in the absorbance at 340 nm was measured. The enzyme solution was diluted as required. The Km values were calculated by the reciprocal plot. As a result, as shown in Table 5, the enzymes of the present invention, scyllo-inositol dehydrogenase, were found to have Km values in the range of 2.6 to 12.6 mM.

The substrate specificity of the enzymes of the present invention was determined by measuring the relative activity of oxidation with respect to the reactivity to scyllo-inositol. The inositol isomers include scyllo-inositol (SI), myo-inositol (MI), D-chiro-inositol (DCI), L-chiro-inositol (LCI), epi-inositol (EI), muco-inositol (MuI), allo-inositol (AI), and neo-inositol (NI). Table 5 shows the group of isomers to which the enzyme shows a relative activity of not less than 70%, a group of isomers to which the enzyme shows a relative activity of less than 70% and not less than 20%, and a group of isomers to which the enzyme shows a relative activity of less than 20%.

The substrate specificity was determined by: mixing 50 µl of a reaction solution (1% inositol isomers (or 0.4%: only for neo-inositol), 200 mM Tris buffer (pH 8.0), 0.002% $NADP^+$, 0.002% diaphorase, and 0.01% nitrotetrazolium blue) with 50 µl of an enzyme solution; and measuring the increase in the absorbance at 545 nm at 25° C. every three minutes using a microplate reader. The reaction rate was calculated from the absorbance increments at the respective times. As a result, the substrate specificity was found to vary slightly depending on the kinds of the enzymes, and from the correlation with the structures of the inositol isomers, it was also found that those enzymes have at least scyllo-inositol dehydrogenase activity and myo-inositol dehydrogenase activity.

TABLE 5

List of properties of scyllo-inositol dehydrogenase

| Strains | E. coli | | Acetobacter sp. | | Bacillus sub. |
|---|---|---|---|---|---|
| Strain | K12 (ATCC10798) | | AB10281 (FERM P-18868) | | 168 strain (ATCC23857) |
| Gene name or enzyme name | ydgJ gene | SIDH1 | SIDH2 | SIDH3 | BG14057 gene |
| Molecular weight kDalton | 38.2k | 46k(SDS-PAGE) | 42k(SDS-PAGE) | 40k(SDS-PAGE) | 40.1k |
| Association property | Dimer | Trimer | Dimer | Dimer | Dimer |
| Thermostability | Stable at 45° C. or less | Stable at 45° C. or less | Stable at 60° C. or less | Stable at 60° C. or less | Stable at 40° C. or less |
| Coenzyme relative activity | NADPH:NADH = 100:9 | NADPH:NADH = 100:112 | NADPH:NADH = 100:1 | NADPH:NADH = 100:3 | NADPH:NADH = 100:52 |
| Optimum pH | pH7.5-9.0 | pH5.5-6.5 | pH5.5-6.5 | pH5.5-6.5 | pH7.0-8.5 |
| Heavy metal effects: activation | Co | Co | Co | Co, Mn | Co, Mn, Zn |
| Heavy metal effects: strong inhibition | Sn, Zn | Sn, Zn | Sn, Zn | Sn, Zn | Sn |
| Reduction reaction product | Only SIS → SI | Only SIS → SI | Only SIS → SI | Only SIS → SI | Only SIS → SI |
| Km values for scyllo-inosose | 3.9 mM | 7.6 mM | 10.6 mM | 12.6 mM | 3.5 mM |
| Substrate specific Relative activity (70% or more) | SI, MI, DCI | SI | SI | SI | SI, MI |
| Substrate specific Relative activity (20 to 70%) | LCI, EI, MuI | MI | MI | MI | DCI, EI, AI, NI |
| Substrate specific Relative activity (less than 20%) | AI, NI | DCI, LCI, EI, MuI, AI, NI | DCI, LCI, EI, MuI, AI, NI | DCI, LCI, EI, MuI, AI, NI | LCI, MuI |
| Strains | Agrobacterium tumefacience | | Agrobacterium sp. | | Xanthomonas campestris |
| Strain | C58 (ATCC33970) | | AB10121 (FERM P-17383) | | pv.Campestris (ATCC33913) |
| Gene name or enzyme name | Atu4375 gene | Atu3234 gene | Atu4375 gene | Atu3234 gene | Xcc3438 gene |
| kDalton | 41.3k | 42.4k | 41.4k | 42.5k | 38.5k |
| Association property | Dimer | Dimer | Dimer | Dimer | Dimer |
| Thermostability | Stable at 50° C. or less | Stable at 40° C. or less | Stable at 50° C. or less | Stable at 40° C. or less | Stable at 40° C. or less |
| Coenzyme relative activity | NADPH:NADH = 100:9 | NADPH:NADH = 100:18 | NADPH:NADH = 100:6 | NADPH:NADH = 100:20 | NADPH:NADH = 100:34 |
| Optimum pH | pH6.5-8.5 | pH7.0-8.5 | pH6.5-8.5 | pH7.0-8.5 | pH6.5-7.5 |
| Heavy metal effects: activation | Co, Mn | Co, Mn, Ca | Co, Mn | Co, Mn, Ca | Co |
| Heavy metal effects: strong inhibition | Sn, Zn | Sn, Zn | Sn, Zn | Sn, Zn | Sn, Zn |
| Reduction reaction product | Only SIS → SI | Only SIS → SI | Only SIS → SI | Only SIS → SI | Only SIS → SI |

TABLE 5-continued

List of properties of scyllo-inositol dehydrogenase

| | | | | | |
|---|---|---|---|---|---|
| Km values for scyllo-inosose | 9.2 mM | 2.6 mM | 9.8 mM | 3.1 mM | 9.1 mM |
| Substrate specific Relative activity (70% or more) | SI, MI, DCI, EI | SI, MI, DCI, EI, LCI | SI, MI, DCI, EI | SI, MI, DCI, EI, LCI | SI, DCI |
| Substrate specific Relative activity (20 to 70%) | LCI, MuI | MuI | LCI, MuI | MuI | MI |
| Substrate specific Relative activity (less than 20%) | AI, NI | AI, NI | AI, NI | AI, NI | EI, LCI, MuI, AI, NI |

Abbreviations
SIS: Scyllo-inosose,
SI: Scyllo-inositol,
MI: Myo-inositol,
DCI: D-chiro-inositol,
LCI: L-chiro-inositol,
EI: Epi-inositol,
MuI: Muco-inositol,
AI: Allo-inositol,
NI: Neo-inositol

TABLE 6

Homology in the amino acid sequences of various scyllo-inositol dehydrogenase

```
E. coli ydgJ       ----------MSDNIRVGLIGYGYASKTFHAPLI----AGTPGQELAVIS---SSDETKV   (SEQ ID NO:2)

X. camp. Xcc3438   ----------MPKPFNLAVVGYGYVGRTFHAPLI----ASTPGLQLHSVV---SSKPQQP   (SEQ ID NO:14)

B. sub. BG14057    -MITLLKGRRKVDTIKVGILGYGLSGSVFHGPLL----DVLDEYQISKIM---TSRTEEV   (SEQ ID NO:8)

A. tume. Atu4375   --MSSATKKFDSRRIRLGMVGGGQGAFIGAVHRI----AARLDDRYELVAGALSSDPARA   (SEQ ID NO:4)

AB10121Atu4375     --MSSAPKKFDSRRIRLGMVGGGQGAFIGAVHRI----AARLDDRYELVAGALSSDPARA   (SEQ ID NO:10)

A. tume. Atu3234   MAIEGKTTDVANKRIRLGMVGGGSGAFIGGVHRM----AARLDNRFDLVAGALSSTPEKS   (SEQ ID NO:6)

AB10121Atu3234     MAIEGKTTDKANKRIRLGMVGGGSGAFIGGVHRM----AARLDNRFDLVAGALSSTPEKS   (SEQ ID NO:12)

AB10281SIDH1       ---------MTKRKLRIGLIGSG---FMGRTHAFGYSTASRVFDLPFQPELTCLADISDE  (SEQ ID NO:28)
                            : :::::* *                :             .     . .

E. coli ydgJ       KADWPTVTVVSE----------PKHLFNDPNIDLIVIPTPNDTHFPLAKAALEAGKHVV

X. camp. Xcc3438   QADFREVRVLPD----------LEAALADPALDAVVIATPNQTHAPMALQALAAGKHVLV

B. sub. BG14057    KRDFPDAEVVHE----------LEEITNDPAIELVIVTTPSGLHYEHTMACIQAGKHVVM

A. tume. Atu4375   AASATLLGIAPERSYASFEDMAATEAGREDGIEAVAIVTPNHLHFAPSKAFLEAGIHVIC

AB10121Atu4375     AASATLLGIAPERSYASFEEMAAAEAGRDDGIEAVAIVTPNHLHFAPSKAFLEAGIHVIC

A. tume. Atu3234   LASGRELGLDSERCYGSFEEMAEKEALREDGIEAVAIVTPNHVHYPAAKAFLERGIHVIC

AB10121Atu3234     LASGRELGLDPERCYGSFEEMAEKEALREDGIEAVAIVTPNHVHYPAAKAFLERGIHVIC

AB10281SIDH1       AAAKAADALGFARSTSDWRTLV-----NDPEIDVVNITAPNAFHKEMALAAIAAGKHVYC
                   :                       ::::::*. *    :    :. * **:

E. coli ydgJ       DKPFTVTLSQARELDALAKSLGRVLSVFHNRRWDSDFLTLKGLLAEGVLGEVAYFESHFD

X. camp. Xcc3438   DKPFALDAAQARTVVDAAAEAGKIVSVFQNRRWDADFLTVRRLIEDGQLGEVVEFHSHFD

B. sub. BG14057    EKPMTATAEEGETLKRAADEKGVLLSVYHNRRWDNDFLTIKKLISEGSLEDINTYQVSYN

A. tume. Atu4375   DKPVTATLEEAKALAGIVRASDSLFVLTHNYTGYAMLRQMREMIAEGAIGKLRHVQAEYA

AB10121Atu4375     DKPVTATLEEAKALAEIVRASDSLFVLTHNYTGYAMLRQMRQMVADGAIGKLRHVQAEYA

A. tume. Atu3234   DKPLTSNLEDAKKLKDVADKADALFILTHNYTGYPMVRHARELVESGALGTIRLVQMEYP

AB10121Atu3234     DKPLTSNLEDAKKLKDVADKADALFILTHNYTGYPMVRHARELVESGALGTIRLVQMEYP

AB10281SIDH1       EKPLAPLAADAREMAEAAEAKGVKTQVGFNYLCNPHLALARDMIAAGELGEIRGYRGLHA
                   :**.:     .:.:      :        .   .  :      *      .  :::   * :    .

E. coli ydgJ       RFRP--------QVRDRWREQGGP--GSGIWYDLAPHLLDQAITLFG-LPVSM---TVDL
```

TABLE 6-continued

Homology in the amino acid sequences of various scyllo-inositol dehydrogenase

```
X. camp. Xcc3438    RYRP--------QVRDRWRESDIP--GAGLWYDLGPHLLDQALQLFG-MPQAI---SADL B. sub. BG14057     RYRP--------EVQARWREKEGT--ATGTLYDLGSHIIDQTLHLFG-MPKAV---TANV A. tume. Atu4375    QDWLTEAVEKTGAKGAEWRTDPSRSGAGGAIGDIGTHAFNAAAFVTGEIPSSL---YADL AB10121Atu4375      QDWLTEAVEKTGAKGAEWRTDPSRSGAGGAIGDIGTHAFNAAAFVTGEIPKSL---YDAL A. tume. Atu3234    QDWLTEAVEQTGAKQAVWRTDPAQSGVGGSTGDIGTHAYNLGCFISGLEADEL---AADV AB10121Atu3234      QDWLAEPIEQTGAKQAVWRTDPAQSGAGGSTGDIGTHAYNLGCFISGLEVDEL---AADV AB10281SIDH1            EDYMADA-------SSPFTFRLDPA---GGGALDIGHALATAEFLMGPAAGAITQVMGDC
                    :              ::   .   *  *:.:*  .   : *   .  :   .::

E. coli ydgJ        AQLRPGA----------QSTDYFHAILSYPQR--------RVILHGTMLAAAESARYIVH X. camp. Xcc3438    QRQRTQA----------RSDDYFNVVLRYPRL--------RVILHAGSLVADGSLRFAVH B. sub. BG14057     MAQRENA----------ETVDYFHLTLDYGKL--------QAILYGGSIVPANGPRYQIH A. tume. Atu4375    TSFVPGR----------QLDDSANILLRYDSG-----AKGMLWASQIAVGNENALSRVY AB10121Atu4375      TSFVPGR----------CLDDSANILLRYESG-----AKGMLWASQIAVGNENALSRVY A. tume. Atu3234    HTFVEGR----------RLDDNAHVMMRFKPKGGKQPARGMLWCSQVAVGHENGLKIRLY AB10121Atu3234      HTFVEGR----------RLDDNAHVMLRFKPKGGKQPAKGLLWCSQVAVGHENGLKVRVY AB10281SIDH1        VTVIKTRPDGKGGTRAVEVDDIGRALLRFENG-----ATGSVEGNWIATGRTMGHDFEVY
                    .              :  *  :   : :              :     :   ::

E. coli ydgJ        GSRGSYVKYGLDPQEERL--KNGERLP-----QEDWGYDMRD--GVLTRVEGEERVEETL X. camp. Xcc3438    GTRGSYLKHGADTQEDQL--RAGRRPG-----TAGNGMDPLP--GTLTRVDDEGRVHTHQ B. sub. BG14057     GKDSSFIKYGIDGDEDAL--RAGRKPE-----DDSWGADVPEFYGKLTTIRGSDKKTETI A. tume. Atu4375    GDKGGLEWHHRVPDELWF--TPYGEPKRLITRNGAGAGAAANRVSRVPSGHPEGYLEGFA AB10121Atu4375      GEKGGLEWHHRVPDELWF--TPYGEPKRLITRNGAGAGAAANRVSRVPSGHPEGYLEGFA A. tume. Atu3234    GDKAGLEWTQADPNYLWF--TKLGEPKQLITRGGAGAGAAARVTRIPSGHPEGYLEAFA AB10121Atu3234      GDKAGIEWTQADPNYLWF--TKLGELKQLITRGGAGAGAAARVTRIPSGHPEGYLEAFA AB10281SIDH1        GTKGALAFTQQRFNELHFFSSTDARGRKGFRRIEAGPEHAPYGLFCVAPGHQLGFND---
                    * . ..    ..            ..       .       :..

E. coli ydgJ        LT-VPGNYPAYYAAIRDALNGDGENPV-PASQAIQVMELIELGIESAKHRATLCLA----

X. camp. Xcc3438    PDGVPGDYRHCYAAFRDAMAGTAPPPV-SAADAVRLMELLELAGRGAALGQVLWLEGNSS B. sub. BG14057     PS-VNGSYLTYYRKIAESIREGAALPV-TAEEGINVIRIIEAAMESSKEKRTIMLEH---

A. tume. Atu4375    TI-YREAADAIIAKREGETAAGEVIYP-GMEDGLAGLAFIDAAVRSSQ-TSTNYGIDI--

AB10121Atu4375      TI-YREAADAIIAKREGKAAAGEVIYP-GMEDGLAGLAFIDAAVRSSQ-TSTWINIDI--

A. tume. Atu3234    TI-YTEAAHAIEARRTGSALDKAVIYP-TVDDGVKGVAFVTIACIESGKKNGGWVKL---

AB10121Atu3234      TI-YTEAAHAIEARRTGSVLDKAVIYP-TVDDGVKGVAFVTACIESGKKNGVNTVKL---

AB10281SIDH1        -------LKAIEVARYLEALAGHHPEPFNFRAGLRIQTLVETIHASS-KSAAWRDVPTDK
                           .:::  .  ::    ..:.   .:          ::     :      :

E. coli ydgJ        -----------

X. camp. Xcc3438    D----------

B. sub. BG14057     -----------

A. tume. Atu4375    -----------

AB10121Atu4375      -----------
```

TABLE 6-continued

Homology in the amino acid sequences of various scyllo-inositol dehydrogenase

| | |
|---|---|
| A. tume. Atu3234 | ----------- |
| AB10121Atu3234 | ----------- |
| AB10281SIDH1 | LQAKSRQHEKA |

Example 15

<Production of Scyllo-inositol Using the Enzyme of the Present Invention>

The production method of the present invention requires two kinds of enzymes, myo-inositol 2-dehydrogenase and the enzyme of the present invention. Herein, there will be shown an example using a recombinant enzyme of myo-inositol 2-dehydrogenase that is a product of BG10669 gene derived from *Bacillus subtilis* 168 ATCC23857 and a recombinant enzyme of the enzyme of the present invention encoded by DNA of the present invention (ydgj gene derived from *Escherichia coli* K12: SEQ ID NO: 1).

First, to obtain a recombinant enzyme of myo-inositol 2-dehydrogenase that is a product of BG10669 gene derived from *Bacillus subtilis* 168 ATCC23857, the following experiment was performed. PCR was performed using primers having the following sequences for cloning BG10669 gene derived from *Bacillus subtilis* 168 for expressing it as a recombinant enzyme.

SEQ ID NO: 25:
BG10669-F    5'-ttgggatccgatgagtttacgtattggcgtaat
             tg-3'

SEQ ID NO: 26:
BG10669-R    5'-aaactgcagttagttttgaactgttgtaaaaga
             ttgata-3'

For PCR, Ex taq reaction solution from Takara Shuzo Co., Ltd. was used, and a solution having a composition of 5 µl of 10×Takara ExTaq Buffer, 4 µl of dNTP mixture, 30 ng of a template DNA, 1 µl of each 10 µM primer solution, and 0.5 µl of Takara ExTaq was prepared by adding water so that it has a volume of 50 µl, followed by layering 30 µl of mineral oil. For reaction, a cycle of three steps: denaturation (94° C., 30 seconds), annealing (53° C., 1 minute), and elongation (72° C., 1 minute), was repeated 35 times using PCR Amplifier (ASTEC Co., Ltd., PC-700). The above-described PCR amplified a DNA fragment having a size of about 1.0 kbp. After the reaction, the layered mineral oil was extracted with 0.3 ml of hexane, and an operation of removing the hexane layer was repeated three times, followed by reduction of the pressure for 1 minute, to thereby remove the mineral oil. From 50 µl of the thus-obtained reaction solution, PCR fragment was purified using GENECLEAN (Bio101). Specifically, 300 µl of the NaI solution included in the kit was added and mixed, and 10 µl of a glass beads solution was added and mixed. The mixture was allowed to stand at 4° C. for 15 minutes and centrifuged to precipitate glass beads to which the DNA fragment was absorbed, and then the supernatant was removed. 500 µl of New wash solution included in the kit was further added to suspend the glass beads, and the mixture was centrifuged to remove the supernatant. The washing operation using the New wash solution was repeated three times. Next, the glass beads were dried under reduced pressure, and 15 µl of sterilized water was added to suspend them. The mixture was heated to 55° C. for 15 minutes and centrifuged, to thereby yield 12 µl of the supernatant containing DNA fragment.

An operation of inserting the purified DNA fragment into an expression vector was performed as follows. Specifically, 0.5 µg of an expression plasmid (pUC118: manufactured by Takara Shuzo Co., Ltd.)), 1 µl of each of restriction enzymes BamHI and PstI from Takara Shuzo Co., Ltd., and 2 µl of 10×K buffer, which is a restriction enzyme buffer from Takara Shuzo Co., Ltd., were added to 10 µl of the DNA fragment solution, and sterilized water was added so that the mixture has a volume of 20 µl, followed by mixing. The reaction solution was allowed to react at 36° C. for 2 hours. After the reaction of the restriction enzymes, the DNA fragment and expression vector were isolated with GENECLEAN and ligated with each other. Specifically, 300 µl of the NaI solution included in the kit was added to 20 µl of the restriction enzyme reaction solution and mixed, and then 10 µl of the glass beads solution was added and mixed. The mixture was allowed to stand at 4° C. for 15 minutes and then centrifuged to precipitate glass beads to which the DNA fragment and expression vector were adsorbed, and the supernatant was removed. Then, 500 µl of the New wash solution included in the kit was added to suspend the glass beads, and the suspension was centrifuged to remove the supernatant. The washing operation using the New wash solution was repeated three times. Next, the glass beads were dried under reduced pressure, and after the drying, 15 µl of sterilized water was added to suspend them. The mixture was heated to 55° C. for 15 minutes and centrifuged, to thereby yield 12 µl of the supernatant containing the DNA fragment and expression vector. The procedure removed small DNA fragments generated by the restriction enzymes that have sizes of about 50 bp or less, to thereby yield the DNA fragment of interest and expression vector.

10 µl of a Takara Ligation kit-I solution (Takara Shuzo Co., Ltd.) was added to 10 µl of the thus-prepared solution, and the mixture was allowed to react at 16° C. for 1 hour. The solution was used to transform competent cells (Takara Shuzo Co., Ltd.: DH5α). Specifically, 5 µl of a ligation reaction solution was added to 60 µl of a competent cell solution unfreezed at 4° C. and mixed, and left for 30 minutes at 0° C., at 42° C. for 45 seconds and at 0° C. for 2 minutes. 500 µl of SOC solution (2% bacto-tryptone, 0.5% yeast extract, 10 mM NaCl, 20 mM glucose, 10 mM MgSO$_4$, and 10 mM MgCl$_2$) were added thereto, followed by recovery culture at 36° C. for 1 hour. 100 µl of the culture solution was applied on an LB agar medium (1% bacto-tryptone, 0.5% yeast extract, 1% NaCl, pH 7.0, 1.5% agar) containing 50 µg/ml ampicillin, 40 µg/ml X-gal (5-Bromo4-Chloro-3-Indolyl-β-D-Galactoside), and 1 mM IPTG (thiogalactopyranoside). Culture was further performed at 37° C. for 16 hours. The culture yielded *Escherichia coli* transformed by introducing the above-described plasmids as white colonies, and the colonies were selected. The thus-separated colonies of transformed *Escherichia coli* were cultured in an LB liquid medium containing ampicillin (50 µg/ml). From the cultured cells of transformed *Escherichia coli*, the plasmid DNA was separated and purified using a plasmid purification kit (QIA filter Plasmid Midi Kit, QIAGEN). The thus-obtained plasmid DNA was confirmed to have a DNA fragment having a size of about 1.0 k bp, which corresponds to the BG10669 gene of interest.

Next, to confirm the scyllo-inositol 2-dehydrogenase activity, the cells isolated as colonies were transferred into 30 bottles of 100 ml of an LB medium (1% bacto-tryptone, 0.5% yeast extract, 1% NaCl, pH 7.0) containing 50 µg/ml ampicillin, and they were cultured at 36° C. for 7 hours. 0.3 ml of 200 mM thiogalactopyranoside solution was added to each 100 ml of the culture solution, and the cells were further cultured at 36° C. for 3 hours. After completion of the culture, the cells were collected by centrifugation and washed with physiological saline once. Then, the washed cells were suspended in 3 ml of 0.6% Triton X-100 solution, and the cells were disrupted by ultrasonic wave at 4° C. The solution was centrifuged, and 84 ml of the supernatant (enzyme solution) was taken out. 36 g of ammonium sulfate was added to the supernatant to salt out proteins at 4° C. The resultant proteins were collected by centrifugation, and the supernatant was removed. The precipitates were dissolved in 75 ml of 20 mM Tris buffer (pH 7.0), and the solution was centrifuged again. The supernatant was applied onto Sephadex G-25 column (Pharmacia K.K.)(400 ml) equilibrated with 20 mM Tris buffer (pH 7.0), and elution was performed with 20 mM Tris buffer (pH 7.0). Elution was performed with 20 mM Tris buffer (pH 7.0), and the eluate was desalted. The procedures yielded 105 ml of a crude enzyme solution of BG10669 gene product.

The myo-inositol 2-dehydrogenase reducing activity was measured as described below. 5 µl of a reaction solution (200 mM Tris buffer (pH 8.0), 2% of NADH, 1% of scyllo-inosose) was mixed with 5 µl of an enzyme solution, and the mixture was allowed to react at 36° C. for 30 min. Immediately after the reaction, 500 µl of water was added, and the absorbance at 340 nm was measured. From the blank value of a test tube prepared by using water instead of the enzyme solution, the decrease in the absorbance at 340 nm was measured. The enzyme solution was diluted as required, and the enzyme was confirmed to have an activity to reduce scyllo-inosose. On the other hand, to measure an oxidation activity, 50 µl of a reaction solution (1% myo-inositol or scyllo-inositol, 200 mM Tris buffer (pH 8.0), 0.002% NAD$^+$, 0.002% diaphorase, and 0.01% nitrotetrazolium blue) was mixed with 50 µl of an enzyme solution, and the increase in the absorbance at 545 nm was measured at 25° C. every three minutes using a microplate reader. The reaction rate was calculated from the absorbance increments at the respective times. As a result, the prepared enzyme was confirmed to have an activity to oxidize myo-inositol but have no activity to oxidize scyllo-inositol.

The thus-prepared myo-inositol 2-dehydrogenase enzyme solution and the scyllo-inositol dehydrogenase crude enzyme solution prepared in Example 11 (105 ml of the enzyme solution prepared from 3 L of a culture solution (30-fold scale)) were used to perform a reaction to convert myo-inositol into scyllo-inositol. To prepare a reaction solution, 200 g of myo-inositol, 70 ml of 5% of scyllo-inosose, 130 mg of CoCl$_2$, and 250 mg of MgSO$_4$.7H$_2$O were mixed, and the volume was adjusted to 750 ml by adding water, followed by heating up to 50° C. to dissolve myo-inositol. The solution was cooled to 36° C. and adjusted to pH 8.0 with 1N NaOH aqueous solution, and the volume was adjusted to 790 ml by adding water. 105 ml of a crude enzyme solution of myo-inositol 2-dehydrogenase, 105 ml of a crude enzyme solution of scyllo-inositol dehydrogenase, and 70 mg of NADP$^+$ were added thereto at 36° C., and the temperature of the solution having a volume of about 1 L was kept at 36° C., followed by reaction with slow stirring. The reaction solution gradually became acidic, so that it was adjusted to pH 8.0 with 1N NaOH. 42 hours later, crystals of scyllo-inositol were generated in the reaction solution, so that a white reaction solution was obtained. The solution was filtered using a filter paper to collect crystalline scyllo-inositol (wet weight 73 g). 3 L of water was added to the solid, and the solid was dissolved at 50° C. The volume of the mixture was adjusted to 4.5 L by adding water, and the mixture was cooled to room temperature. The resultant solution was centrifuged (8,000 rpm, 20 minutes) to remove insoluble matters, and the supernatant was passed through a column filled with 100 ml of strong base cation exchange resin, a column filled with 100 ml of strong acid anion exchange resin, and a column filled with 50 ml of activated carbon, in this order, to thereby yield each of an eluate. Thereafter, 500 ml of water was passed through each of the columns to wash them, to thereby yield each of a washing solution. The eluate and the washing solution were blended and concentrated.

As a result of the concentration, microcrystals began to be crystallized as the volume of the solution became small, and the solution was concentrated until the weight of the contents became 130 g. The concentrated solution was cooled to 4° C. and allowed to stand overnight. Thereafter, slurry substances were filtered, and the crystals of scyllo-inositol on the filter paper were washed with a small amount of water, followed by drying at 105° C. for 3 hr. The resultant scyllo-inositol was white crystals (61 g), and NMR analysis and HPLC analysis revealed that the crystals contain no other impurities and have a purity of 99% or more. The yield from myo-inositol was 31%. Meanwhile, the reaction solution that had been separated by filtration could also be utilized, and when 64 g of myo-inositol was dissolved therein, crystalline scyllo-inositol was further crystallized.

Example 16

<Formation of Scyllo-inositol/Boric Acid Complex and Study on the Formation Condition>

100 g of scyllo-inosose powder was dissolved in 500 ml of hot water, and the solution was cooled to room temperature. Thereafter, water was added in such a manner that the solution has a volume of 900 ml. The solution was adjusted to pH 7.5 with 5N NaOH aqueous solution, and water was further added so as to have a volume of 1 L.

5.9 g of NaBH$_4$ powder was gradually added to the solution over 15 minutes with stirring to perform a reduction reaction. The temperature of the reaction solution increased up to 38° C. due to heat of the reaction. 30 minutes later, 67.5 g of boric acid and 72.2 g of NaCl were dissolved in the reaction solution which had been cooled to 32° C., to thereby prepare a solution in which the complex was formed. The pH of the solution was 5.9.

Next, 100 ml of the solution, in which the complex was formed and was adjusted to pH 6.0 with 8N NaOH aqueous solution, was dispensed in a 200-ml plastic container with a cover, and 100 ml of the solution, in which the complex was formed and was adjusted to pH 7.0 with 8N NaOH aqueous solution, was dispensed in the same way as above. Furthermore, each of 100 ml of the solutions, in which the complex was formed and each of which was adjusted to pH 8.0, 9.0, 9.5, 10.0, 10.5, 11.0, 12.0, or 12.8, were dispensed.

In those pH-adjusted solutions, precipitates gradually began to be formed. The precipitates were separated by filtration every other day, and the filtrate was adjusted to a predetermined pH with 8N NaOH aqueous solution and then returned to the original container. The resultant precipitates were dried and then weighed. If all of the scyllo-inositol generated by reduction form a scyllo-inositol/boric acid complex and are obtained as precipitates, the weight of the precipitates would be 61.8 g. Therefore, the weights of the precipitates obtained from the respective pH-adjusted solutions were integrated every other day, and values obtained by dividing the integrated values by theoretical yield (61.8 g) were defined as the recovery rates of the scyllo-inositol/boric acid complex precipitates.

The thus-obtained values are shown below.

The gray parts in the table show a test group of the recovery rate of more than 90%.

Table 7

| Treatment pH | Recovery rate of scyllo-inositol/boric acid complex | | | | | | |
|---|---|---|---|---|---|---|---|
| | Day 1 | Day 2 | Day 3 | Day 4 | Day 5 | Day 6 | Day 7 |
| 6 | 9.4% | 17.9% | 25.5% | 32.4% | 38.6% | 44.2% | 49.2% |
| 7 | 21.7% | 38.4% | 51.2% | 61.1% | 68.7% | 74.6% | 79.1% |
| 8 | 42.4% | 65.7% | 78.6% | 85.6% | 89.5% | 91.6% | 92.8% |
| 9 | 66.9% | 86.3% | 91.9% | 93.6% | 94.0% | 94.2% | 94.2% |
| 9.5 | 82.9% | 92.9% | 94.1% | 94.2% | 94.2% | 94.2% | 94.2% |
| 10 | 57.5% | 79.9% | 88.6% | 92.1% | 93.4% | 93.9% | 94.1% |
| 10.5 | 41.5% | 64.7% | 77.7% | 85.0% | 89.0% | 91.3% | 92.6% |
| 11 | 36.8% | 59.2% | 72.8% | 81.2% | 86.3% | 89.4% | 91.3% |
| 12 | 29.2% | 49.4% | 63.3% | 72.9% | 79.5% | 84.1% | 87.2% |
| 12.8 | 25.4% | 44.0% | 57.6% | 67.5% | 74.7% | 80.0% | 83.8% |

As shown in Table 7, the test group of treatment at pH of 9.5 was most suitable for formation of precipitation of the scyllo-inositol/boric acid complex. The recovery rates of the test groups of pH 9.0, pH 9.5, and pH 10.0 reached a recovery rate of 90% or more by day 4, and it was found that the recovery rate became constant of 94% even if the test period is extended.

NMR analysis for the filtrate of the test group of pH 9.5 at day 7 revealed that 5.9% (w/v) myo-inositol and about 0.2% (w/v) scyllo-inositol remained in the solution. That is, it was found that the complex may be taken out as precipitates by the method of the present invention in the case where the concentration of the scyllo-inositol/boric acid complex is 0.2% (w/v) or more.

Example 17

<Method of Forming Scyllo-inositol/Boric Acid Complex from Scyllo-inosose Reduction Mixture and Dissolving the Complex, and then Releasing and Desalting Scyllo-inositol Using Ion Exchange Resin>

10 g (56 mmol) of scyllo-inosose powder was dissolved in 50 ml of hot water, and the solution was cooled to room temperature. Thereafter, water was added so as to have a volume of 90 ml. The solution was adjusted to pH 7.5 with 5N NaOH aqueous solution, and water was further added so as to have a volume of 100 ml.

0.59 g of $NaBH_4$ powder was gradually added to the solution over 15 minutes with stirring to perform a reduction reaction. The temperature of the reaction solution increased up to 36° C. due to heat of the reaction. 30 minutes later, 6.75 g of boric acid and 7.22 g of NaCl were dissolved in the reaction solution cooled to 31 ° C., to thereby prepare a solution in which complex was formed. Next, the solution in which complex was formed was adjusted to pH 9.5 with 5N NaOH aqueous solution, and the solution was maintained to pH 9.5 with 5N NaOH aqueous solution by pH stat apparatus with stirring. 3 days later, precipitates contained in the solution in which complex was formed were filtered and washed with a small amount of water, followed by drying, to thereby yield 5.71 g (20.5 mmol) of a scyllo-inositol/boric acid complex.

230 ml of 1.05N hydrochloric acidic solution was added to 5.71 g of the resultant scyllo-inositol/boric acid complex, to dissolve the scyllo-inositol/boric acid complex, and thereby a dissolved solution was obtained. The dissolved solution was 0.2N acidic solution. Next, the dissolved solution was passed through a column filled with 200 ml of strong acidic ion exchange resin (Duolite C20, $H^+$ type, Sumitomo Chemical Co., Ltd.) at a flow rate of 2 ml/min, and the resultant eluate was then passed through a column filled with 400 ml of strong base ion exchange resin (Duolite A116, OH-type, Sumitomo Chemical Co., Ltd.). The resultant eluate was concentrated, to thereby yield 3.52 g (19.5 mmol) of white powder. NMR analysis revealed that the white powder was scyllo-inositol. Meanwhile, the yield of scyllo-inositol from scyllo-inosose was 35%.

Example 18

<Method of Forming Scyllo-inositol/Boric Acid Complex from a Scyllo-inosose Reduction Mixture and Dissolving the Complex, and then Releasing and Crystallizing Scyllo-inositol by Organic Solvent Precipitation>

As a raw material, 5.71 g (20.5 mmol) of a scyllo-inositol/boric acid complex that had been prepared from 10 g (56 mmol) of scyllo-inosose powder in the same way as Example 17 was used.

5.71 g of a scyllo-inositol/boric acid complex was added to a 100-ml conical flask with a cover together with a stirrer, and 22.8 ml of 1.83N hydrochloric acidic solution was added to prepare a suspension. After the completion of stirring for 1 hour, 23 ml of methanol was added thereto, and the mixture was further stirred. 5 hours later, the suspension was filtered, and the solids were washed with a small amount of methanol and dried, to thereby yield 3.58 g (20.0 mmol) of crude scyllo-inositol.

Then, 3.58 g of the resultant crude scyllo-inositol was dissolved in 230 ml of water, and 20 ml of a strong acidic ion exchange resin (Duolite $C20/H^+$ type) and 40 ml of a strong base ion exchange resin (Duolite $A116/OH^-$ type) were added thereto, followed by stirring. After the completion of stirring for 30 minutes, the ion exchange resins were separated by filtration, and the resultant filtrate was concentrated, to thereby yield 3.41 g (18.9 mmol) of white powder. NMR analysis revealed that the white powder was scyllo-inositol. Meanwhile, the yield of scyllo-inositol from scyllo-inosose was 34%.

Example 19

<Method of Reducing Scyllo-inosose, and then Directly Releasing and Crystallizing Scyllo-inositol>

5 g (28 mmol) of scyllo-inosose powder was dissolved in 40 ml of hot water, and the solution was cooled to room temperature. The solution was adjusted to pH 7.5 with 5N NaOH aqueous solution, and water was further added so as to have a volume of 45 ml.

0.29 g of $NaBH_4$ powder was gradually added to the solution over 15 minutes with stirring to perform a reduction reaction. The temperature of the reaction solution increased up to 37° C. due to heat of the reaction. 30 minutes later, the reaction solution which had been cooled to 30° C. was adjusted to pH 1.0 with 5N hydrochloric acid. Thereafter, water was added so as to have a volume of 50 ml, to thereby prepare 0.1N acidic solution. Next, 25 ml of methanol was added to the solution with stirring. 10 minutes later, the solution gradually began to become opaque, and the suspension was further stirred for 24 hours. 24 hours later, the suspension was filtered, and washing was performed with a small amount of methanol, followed by drying, to thereby yield 1.55 g (8.6 mmol) of crude scyllo-inositol.

Then, 1.55 g of the resultant crude scyllo-inositol was dissolved in 120 ml of water, and 10 ml of a strong acidic ion exchange resin (Duolite $C20/H^+$ type) and 20 ml of a strong base ion exchange resin (Duolite $A116/OH^-$ type) were added, followed by stirring. After the completion of stirring for 30 minutes, the ion exchange resins were separated by filtration, and the resultant filtrate was concentrated, to thereby yield 1.51 g (8.3 mmol) of white powder. NMR analysis revealed that the white powder was scyllo-inositol. Meanwhile, the yield of scyllo-inositol from scyllo-inosose was 30%.

INDUSTRIAL APPLICABILITY

According to the present invention, scyllo-inositol that is available as a drug can be directly produced from inexpensive myo-inositol only by microorganism conversion or enzymatic reaction, and scyllo-inositol can be produced efficiently. Meanwhile, the production method of the present invention has an advantage of hardly generating isomers.

When NAD+-independent myo-inositol 2-dehydrogenase of the present invention is used, scyllo-inosose may be produced without adding NAD+ to a reaction solution. Moreover, high purity of scyllo-inositol may be obtained easily and efficiently by reduction of the resultant scyllo-inosose.

According to the present invention, a scyllo-inositol/boric acid complex can be efficiently formed from a mixture that contains scyllo-inositol and neutral sugars other than scyllo-inositol, and high purity of scyllo-inositol can be efficiently obtained from the resultant scyllo-inositol/boric acid complex by easy operation.

What is claimed is:

1. A method for producing a purified scyllo-inositol, comprising:

a first step of precipitating a scyllo-inositol/boric acid complex by adding boric acid and a metal salt into a liquid mixture containing scyllo-inositol and neutral sugar other than scyllo-inositol in an amount by mol two times or more that of scyllo-inositol dissolved in the liquid mixture, and by adjusting the pH of the liquid mixture to 8.0 to 11.0;

a second step of separating the complex from the liquid mixture;

a third step of dissolving the separated complex into acid to cleave into scyllo-inositol and boric acid to obtain an acidic solution or acidic suspension; and a fourth step of adding ethanol or methanol to the acidic solution or acidic suspension to precipitate scyllo-inositol and purifying the scyllo-inositol from the acidic solution or acidic suspension, wherein the metal salt to be added is one or more kinds of metal salts selected from the group consisting of NaCl, $NaHCO_3$, $Na_2CO_3$, $Na_2SO_4$, $NaHSO_4$, $NaH_2PO_4$, $Na_2HPO_4$, $Na_3PO_4$, borax, KCl, $KHCO_3$, $K_2CO_3$, $K_2SO_4$, $KHSO_4$, $KH_2PO_4$, $K_2HPO_4$, $K_3PO_4$, $MgCl_2$, $MgCO_3$, and $MgSO_4$, and wherein the ethanol is added in a volume 0.3 to 3 times the volume of the acidic solution or acidic suspension, or the methanol is added in a volume 0.3 to 5 times the volume of the acidic solution or acidic suspension.

2. The method according to claim 1, wherein, in the first step, the amounts of the boric acid and metal salt to be added are two to three times the amount by mol of the scyllo-inositol dissolved in the liquid mixture.

3. The method according to claim 1, wherein, in the first step, the pH of the liquid mixture is adjusted to 9.0 to 10.0.

4. The method according to claim 1, wherein the ethanol is added in a volume 0.6 to 1.5 times the volume of the acidic solution or acidic suspension, or the methanol is added in a volume 0.9 to 2 times the volume of the acidic solution or the acidic suspension.

* * * * *

UNITED STATES PATENT AND TRADEMARK OFFICE
CERTIFICATE OF CORRECTION

| | | |
|---|---|---|
| PATENT NO. | : 7,745,671 B2 | Page 1 of 4 |
| APPLICATION NO. | : 10/576030 | |
| DATED | : June 29, 2010 | |
| INVENTOR(S) | : Yamaguchi et al. | |

It is certified that error appears in the above-identified patent and that said Letters Patent is hereby corrected as shown below:

Title Page 1, Column 2, Line 8, Other Publications, "Weser, U. Stucture & Bonding," should be changed to --Weser, U. Structure & Bonding,--

Title Page 1, Column 2, Line 23, Other Publications, "Duterium Oxide,"" should be changed to --Deuterium Oxide,"--

Title Page 1, Column 2, Line 28, Other Publications, "of *myo*-lnositol from" should be changed to --of *myo*-Inositol from--

Title Page 2, Column 2, Line 16, Other Publications, "*myo*-lnosit in" should be changed to --*myo*-Inosit in--

Title Page 2, Column 2, Line 19, Other Publications, "*myo*-lnositol Transport" should be changed to --*myo*-Inositol Transport--

Column 5, Line 8, "Subsequently; in order" should be changed to --Subsequently, in order--

Column 6, Line 56, "according to(1)," should be changed to --according to (1),--

Column 7, Line 11, "accepting substance" should be changed to --accepting substance;--

Column 7, Line 13, "5.5" should be changed to --5.5;--

Column 7, Line 15, "enzyme" should be changed to --enzyme;--

Column 7, Line 17, "$Sn^{2+}$ ion" should be changed to --$Sn^{2+}$ ion;--

Column 7, Line 20, "Dalton" should be changed to --Dalton;--

Signed and Sealed this
Eighth Day of February, 2011

David J. Kappos
*Director of the United States Patent and Trademark Office*

CERTIFICATE OF CORRECTION (continued)
U.S. Pat. No. 7,745,671 B2

Column 7, Line 21, "(g) Substrate" should be changed to --(f) Substrate--

Column 7, Line 25, "and glucose" should be changed to --and glucose.--

Column 9, Line 32, "reaction is crystalyzed" should be changed to --reaction is crystallized--

Column 11, Line 56, "thereof Examples of" should be changed to --thereof. Examples of--

Column 18, Line 8, "is 0.1% to 20%,." should be changed to --is 0.1% to 20%.--

Column 19, Line 9, "An example of-the" should be changed to --An example of the--

Column 22, Line 39, "*Agrobacterium tumefacience* C58" should be changed to --*Agrobacterium tumefaciens* C58--

Column 25, Line 14, "tol (A1), and" should be changed to --tol (AI), and--

Column 25, Lines 48-49, "*Agrobacterium tumefacience* C58" should be changed to --*Agrobacterium tumefaciens* C58--

Column 25, Line 53, "ATCC339913 (hereinafter," should be changed to --ATCC33913 (hereinafter,--

Column 27, Line 16, "at 340 n under" should be changed to --at 340 nm under--

Column 39, Line 61, "supermatant solution." should be changed to --supernatant solution.--

Column 44, Line 17, "5NH2 column" should be changed to --5NH$_2$ column--

Column 44, Lines 63-64, "OH-type)." should be changed to --OH$^-$ type).--

Column 50, Line 18, "the ydgj gene" should be changed to --the ydgJ gene--

Column 50, Line 27, "the ydgj gene" should be changed to --the ydgJ gene--

Column 51, Line 12, "ydgj - F" should be changed to --ydgJ - F--

Column 51, Line 15, "ydgj - R" should be changed to --ydgJ - R--

Column 51, Line 52, "Co., Ltd.))," should be changed to --Co., Ltd.),--

Column 52, Line 11, "by the-restriction" should be changed to --by the restriction--

Column 52, Line 28, "(5-Bromo4" should be changed to --(5-Bromo-4- --

Column 52, Line 40, "to the ydgj gene" should be changed to --to the ydgJ gene--

Column 53, Line 18, "4E Φ4.6x250 mm:" should be changed to --4E Φ 4.6x250 mm:--

Column 53, Line 38, "ydgj Gene, and" should be changed to --ydgJ Gene, and--

Column 53, Line 56, "the ydgj gene" should be changed to --the ydgJ gene--

Column 53, Line 58, "*Agrobacterium tumefacience* C58" should be changed to --*Agrobacterium tumefaciens* C58--

Column 53, Line 67, "*Agrobacterium tumefacience* C58" should be changed to --*Agrobacterium tumefaciens* C58--

Column 54, Line 4, "*Agrobacterium tumefacience* C58" should be changed to --*Agrobacterium tumefaciens* C58--

Column 54, Lines 6-7, "*Agrobacterium tumefacience* C58" should be changed to --*Agrobacterium tumefaciens* C58--

Column 54, Lines 45-46, "*Agrobacterium tumefacience* C58" should be changed to --*Agrobacterium tumefaciens* C58--

Column 54, Line 63, "*Agrobacterium tumefacience* C58," should be changed to --*Agrobacterium tumefaciens* C58,--

Column 55, Table 3, Line 52, "*Agrobacterium tumefacience*" should be changed to --*Agrobacterium tumefaciens*--

Column 55, Table 3, Line 56, "*Agrobacterium tumefacience*" should be changed to --*Agrobacterium tumefaciens*"

Column 56, Line 20, "Co., Ltd.))," should be changed to --Co., Ltd.),--

Column 57, Line 13, "(5-Bromo4-" should be changed to --(5-Bromo-4- --

Column 57, Line 40, "to the supermatant to" --to the supernatant to--

Column 58, Line 3, ""4E Φ4.6x250 mm:" should be changed to --4E Φ 4.6x250 mm:--

Column 58, Lines 6-7, "*Agrobacterium tumefacience* C58," should be changed to --*Agrobacterium tumefaciens* C58,--

Column 58, Lines 22-23, "*Agrobacterium tumefacience* C58" should be changed to --*Agrobacterium tumefaciens* C58--

Column 58, Lines 41-42, "*Agrobacterium tumefacience* C58" should be changed to --*Agrobacterium tumefaciens* C58--

Column 58, Lines 44-45, "*Agrobacterium tumefacience* C58" should be changed to --*Agrobacterium tumefaciens* C58--

Column 61, Line 30, "the ydgj gene" should be changed to --the ydgJ gene--

Column 61, Line 33, "*Agrobacterium tumefacience* C58," should be changed to --*Agrobacterium tumefaciens* C58,--

Column 62, Line 2, "from ydgj gene" should be changed to --from ydgJ gene--

Column 62, Line 6-7, "*Agrobacterium tumefacience* C58," should be changed to --*Agrobacterium tumefaciens* C58,--

Column 62, Line 10, "*campestris pv*" should be changed to --*campestris pv.*--

Column 63, Line 31, "500 fi of water" should be changed to --500 µl of water--

Columns 63-64, Table 5, Line 23, "*Agrobacterium tumefacience*" should be changed to --*Agrobacterium tumefaciens*--

Column 69, Line 23, "(ydgj gene derived" should be changed to --(ydgJ gene derived--

Column 70, Line 18, "Co., Ltd.))," should be changed to --Co., Ltd.),--

Column 70, Line 58, "(5-Bromo4-" should be changed to --(5-Bromo-4- --

Column 75, Line 54, "OH-type, Sumitomo" should be changed to --OH⁻type, Sumitomo--

SEQUENCE LISTING

```
<160> NUMBER OF SEQ ID NOS: 37

<210> SEQ ID NO 1
<211> LENGTH: 1041
<212> TYPE: DNA
<213> ORGANISM: Escherichia coli
<220> FEATURE:
<221> NAME/KEY: CDS
<222> LOCATION: (1)..(1041)
<223> OTHER INFORMATION:

<400> SEQUENCE: 1 atg agc gac aac atc cgt gtt ggg ttg att ggg tat ggt tat gcg agc      48
Met Ser Asp Asn Ile Arg Val Gly Leu Ile Gly Tyr Gly Tyr Ala Ser
1               5                   10                  15 aaa acc ttc cat gcg ccc ctg att gcg ggc acg ccc ggg cag gaa ctg      96
Lys Thr Phe His Ala Pro Leu Ile Ala Gly Thr Pro Gly Gln Glu Leu
            20                  25                  30 gcg gta atc tcc agc agt gat gaa aca aaa gta aaa gcc gac tgg cca     144
Ala Val Ile Ser Ser Ser Asp Glu Thr Lys Val Lys Ala Asp Trp Pro
        35                  40                  45 acg gtt acg gtt gtc tct gag ccg aag cat ctg ttt aac gat ccc aac     192
Thr Val Thr Val Val Ser Glu Pro Lys His Leu Phe Asn Asp Pro Asn
    50                  55                  60 ata gac ctg att gtc att cct aca ccc aac gat acc cat ttc ccg tta     240
Ile Asp Leu Ile Val Ile Pro Thr Pro Asn Asp Thr His Phe Pro Leu
65                  70                  75                  80 gcc aaa gcg gcg ctt gag gcg ggt aaa cat gtg gtc gtt gat aaa ccc     288
Ala Lys Ala Ala Leu Glu Ala Gly Lys His Val Val Val Asp Lys Pro
                85                  90                  95 ttt acc gtg aca ctg tca caa gcg cga gag ctg gat gcg ctg gca aaa     336
Phe Thr Val Thr Leu Ser Gln Ala Arg Glu Leu Asp Ala Leu Ala Lys
            100                 105                 110 agc ctg ggg cgt gtg ctg tct gta ttc cat aac cgt cgc tgg gat agc     384
Ser Leu Gly Arg Val Leu Ser Val Phe His Asn Arg Arg Trp Asp Ser
        115                 120                 125 gat ttc ttg acg cta aaa ggt tta ctc gcg gaa ggc gtg ctg ggt gaa     432
Asp Phe Leu Thr Leu Lys Gly Leu Leu Ala Glu Gly Val Leu Gly Glu
    130                 135                 140 gtt gct tac ttt gag tct cat ttt gac cgc ttc cgt ccg cag gtg cgc     480
Val Ala Tyr Phe Glu Ser His Phe Asp Arg Phe Arg Pro Gln Val Arg
145                 150                 155                 160 gat cgt tgg cgt gaa cag ggc ggc cca ggc agc ggt atc tgg tac gat     528
Asp Arg Trp Arg Glu Gln Gly Gly Pro Gly Ser Gly Ile Trp Tyr Asp
                165                 170                 175 tta gca cca cat ctt ctt gat cag gcc att acg ctt ttt ggt tta ccg     576
Leu Ala Pro His Leu Leu Asp Gln Ala Ile Thr Leu Phe Gly Leu Pro
            180                 185                 190 gtc agc atg acg gta gat ttg gca cag tta cgg ccc gga gcg cag tcg     624
Val Ser Met Thr Val Asp Leu Ala Gln Leu Arg Pro Gly Ala Gln Ser
        195                 200                 205 acc gat tat ttc cac gcc atc ttg tcc tat cca cag cgg cga gtc att     672
```

```
Thr Asp Tyr Phe His Ala Ile Leu Ser Tyr Pro Gln Arg Arg Val Ile
    210                 215                 220 tta cac ggt acc atg ctg gca gcc gct gag tca gca cgg tat atc gtg     720
Leu His Gly Thr Met Leu Ala Ala Ala Glu Ser Ala Arg Tyr Ile Val
225                 230                 235                 240 cat gga tcc cga ggc agt tat gtg aaa tat ggc ctc gat cca cag gaa     768
His Gly Ser Arg Gly Ser Tyr Val Lys Tyr Gly Leu Asp Pro Gln Glu
                    245                 250                 255 gaa cgt ctg aaa aat ggc gag cgt cta ccg cag gaa gac tgg ggc tac     816
Glu Arg Leu Lys Asn Gly Glu Arg Leu Pro Gln Glu Asp Trp Gly Tyr
                260                 265                 270 gat atg cgt gat ggc gta ctt acc cgc gtg gaa ggt gag gaa cgt gtc     864
Asp Met Arg Asp Gly Val Leu Thr Arg Val Glu Gly Glu Glu Arg Val
            275                 280                 285 gaa gaa acg ctg ttg acg gtg cct ggg aat tat ccg gct tac tat gcg     912
Glu Glu Thr Leu Leu Thr Val Pro Gly Asn Tyr Pro Ala Tyr Tyr Ala
        290                 295                 300 gct att cgt gat gcg tta aat ggc gat ggt gaa aat ccg gtt ccg gca     960
Ala Ile Arg Asp Ala Leu Asn Gly Asp Gly Glu Asn Pro Val Pro Ala
305                 310                 315                 320 agc cag gca atc cag gta atg gag ttg att gag ctg ggc atc gaa tcc    1008
Ser Gln Ala Ile Gln Val Met Glu Leu Ile Glu Leu Gly Ile Glu Ser
                    325                 330                 335 gcc aaa cat cgc gcg act ttg tgc ctt gca tga                        1041
Ala Lys His Arg Ala Thr Leu Cys Leu Ala
                340                 345

<210> SEQ ID NO 2
<211> LENGTH: 346
<212> TYPE: PRT
<213> ORGANISM: Escherichia coli

<400> SEQUENCE: 2

Met Ser Asp Asn Ile Arg Val Gly Leu Ile Gly Tyr Gly Tyr Ala Ser
1               5                   10                  15

Lys Thr Phe His Ala Pro Leu Ile Ala Gly Thr Pro Gly Gln Glu Leu
            20                  25                  30

Ala Val Ile Ser Ser Ser Asp Glu Thr Lys Val Lys Ala Asp Trp Pro
        35                  40                  45

Thr Val Thr Val Val Ser Glu Pro Lys His Leu Phe Asn Asp Pro Asn
    50                  55                  60

Ile Asp Leu Ile Val Ile Pro Thr Pro Asn Asp Thr His Phe Pro Leu
65                  70                  75                  80

Ala Lys Ala Ala Leu Glu Ala Gly Lys His Val Val Asp Lys Pro
                85                  90                  95

Phe Thr Val Thr Leu Ser Gln Ala Arg Glu Leu Asp Ala Leu Ala Lys
            100                 105                 110

Ser Leu Gly Arg Val Leu Ser Val Phe His Asn Arg Arg Trp Asp Ser
        115                 120                 125

Asp Phe Leu Thr Leu Lys Gly Leu Leu Ala Glu Gly Val Leu Gly Glu
    130                 135                 140

Val Ala Tyr Phe Glu Ser His Phe Asp Arg Phe Arg Pro Gln Val Arg
145                 150                 155                 160

Asp Arg Trp Arg Glu Gln Gly Gly Pro Gly Ser Gly Ile Trp Tyr Asp
                165                 170                 175

Leu Ala Pro His Leu Leu Asp Gln Ala Ile Thr Leu Phe Gly Leu Pro
            180                 185                 190
```

```
Val Ser Met Thr Val Asp Leu Ala Gln Leu Arg Pro Gly Ala Gln Ser
        195                 200                 205

Thr Asp Tyr Phe His Ala Ile Leu Ser Tyr Pro Gln Arg Arg Val Ile
    210                 215                 220

Leu His Gly Thr Met Leu Ala Ala Ala Glu Ser Ala Arg Tyr Ile Val
225                 230                 235                 240

His Gly Ser Arg Gly Ser Tyr Val Lys Tyr Gly Leu Asp Pro Gln Glu
                245                 250                 255

Glu Arg Leu Lys Asn Gly Glu Arg Leu Pro Gln Glu Asp Trp Gly Tyr
            260                 265                 270

Asp Met Arg Asp Gly Val Leu Thr Arg Val Gly Glu Glu Arg Val
        275                 280                 285

Glu Glu Thr Leu Leu Thr Val Pro Gly Asn Tyr Pro Ala Tyr Tyr Ala
    290                 295                 300

Ala Ile Arg Asp Ala Leu Asn Gly Asp Gly Glu Asn Pro Val Pro Ala
305                 310                 315                 320

Ser Gln Ala Ile Gln Val Met Glu Leu Ile Glu Leu Gly Ile Glu Ser
                325                 330                 335

Ala Lys His Arg Ala Thr Leu Cys Leu Ala
            340                 345

<210> SEQ ID NO 3
<211> LENGTH: 1170
<212> TYPE: DNA
<213> ORGANISM: Agrobacterium tumefacience
<220> FEATURE:
<221> NAME/KEY: CDS
<222> LOCATION: (1)..(1170)
<223> OTHER INFORMATION:

<400> SEQUENCE: 3 atg tcc tcc gct aca aag aaa ttc gat agt cgc cgt att cgt ctc ggt    48
Met Ser Ser Ala Thr Lys Lys Phe Asp Ser Arg Arg Ile Arg Leu Gly
1               5                   10                  15 atg gtc ggc ggc ggt cag ggc gcc ttc att ggc gcg gtg cat cgc atc    96
Met Val Gly Gly Gly Gln Gly Ala Phe Ile Gly Ala Val His Arg Ile
            20                  25                  30 gcg gcc cgg ctg gat gac cgt tac gag ctg gtg gcc gga gcg ctt tcc   144
Ala Ala Arg Leu Asp Asp Arg Tyr Glu Leu Val Ala Gly Ala Leu Ser
        35                  40                  45 tcc gat ccc gcg cgt gcc gcc gcc tcg gca aca ctg ctc ggc att gcg   192
Ser Asp Pro Ala Arg Ala Ala Ala Ser Ala Thr Leu Leu Gly Ile Ala
    50                  55                  60 ccg gag cgc tcc tat gcc tcg ttc gag gac atg gcg gcg act gag gcc   240
Pro Glu Arg Ser Tyr Ala Ser Phe Glu Asp Met Ala Ala Thr Glu Ala
65                  70                  75                  80 ggc cgg gag gat ggc atc gag gca gtc gcc atc gtc acc ccc aac cat   288
Gly Arg Glu Asp Gly Ile Glu Ala Val Ala Ile Val Thr Pro Asn His
                85                  90                  95 ctg cat ttt gcc ccg tcc aag gcc ttt ctc gaa gcc ggc atc cac gtc   336
Leu His Phe Ala Pro Ser Lys Ala Phe Leu Glu Ala Gly Ile His Val
            100                 105                 110 atc tgc gac aag ccg gtg acc gcg acg ctg gaa gaa gcg aag gca ctg   384
Ile Cys Asp Lys Pro Val Thr Ala Thr Leu Glu Glu Ala Lys Ala Leu
        115                 120                 125 gcc ggg atc gtc aga gcc tcg gat agc ctt ttc gtg ctg acg cat aac   432
Ala Gly Ile Val Arg Ala Ser Asp Ser Leu Phe Val Leu Thr His Asn
    130                 135                 140 tac acc ggt tac gcc atg ctg cgg cag atg cgc gag atg atc gct gaa   480
```

-continued

```
Tyr Thr Gly Tyr Ala Met Leu Arg Gln Met Arg Glu Met Ile Ala Glu
145                 150                 155                 160 ggc gcc att ggc aag ctg cgc cat gtc cag gcc gaa tat gcg cag gac       528
Gly Ala Ile Gly Lys Leu Arg His Val Gln Ala Glu Tyr Ala Gln Asp
                165                 170                 175 tgg ctg acc gaa gcg gtc gaa aaa acc ggc gca aaa ggt gcg gaa tgg       576
Trp Leu Thr Glu Ala Val Glu Lys Thr Gly Ala Lys Gly Ala Glu Trp
            180                 185                 190 cgc acc gac ccc agc cgc tcc ggt gcg ggc ggc gcc atc ggc gat atc       624
Arg Thr Asp Pro Ser Arg Ser Gly Ala Gly Gly Ala Ile Gly Asp Ile
        195                 200                 205 ggc act cac gcc ttc aac gct gct gcc ttt gtg acg ggt gaa atc ccc       672
Gly Thr His Ala Phe Asn Ala Ala Ala Phe Val Thr Gly Glu Ile Pro
    210                 215                 220 agc agt ctt tat gcg gat ctc acg tcg ttt gtg ccg ggc cgg cag ctg       720
Ser Ser Leu Tyr Ala Asp Leu Thr Ser Phe Val Pro Gly Arg Gln Leu
225                 230                 235                 240 gat gac agc gcc aat att ctt ttg cgt tac gac agt ggc gcc aag ggc       768
Asp Asp Ser Ala Asn Ile Leu Leu Arg Tyr Asp Ser Gly Ala Lys Gly
                245                 250                 255 atg ctc tgg gca agc cag atc gcg gtc ggc aat gaa aat gcg ctg tca       816
Met Leu Trp Ala Ser Gln Ile Ala Val Gly Asn Glu Asn Ala Leu Ser
            260                 265                 270 ctc cgg gtc tat ggc gac aag ggc ggg ctt gaa tgg cac cac cgg gtg       864
Leu Arg Val Tyr Gly Asp Lys Gly Gly Leu Glu Trp His His Arg Val
        275                 280                 285 ccg gac gag ctg tgg ttc acg ccc tat ggc gag ccg aag cgg ctg att       912
Pro Asp Glu Leu Trp Phe Thr Pro Tyr Gly Glu Pro Lys Arg Leu Ile
    290                 295                 300 acc cgc aac ggt gcg ggc gcg ggt gcc gct gca aac cgt gtc agt cgt       960
Thr Arg Asn Gly Ala Gly Ala Gly Ala Ala Ala Asn Arg Val Ser Arg
305                 310                 315                 320 gtg cca tcc ggg cac ccg gag gga tat ctc gag ggt ttt gcg acg att      1008
Val Pro Ser Gly His Pro Glu Gly Tyr Leu Glu Gly Phe Ala Thr Ile
                325                 330                 335 tac cgc gaa gcc gca gac gca atc atc gca aag agg gag gga gaa aca      1056
Tyr Arg Glu Ala Ala Asp Ala Ile Ile Ala Lys Arg Glu Gly Glu Thr
            340                 345                 350 gcc gcc ggg gag gtg att tac ccc ggc atg gag gac ggc ctt gcg ggt      1104
Ala Ala Gly Glu Val Ile Tyr Pro Gly Met Glu Asp Gly Leu Ala Gly
        355                 360                 365 ctc gca ttc atc gat gcg gcc gtt cgc tcc agc cag acc tcg acc tgg      1152
Leu Ala Phe Ile Asp Ala Ala Val Arg Ser Ser Gln Thr Ser Thr Trp
    370                 375                 380 gtc ggg atc gac atc tag                                              1170
Val Gly Ile Asp Ile
385
```

<210> SEQ ID NO 4
<211> LENGTH: 389
<212> TYPE: PRT
<213> ORGANISM: Agrobacterium tumefacience

<400> SEQUENCE: 4

```
Met Ser Ser Ala Thr Lys Lys Phe Asp Ser Arg Arg Ile Arg Leu Gly
1               5                   10                  15

Met Val Gly Gly Gly Gln Gly Ala Phe Ile Gly Ala Val His Arg Ile
            20                  25                  30

Ala Ala Arg Leu Asp Asp Arg Tyr Glu Leu Val Ala Gly Ala Leu Ser
        35                  40                  45
```

Ser Asp Pro Ala Arg Ala Ala Ser Ala Thr Leu Leu Gly Ile Ala
 50                  55                  60

Pro Glu Arg Ser Tyr Ala Ser Phe Glu Asp Met Ala Ala Thr Glu Ala
 65                  70                  75                  80

Gly Arg Glu Asp Gly Ile Glu Ala Val Ala Ile Val Thr Pro Asn His
                 85                  90                  95

Leu His Phe Ala Pro Ser Lys Ala Phe Leu Glu Ala Gly Ile His Val
            100                 105                 110

Ile Cys Asp Lys Pro Val Thr Ala Thr Leu Glu Glu Ala Lys Ala Leu
        115                 120                 125

Ala Gly Ile Val Arg Ala Ser Asp Ser Leu Phe Val Leu Thr His Asn
130                 135                 140

Tyr Thr Gly Tyr Ala Met Leu Arg Gln Met Arg Glu Met Ile Ala Glu
145                 150                 155                 160

Gly Ala Ile Gly Lys Leu Arg His Val Gln Ala Glu Tyr Ala Gln Asp
                165                 170                 175

Trp Leu Thr Glu Ala Val Glu Lys Thr Gly Ala Lys Gly Ala Glu Trp
            180                 185                 190

Arg Thr Asp Pro Ser Arg Ser Gly Ala Gly Ala Ile Gly Asp Ile
        195                 200                 205

Gly Thr His Ala Phe Asn Ala Ala Phe Val Thr Gly Glu Ile Pro
210                 215                 220

Ser Ser Leu Tyr Ala Asp Leu Thr Ser Phe Val Pro Gly Arg Gln Leu
225                 230                 235                 240

Asp Asp Ser Ala Asn Ile Leu Leu Arg Tyr Asp Ser Gly Ala Lys Gly
                245                 250                 255

Met Leu Trp Ala Ser Gln Ile Ala Val Gly Asn Glu Asn Ala Leu Ser
            260                 265                 270

Leu Arg Val Tyr Gly Asp Lys Gly Gly Leu Glu Trp His His Arg Val
        275                 280                 285

Pro Asp Glu Leu Trp Phe Thr Pro Tyr Gly Glu Pro Lys Arg Leu Ile
290                 295                 300

Thr Arg Asn Gly Ala Gly Ala Gly Ala Ala Ala Asn Arg Val Ser Arg
305                 310                 315                 320

Val Pro Ser Gly His Pro Glu Gly Tyr Leu Glu Gly Phe Ala Thr Ile
                325                 330                 335

Tyr Arg Glu Ala Ala Asp Ala Ile Ile Ala Lys Arg Glu Gly Glu Thr
            340                 345                 350

Ala Ala Gly Glu Val Ile Tyr Pro Gly Met Glu Asp Gly Leu Ala Gly
        355                 360                 365

Leu Ala Phe Ile Asp Ala Ala Val Arg Ser Ser Gln Thr Ser Thr Trp
370                 375                 380

Val Gly Ile Asp Ile
385

<210> SEQ ID NO 5
<211> LENGTH: 1188
<212> TYPE: DNA
<213> ORGANISM: Agrobacterium tumefacience
<220> FEATURE:
<221> NAME/KEY: CDS
<222> LOCATION: (1)..(1188)
<223> OTHER INFORMATION:

<400> SEQUENCE: 5

-continued

| | |
|---|---|
| atg gct att gaa gga aag aca acc gac gtg gcg aac aag cgg att cgc<br>Met Ala Ile Glu Gly Lys Thr Thr Asp Val Ala Asn Lys Arg Ile Arg<br>1                   5                      10                  15 | 48 |
| ctc ggc atg gtc ggc ggc ggt tcg ggc gca ttc atc ggc ggc gtt cat<br>Leu Gly Met Val Gly Gly Gly Ser Gly Ala Phe Ile Gly Gly Val His<br>                 20                     25                     30 | 96 |
| cgc atg gca gcg cgg ctc gac aat cgc ttc gat ctc gtg gcg ggg gcc<br>Arg Met Ala Ala Arg Leu Asp Asn Arg Phe Asp Leu Val Ala Gly Ala<br>            35                     40                     45 | 144 |
| ctg tcc tcg aca ccg gaa aaa tcc cta gct tcc ggg cgt gag ctg ggg<br>Leu Ser Ser Thr Pro Glu Lys Ser Leu Ala Ser Gly Arg Glu Leu Gly<br>50                      55                     60 | 192 |
| ctc gac tct gag cgt tgc tac ggc tcg ttt gaa gaa atg gcc gaa aaa<br>Leu Asp Ser Glu Arg Cys Tyr Gly Ser Phe Glu Glu Met Ala Glu Lys<br>65                      70                     75                  80 | 240 |
| gaa gcg ctg cgc gag gat ggt atc gag gcg gtg gcg atc gtc acc ccc<br>Glu Ala Leu Arg Glu Asp Gly Ile Glu Ala Val Ala Ile Val Thr Pro<br>                         85                     90                     95 | 288 |
| aac cat gtg cac tat ccc gct gca aag gcc ttc ctg gag cgc ggc atc<br>Asn His Val His Tyr Pro Ala Ala Lys Ala Phe Leu Glu Arg Gly Ile<br>                    100                   105                 110 | 336 |
| cat gtc atc tgc gac aag ccg ctg act tcc aat ctc gaa gac gcg aaa<br>His Val Ile Cys Asp Lys Pro Leu Thr Ser Asn Leu Glu Asp Ala Lys<br>              115                   120                 125 | 384 |
| aag ctg aag gac gtg gcc gat aag gcc gat gcg ctg ttc atc ctg acg<br>Lys Leu Lys Asp Val Ala Asp Lys Ala Asp Ala Leu Phe Ile Leu Thr<br>130                     135                   140 | 432 |
| cat aac tac acc ggt tat cca atg gtg cgg cat gcg cgc gag ctg gtg<br>His Asn Tyr Thr Gly Tyr Pro Met Val Arg His Ala Arg Glu Leu Val<br>145                     150                   155                 160 | 480 |
| gag gcc ggt gca ctc ggc aat atc cgt ctg gtg caa atg gaa tat ccg<br>Glu Ala Gly Ala Leu Gly Asn Ile Arg Leu Val Gln Met Glu Tyr Pro<br>                    165                   170                 175 | 528 |
| cag gac tgg ctg acg gag gcg gtg gaa cag acc ggc gcg aaa cag gca<br>Gln Asp Trp Leu Thr Glu Ala Val Glu Gln Thr Gly Ala Lys Gln Ala<br>              180                   185                 190 | 576 |
| gtc tgg cgt acc gat ccg gcc caa tct ggc gtt ggc ggt tcc acc ggt<br>Val Trp Arg Thr Asp Pro Ala Gln Ser Gly Val Gly Gly Ser Thr Gly<br>195                     200                   205 | 624 |
| gac atc ggc acc cat gcc tat aat ctc ggc tgc ttc att tcc ggt ctc<br>Asp Ile Gly Thr His Ala Tyr Asn Leu Gly Cys Phe Ile Ser Gly Leu<br>210                     215                   220 | 672 |
| gaa gcg gat gag ctg gcg gcg gat gtg cat acc ttc gtc gaa ggc cgt<br>Glu Ala Asp Glu Leu Ala Ala Asp Val His Thr Phe Val Glu Gly Arg<br>225                     230                   235                 240 | 720 |
| cgg ctc gat gac aat gct cat gtg atg atg cgc ttc aag ccc aag ggc<br>Arg Leu Asp Asp Asn Ala His Val Met Met Arg Phe Lys Pro Lys Gly<br>                    245                   250                 255 | 768 |
| ggc aag caa ccc gcc agg ggc atg ctc tgg tgc agc cag gtg gca gtc<br>Gly Lys Gln Pro Ala Arg Gly Met Leu Trp Cys Ser Gln Val Ala Val<br>              260                   265                 270 | 816 |
| ggc cat gaa aat ggg ctg aag atc cgc ctt tat ggc gac aag gcc ggt<br>Gly His Glu Asn Gly Leu Lys Ile Arg Leu Tyr Gly Asp Lys Ala Gly<br>            275                   280                 285 | 864 |
| ctc gaa tgg acg cag gcc gat ccg aat tat ctg tgg ttt acg aag ctc<br>Leu Glu Trp Thr Gln Ala Asp Pro Asn Tyr Leu Trp Phe Thr Lys Leu<br>290                     295                   300 | 912 |
| ggc gaa ccg aag cag ttg atc acc cgc ggg ggc ggg gca ggg gcc<br>Gly Glu Pro Lys Gln Leu Ile Thr Arg Gly Gly Ala Gly Ala Gly Ala<br>305                     310                   315                 320 | 960 |

```
gca gcc gct cgc gtt acc cgc ata ccc tcc ggc cat ccg gaa gga tat    1008
Ala Ala Ala Arg Val Thr Arg Ile Pro Ser Gly His Pro Glu Gly Tyr
                325                 330                 335 ctg gaa gcc ttc gct acc atc tat acc gag gct gcg cat gcc att gag    1056
Leu Glu Ala Phe Ala Thr Ile Tyr Thr Glu Ala Ala His Ala Ile Glu
            340                 345                 350 gcg cgc cgc acc ggt tcg gcg ctg gat aag gcg gtc atc tat ccg acg    1104
Ala Arg Arg Thr Gly Ser Ala Leu Asp Lys Ala Val Ile Tyr Pro Thr
        355                 360                 365 gtg gat gac ggc gtc aaa ggt gtg gcc ttc gtc acg gcc tgc atc gag    1152
Val Asp Asp Gly Val Lys Gly Val Ala Phe Val Thr Ala Cys Ile Glu
370                 375                 380 tca ggc aag aag aat ggc ggc tgg gtg aag ctg taa                    1188
Ser Gly Lys Lys Asn Gly Gly Trp Val Lys Leu
385                 390                 395

<210> SEQ ID NO 6
<211> LENGTH: 395
<212> TYPE: PRT
<213> ORGANISM: Agrobacterium tumefacience

<400> SEQUENCE: 6

Met Ala Ile Glu Gly Lys Thr Thr Asp Val Ala Asn Lys Arg Ile Arg
1               5                   10                  15

Leu Gly Met Val Gly Gly Gly Ser Gly Ala Phe Ile Gly Gly Val His
            20                  25                  30

Arg Met Ala Ala Arg Leu Asp Asn Arg Phe Asp Leu Val Ala Gly Ala
        35                  40                  45

Leu Ser Ser Thr Pro Glu Lys Ser Leu Ala Ser Gly Arg Glu Leu Gly
    50                  55                  60

Leu Asp Ser Glu Arg Cys Tyr Gly Ser Phe Glu Met Ala Glu Lys
65                  70                  75                  80

Glu Ala Leu Arg Glu Asp Gly Ile Glu Ala Val Ala Ile Val Thr Pro
                85                  90                  95

Asn His Val His Tyr Pro Ala Ala Lys Ala Phe Leu Glu Arg Gly Ile
            100                 105                 110

His Val Ile Cys Asp Lys Pro Leu Thr Ser Asn Leu Glu Asp Ala Lys
        115                 120                 125

Lys Leu Lys Asp Val Ala Asp Lys Ala Asp Ala Leu Phe Ile Leu Thr
    130                 135                 140

His Asn Tyr Thr Gly Tyr Pro Met Val Arg His Ala Arg Glu Leu Val
145                 150                 155                 160

Glu Ala Gly Ala Leu Gly Asn Ile Arg Leu Val Gln Met Glu Tyr Pro
                165                 170                 175

Gln Asp Trp Leu Thr Glu Ala Val Glu Gln Thr Gly Ala Lys Gln Ala
            180                 185                 190

Val Trp Arg Thr Asp Pro Ala Gln Ser Gly Val Gly Ser Thr Gly
        195                 200                 205

Asp Ile Gly Thr His Ala Tyr Asn Leu Gly Cys Phe Ile Ser Gly Leu
    210                 215                 220

Glu Ala Asp Glu Leu Ala Ala Asp Val His Thr Phe Val Glu Gly Arg
225                 230                 235                 240

Arg Leu Asp Asp Asn Ala His Val Met Met Arg Phe Lys Pro Lys Gly
                245                 250                 255

Gly Lys Gln Pro Ala Arg Gly Met Leu Trp Cys Ser Gln Val Ala Val
            260                 265                 270
```

```
Gly His Glu Asn Gly Leu Lys Ile Arg Leu Tyr Gly Asp Lys Ala Gly
            275                 280                 285

Leu Glu Trp Thr Gln Ala Asp Pro Asn Tyr Leu Trp Phe Thr Lys Leu
        290                 295                 300

Gly Glu Pro Lys Gln Leu Ile Thr Arg Gly Ala Gly Ala Gly Ala
305                 310                 315                 320

Ala Ala Ala Arg Val Thr Arg Ile Pro Ser Gly His Pro Glu Gly Tyr
                325                 330                 335

Leu Glu Ala Phe Ala Thr Ile Tyr Thr Glu Ala Ala His Ala Ile Glu
            340                 345                 350

Ala Arg Arg Thr Gly Ser Ala Leu Asp Lys Ala Val Ile Tyr Pro Thr
        355                 360                 365

Val Asp Asp Gly Val Lys Gly Val Ala Phe Val Thr Ala Cys Ile Glu
    370                 375                 380

Ser Gly Lys Lys Asn Gly Gly Trp Val Lys Leu
385                 390                 395
```

<210> SEQ ID NO 7
<211> LENGTH: 1077
<212> TYPE: DNA
<213> ORGANISM: Bacillus subtilis
<220> FEATURE:
<221> NAME/KEY: CDS
<222> LOCATION: (1)..(1077)
<223> OTHER INFORMATION:

<400> SEQUENCE: 7

```
ttg ata acg ctt tta aag ggg aga aga aaa gtg gat acg atc aag gtt    48
Met Ile Thr Leu Leu Lys Gly Arg Arg Lys Val Asp Thr Ile Lys Val
1               5                   10                  15 gga ata tta gga tac gga ttg tcc ggt tct gtt ttt cac ggg ccg ctg    96
Gly Ile Leu Gly Tyr Gly Leu Ser Gly Ser Val Phe His Gly Pro Leu
            20                  25                  30 ctg gat gtt ctg gat gaa tat caa atc agc aaa atc atg aca tca cgg   144
Leu Asp Val Leu Asp Glu Tyr Gln Ile Ser Lys Ile Met Thr Ser Arg
        35                  40                  45 aca gaa gaa gtg aaa cgg gat ttt cca gat gct gag gtt gta cat gag   192
Thr Glu Glu Val Lys Arg Asp Phe Pro Asp Ala Glu Val Val His Glu
    50                  55                  60 ctt gaa gaa atc aca aat gac cct gcc att gag ctt gtc att gtc acc   240
Leu Glu Glu Ile Thr Asn Asp Pro Ala Ile Glu Leu Val Ile Val Thr
65                  70                  75                  80 acc ccg agc ggc ctt cat tac gag cat act atg gca tgc ata cag gcc   288
Thr Pro Ser Gly Leu His Tyr Glu His Thr Met Ala Cys Ile Gln Ala
                85                  90                  95 gga aaa cat gtt gtg atg gaa aaa cca atg aca gca acg gcc gaa gag   336
Gly Lys His Val Val Met Glu Lys Pro Met Thr Ala Thr Ala Glu Glu
            100                 105                 110 ggg gaa aca tta aaa agg gct gcc gat gaa aaa ggc gta tta tta agc   384
Gly Glu Thr Leu Lys Arg Ala Ala Asp Glu Lys Gly Val Leu Leu Ser
        115                 120                 125 gta tat cat aac cga cgc tgg gat aac gat ttt tta acg att aaa aag   432
Val Tyr His Asn Arg Arg Trp Asp Asn Asp Phe Leu Thr Ile Lys Lys
    130                 135                 140 ctg atc tct gag gga tcc ctt gaa gat atc aat aca tat caa gtt tcc   480
Leu Ile Ser Glu Gly Ser Leu Glu Asp Ile Asn Thr Tyr Gln Val Ser
145                 150                 155                 160 tat aac cgc tac aga cct gaa gtt caa gcg cgg tgg cgg gaa aaa gaa   528
Tyr Asn Arg Tyr Arg Pro Glu Val Gln Ala Arg Trp Arg Glu Lys Glu
```

```
                    165                 170                 175
ggc act gcc act ggt acg ctg tat gat ctc ggc tcc cac atc ata gac    576
Gly Thr Ala Thr Gly Thr Leu Tyr Asp Leu Gly Ser His Ile Ile Asp
            180                 185                 190 caa acc ctg cat ttg ttt ggg atg cct aaa gcc gtg act gca aac gtg    624
Gln Thr Leu His Leu Phe Gly Met Pro Lys Ala Val Thr Ala Asn Val
                195                 200                 205 atg gcc cag cgg gaa aat gcc gaa acg gtt gac tat ttt cat tta acc    672
Met Ala Gln Arg Glu Asn Ala Glu Thr Val Asp Tyr Phe His Leu Thr
    210                 215                 220 ctg gat tat ggc aag ctt caa gcc att cta tac gga gga tca atc gtt    720
Leu Asp Tyr Gly Lys Leu Gln Ala Ile Leu Tyr Gly Gly Ser Ile Val
225                 230                 235                 240 ccg gca aac gga cct cgt tat caa atc cat gga aaa gat tct agc ttt    768
Pro Ala Asn Gly Pro Arg Tyr Gln Ile His Gly Lys Asp Ser Ser Phe
                245                 250                 255 atc aaa tat gga att gac gga cag gaa gac gca ctc aga gcg gga aga    816
Ile Lys Tyr Gly Ile Asp Gly Gln Glu Asp Ala Leu Arg Ala Gly Arg
            260                 265                 270 aaa cca gag gat gac agc tgg ggt gcg gat gtt ccg gag ttt tac gga    864
Lys Pro Glu Asp Asp Ser Trp Gly Ala Asp Val Pro Glu Phe Tyr Gly
        275                 280                 285 aag ctt aca acc att cgt ggc tcc gac aaa aaa aca gaa acg att cca    912
Lys Leu Thr Thr Ile Arg Gly Ser Asp Lys Lys Thr Glu Thr Ile Pro
    290                 295                 300 tca gta aat ggc tcc tac ctt act tat tac cgt aaa ata gcg gaa agc    960
Ser Val Asn Gly Ser Tyr Leu Thr Tyr Tyr Arg Lys Ile Ala Glu Ser
305                 310                 315                 320 ata cga gaa ggt gct gcg ctg cca gtc act gct gag gaa ggt att aat   1008
Ile Arg Glu Gly Ala Ala Leu Pro Val Thr Ala Glu Glu Gly Ile Asn
                325                 330                 335 gtc atc cgc atc att gaa gcc gcg atg gaa agc agt aaa gag aaa cga   1056
Val Ile Arg Ile Ile Glu Ala Ala Met Glu Ser Ser Lys Glu Lys Arg
            340                 345                 350 acc att atg ctg gag cac taa                                       1077
Thr Ile Met Leu Glu His
        355

<210> SEQ ID NO 8
<211> LENGTH: 358
<212> TYPE: PRT
<213> ORGANISM: Bacillus subtilis

<400> SEQUENCE: 8

Met Ile Thr Leu Leu Lys Gly Arg Arg Lys Val Asp Thr Ile Lys Val
1               5                   10                  15

Gly Ile Leu Gly Tyr Gly Leu Ser Gly Ser Val Phe His Gly Pro Leu
            20                  25                  30

Leu Asp Val Leu Asp Glu Tyr Gln Ile Ser Lys Ile Met Thr Ser Arg
        35                  40                  45

Thr Glu Glu Val Lys Arg Asp Phe Pro Asp Ala Glu Val Val His Glu
    50                  55                  60

Leu Glu Glu Ile Thr Asn Asp Pro Ala Ile Glu Leu Val Ile Val Thr
65                  70                  75                  80

Thr Pro Ser Gly Leu His Tyr Glu His Thr Met Ala Cys Ile Gln Ala
                85                  90                  95

Gly Lys His Val Val Met Glu Lys Pro Met Thr Ala Thr Ala Glu Glu
            100                 105                 110
```

```
Gly Glu Thr Leu Lys Arg Ala Ala Asp Glu Lys Gly Val Leu Leu Ser
        115                 120                 125

Val Tyr His Asn Arg Arg Trp Asp Asn Asp Phe Leu Thr Ile Lys Lys
130                 135                 140

Leu Ile Ser Glu Gly Ser Leu Glu Asp Ile Asn Thr Tyr Gln Val Ser
145                 150                 155                 160

Tyr Asn Arg Tyr Arg Pro Glu Val Gln Ala Arg Trp Arg Glu Lys Glu
                165                 170                 175

Gly Thr Ala Thr Gly Thr Leu Tyr Asp Leu Gly Ser His Ile Ile Asp
            180                 185                 190

Gln Thr Leu His Leu Phe Gly Met Pro Lys Ala Val Thr Ala Asn Val
        195                 200                 205

Met Ala Gln Arg Glu Asn Ala Glu Thr Val Asp Tyr Phe His Leu Thr
    210                 215                 220

Leu Asp Tyr Gly Lys Leu Gln Ala Ile Leu Tyr Gly Ser Ile Val
225                 230                 235                 240

Pro Ala Asn Gly Pro Arg Tyr Gln Ile His Gly Lys Asp Ser Ser Phe
                245                 250                 255

Ile Lys Tyr Gly Ile Asp Gly Gln Asp Ala Leu Arg Ala Gly Arg
            260                 265                 270

Lys Pro Glu Asp Asp Ser Trp Gly Ala Asp Val Pro Glu Phe Tyr Gly
        275                 280                 285

Lys Leu Thr Thr Ile Arg Gly Ser Asp Lys Lys Thr Glu Thr Ile Pro
    290                 295                 300

Ser Val Asn Gly Ser Tyr Leu Thr Tyr Tyr Arg Lys Ile Ala Glu Ser
305                 310                 315                 320

Ile Arg Glu Gly Ala Ala Leu Pro Val Thr Ala Glu Glu Gly Ile Asn
                325                 330                 335

Val Ile Arg Ile Ile Glu Ala Ala Met Glu Ser Ser Lys Glu Lys Arg
            340                 345                 350

Thr Ile Met Leu Glu His
        355

<210> SEQ ID NO 9
<211> LENGTH: 1170
<212> TYPE: DNA
<213> ORGANISM: Agrobacterium sp.
<220> FEATURE:
<221> NAME/KEY: CDS
<222> LOCATION: (1)..(1170)
<223> OTHER INFORMATION:

<400> SEQUENCE: 9 atg tcc tcc gca cca aaa aaa ttc gac agc cgc cgt atc cgt ctc gga      48
Met Ser Ser Ala Pro Lys Lys Phe Asp Ser Arg Arg Ile Arg Leu Gly
1               5                   10                  15 atg gtc ggc ggc ggt cag ggc gcc ttt atc ggt gcg gtg cac cgc ata      96
Met Val Gly Gly Gly Gln Gly Ala Phe Ile Gly Ala Val His Arg Ile
            20                  25                  30 gcg gcc cgg ctg gat gac cgt tac gag ctc gtg gcc gga gcg ctt tcc     144
Ala Ala Arg Leu Asp Asp Arg Tyr Glu Leu Val Ala Gly Ala Leu Ser
        35                  40                  45 tcc gat ccc gcg cgt gcg gcc gct tcg gca acc ctg ctc ggc atc gcg     192
Ser Asp Pro Ala Arg Ala Ala Ala Ser Ala Thr Leu Leu Gly Ile Ala
    50                  55                  60 ccg gag cgt tcc tat gcc tca ttc gag gag atg gct gcg gca gag gcc     240
Pro Glu Arg Ser Tyr Ala Ser Phe Glu Glu Met Ala Ala Ala Glu Ala
65                  70                  75                  80
```

```
ggt cga gac gac ggt atc gag gca gtc gcc atc gtg acg ccc aat cac    288
Gly Arg Asp Asp Gly Ile Glu Ala Val Ala Ile Val Thr Pro Asn His
             85                  90                  95 ctc cat ttt gcg ccc tca aag gcc ttt ctc gag gcc ggt att cac gtc    336
Leu His Phe Ala Pro Ser Lys Ala Phe Leu Glu Ala Gly Ile His Val
            100                 105                 110 atc tgc gac aag cct gtg acc gcg aca ctt gag gaa gca aag gcg ctg    384
Ile Cys Asp Lys Pro Val Thr Ala Thr Leu Glu Glu Ala Lys Ala Leu
        115                 120                 125 gcc gag atc gtc agg gcg tcg gac agc ctg ttt gtc ctg acg cat aat    432
Ala Glu Ile Val Arg Ala Ser Asp Ser Leu Phe Val Leu Thr His Asn
    130                 135                 140 tac acc ggc tac gcc atg ctg cgg cag atg cgg cag atg gtg gct gat    480
Tyr Thr Gly Tyr Ala Met Leu Arg Gln Met Arg Gln Met Val Ala Asp
145                 150                 155                 160 gga gcc att ggc aag ctg cgc cac gtt cag gcc gaa tat gcc cag gac    528
Gly Ala Ile Gly Lys Leu Arg His Val Gln Ala Glu Tyr Ala Gln Asp
                165                 170                 175 tgg ctg acc gag gcg gtt gag aag acc ggt gcg aag ggg gcg gaa tgg    576
Trp Leu Thr Glu Ala Val Glu Lys Thr Gly Ala Lys Gly Ala Glu Trp
            180                 185                 190 cgc acc gat ccc agc cgc tcc ggc gcg ggc ggg gcc atc ggc gat atc    624
Arg Thr Asp Pro Ser Arg Ser Gly Ala Gly Gly Ala Ile Gly Asp Ile
        195                 200                 205 ggc acc cac gcc ttc aac gct gcc gcc ttc gtt acc ggt gaa atc ccg    672
Gly Thr His Ala Phe Asn Ala Ala Ala Phe Val Thr Gly Glu Ile Pro
    210                 215                 220 aag agt ctt tat gcc gac ctg acc tct ttc gtg ccg ggc cgg cag ctg    720
Lys Ser Leu Tyr Ala Asp Leu Thr Ser Phe Val Pro Gly Arg Gln Leu
225                 230                 235                 240 gat gac agc gcc aat att ctt ttg cgt tac gaa agc ggc gcc aag ggc    768
Asp Asp Ser Ala Asn Ile Leu Leu Arg Tyr Glu Ser Gly Ala Lys Gly
                245                 250                 255 atg ctt tgg gca agc cag atc gca gtc ggc aat gaa aac gcg ctg tcg    816
Met Leu Trp Ala Ser Gln Ile Ala Val Gly Asn Glu Asn Ala Leu Ser
            260                 265                 270 ctg cgg gtc tac ggc gaa aag ggc ggg ctt gaa tgg cac cac cgc gtg    864
Leu Arg Val Tyr Gly Glu Lys Gly Gly Leu Glu Trp His His Arg Val
        275                 280                 285 ccg gat gag ctg tgg ttc acc cct tac ggc gag ccg aag cgg ctc ata    912
Pro Asp Glu Leu Trp Phe Thr Pro Tyr Gly Glu Pro Lys Arg Leu Ile
    290                 295                 300 acc cgc aac ggc gca ggc gca gga gcc gcg gcc aac cgt gtc agc cgc    960
Thr Arg Asn Gly Ala Gly Ala Gly Ala Ala Ala Asn Arg Val Ser Arg
305                 310                 315                 320 gtg cca tcg ggg cac ccg gaa gga tac ctc gag ggt ttc gcg acg atc   1008
Val Pro Ser Gly His Pro Glu Gly Tyr Leu Glu Gly Phe Ala Thr Ile
                325                 330                 335 tac cgc gaa gcc gca gat gca atc att gcc aaa agg gag gga aaa gca   1056
Tyr Arg Glu Ala Ala Asp Ala Ile Ile Ala Lys Arg Glu Gly Lys Ala
            340                 345                 350 gcc gcc ggg gag gtg att tac ccc ggc atg gag gac ggc ctt gcg ggt   1104
Ala Ala Gly Glu Val Ile Tyr Pro Gly Met Glu Asp Gly Leu Ala Gly
        355                 360                 365 ctc gca ttc atc gat gcc gcc gtt cgc tcc agc cag acc tcg acc tgg   1152
Leu Ala Phe Ile Asp Ala Ala Val Arg Ser Ser Gln Thr Ser Thr Trp
    370                 375                 380 atc aat atc gat atc tag                                           1170
Ile Asn Ile Asp Ile
```

<210> SEQ ID NO 10
<211> LENGTH: 389
<212> TYPE: PRT
<213> ORGANISM: Agrobacterium sp.

<400> SEQUENCE: 10

| | | | | | | | | | | | | | | | |
|---|---|---|---|---|---|---|---|---|---|---|---|---|---|---|---|
| Met | Ser | Ser | Ala | Pro | Lys | Lys | Phe | Asp | Ser | Arg | Arg | Ile | Arg | Leu | Gly |
| 1 | | | | 5 | | | | | 10 | | | | | 15 | |
| Met | Val | Gly | Gly | Gly | Gln | Gly | Ala | Phe | Ile | Gly | Ala | Val | His | Arg | Ile |
| | | | 20 | | | | | 25 | | | | | 30 | | |
| Ala | Ala | Arg | Leu | Asp | Asp | Arg | Tyr | Glu | Leu | Val | Ala | Gly | Ala | Leu | Ser |
| | | | 35 | | | | | 40 | | | | | 45 | | |
| Ser | Asp | Pro | Ala | Arg | Ala | Ala | Ser | Ala | Thr | Leu | Leu | Gly | Ile | Ala | |
| | 50 | | | | | 55 | | | | | 60 | | | | |
| Pro | Glu | Arg | Ser | Tyr | Ala | Ser | Phe | Glu | Glu | Met | Ala | Ala | Ala | Glu | Ala |
| 65 | | | | | 70 | | | | | 75 | | | | | 80 |
| Gly | Arg | Asp | Asp | Gly | Ile | Glu | Ala | Val | Ala | Ile | Val | Thr | Pro | Asn | His |
| | | | | 85 | | | | | 90 | | | | | 95 | |
| Leu | His | Phe | Ala | Pro | Ser | Lys | Ala | Phe | Leu | Glu | Ala | Gly | Ile | His | Val |
| | | | 100 | | | | | 105 | | | | | 110 | | |
| Ile | Cys | Asp | Lys | Pro | Val | Thr | Ala | Thr | Leu | Glu | Glu | Ala | Lys | Ala | Leu |
| | | | 115 | | | | | 120 | | | | | 125 | | |
| Ala | Glu | Ile | Val | Arg | Ala | Ser | Asp | Ser | Leu | Phe | Val | Leu | Thr | His | Asn |
| | 130 | | | | | 135 | | | | | 140 | | | | |
| Tyr | Thr | Gly | Tyr | Ala | Met | Leu | Arg | Gln | Met | Arg | Gln | Met | Val | Ala | Asp |
| 145 | | | | | 150 | | | | | 155 | | | | | 160 |
| Gly | Ala | Ile | Gly | Lys | Leu | Arg | His | Val | Gln | Ala | Glu | Tyr | Ala | Gln | Asp |
| | | | | 165 | | | | | 170 | | | | | 175 | |
| Trp | Leu | Thr | Glu | Ala | Val | Glu | Lys | Thr | Gly | Ala | Lys | Gly | Ala | Glu | Trp |
| | | | 180 | | | | | 185 | | | | | 190 | | |
| Arg | Thr | Asp | Pro | Ser | Arg | Ser | Gly | Ala | Gly | Gly | Ala | Ile | Gly | Asp | Ile |
| | | | 195 | | | | | 200 | | | | | 205 | | |
| Gly | Thr | His | Ala | Phe | Asn | Ala | Ala | Ala | Phe | Val | Thr | Gly | Glu | Ile | Pro |
| | 210 | | | | | 215 | | | | | 220 | | | | |
| Lys | Ser | Leu | Tyr | Ala | Asp | Leu | Thr | Ser | Phe | Val | Pro | Gly | Arg | Gln | Leu |
| 225 | | | | | 230 | | | | | 235 | | | | | 240 |
| Asp | Asp | Ser | Ala | Asn | Ile | Leu | Leu | Arg | Tyr | Glu | Ser | Gly | Ala | Lys | Gly |
| | | | | 245 | | | | | 250 | | | | | 255 | |
| Met | Leu | Trp | Ala | Ser | Gln | Ile | Ala | Val | Gly | Asn | Glu | Asn | Ala | Leu | Ser |
| | | | 260 | | | | | 265 | | | | | 270 | | |
| Leu | Arg | Val | Tyr | Gly | Glu | Lys | Gly | Gly | Leu | Glu | Trp | His | His | Arg | Val |
| | | | 275 | | | | | 280 | | | | | 285 | | |
| Pro | Asp | Glu | Leu | Trp | Phe | Thr | Pro | Tyr | Gly | Glu | Pro | Lys | Arg | Leu | Ile |
| | 290 | | | | | 295 | | | | | 300 | | | | |
| Thr | Arg | Asn | Gly | Ala | Gly | Ala | Gly | Ala | Ala | Asn | Arg | Val | Ser | Arg | |
| 305 | | | | | 310 | | | | | 315 | | | | | 320 |
| Val | Pro | Ser | Gly | His | Pro | Glu | Gly | Tyr | Leu | Glu | Gly | Phe | Ala | Thr | Ile |
| | | | | 325 | | | | | 330 | | | | | 335 | |
| Tyr | Arg | Glu | Ala | Ala | Asp | Ala | Ile | Ile | Ala | Lys | Arg | Glu | Gly | Lys | Ala |
| | | | 340 | | | | | 345 | | | | | 350 | | |
| Ala | Ala | Gly | Glu | Val | Ile | Tyr | Pro | Gly | Met | Glu | Asp | Gly | Leu | Ala | Gly |
| | | | 355 | | | | | 360 | | | | | 365 | | |

```
Leu Ala Phe Ile Asp Ala Ala Val Arg Ser Ser Gln Thr Ser Thr Trp
    370                 375                 380

Ile Asn Ile Asp Ile
385

<210> SEQ ID NO 11
<211> LENGTH: 1188
<212> TYPE: DNA
<213> ORGANISM: Agrobacterium sp.
<220> FEATURE:
<221> NAME/KEY: CDS
<222> LOCATION: (1)..(1188)
<223> OTHER INFORMATION:

<400> SEQUENCE: 11 atg gct att gaa gga aag aca acc gac aag gcg aac aag cgg att cgc      48
Met Ala Ile Glu Gly Lys Thr Thr Asp Lys Ala Asn Lys Arg Ile Arg
1               5                   10                  15 ctc ggc atg gtg ggc ggt ggt tct ggt gcc ttt atc ggt ggt gtt cac      96
Leu Gly Met Val Gly Gly Gly Ser Gly Ala Phe Ile Gly Gly Val His
                20                  25                  30 cgc atg gcg gcg cgg ctc gac aat cgt ttc gat ctc gtg gca ggg gcg     144
Arg Met Ala Ala Arg Leu Asp Asn Arg Phe Asp Leu Val Ala Gly Ala
            35                  40                  45 ctg tct tcg acc ccg gaa aaa tcc ctc gcc tcc ggc cgt gaa ctg ggg     192
Leu Ser Ser Thr Pro Glu Lys Ser Leu Ala Ser Gly Arg Glu Leu Gly
        50                  55                  60 ctc gat ccc gag cgt tgc tac ggc tcg ttc gag gag atg gcc gaa aag     240
Leu Asp Pro Glu Arg Cys Tyr Gly Ser Phe Glu Glu Met Ala Glu Lys
65                  70                  75                  80 gag gcg cta cgc gag gat ggc ata gag gcg gtg gcg atc gtc acg ccc     288
Glu Ala Leu Arg Glu Asp Gly Ile Glu Ala Val Ala Ile Val Thr Pro
                85                  90                  95 aac cac gtg cat tat ccg gcg gcg aag gcg ttt ctg gag cgt ggc atc     336
Asn His Val His Tyr Pro Ala Ala Lys Ala Phe Leu Glu Arg Gly Ile
                100                 105                 110 cat gtc atc tgc gac aag ccg ctg acc tcc aat ctg gaa gac gcg aag     384
His Val Ile Cys Asp Lys Pro Leu Thr Ser Asn Leu Glu Asp Ala Lys
            115                 120                 125 aag ctg aag gac gtc gcc gac aag gcc gat gcg ctg ttc atc ctg acg     432
Lys Leu Lys Asp Val Ala Asp Lys Ala Asp Ala Leu Phe Ile Leu Thr
        130                 135                 140 cat aat tac acc ggc tat ccg atg gtg cgg cat gca cgg gaa ctg gtg     480
His Asn Tyr Thr Gly Tyr Pro Met Val Arg His Ala Arg Glu Leu Val
145                 150                 155                 160 gaa tcg ggc gct ctc ggc acg atc cgt ctg gtg cag atg gag tat ccg     528
Glu Ser Gly Ala Leu Gly Thr Ile Arg Leu Val Gln Met Glu Tyr Pro
                165                 170                 175 cag gac tgg ctg gcg gaa ccc atc gag cag acg ggc gcc aaa cag gct     576
Gln Asp Trp Leu Ala Glu Pro Ile Glu Gln Thr Gly Ala Lys Gln Ala
            180                 185                 190 gtc tgg cgc acc gac ccg gcc caa tcc ggt gcg ggt ggt tcc aca ggc     624
Val Trp Arg Thr Asp Pro Ala Gln Ser Gly Ala Gly Gly Ser Thr Gly
        195                 200                 205 gat atc ggc acg cat gcc tat aat ctc ggc tgc ttc att tcc ggt ctg     672
Asp Ile Gly Thr His Ala Tyr Asn Leu Gly Cys Phe Ile Ser Gly Leu
210                 215                 220 gaa gtc gac gaa ctg gcg gca gat gtg cat acc ttt gtc gaa ggc cgc     720
Glu Val Asp Glu Leu Ala Ala Asp Val His Thr Phe Val Glu Gly Arg
225                 230                 235                 240 cgg ctg gac gac aat gcg cat gtg atg ctg cgt ttc aag ccg aag ggt     768
```

```
Arg Leu Asp Asp Asn Ala His Val Met Leu Arg Phe Lys Pro Lys Gly
                245                 250                 255 ggc aag cag ccg gca aag ggg ctg ctc tgg tgc agc cag gtt gcg gtc      816
Gly Lys Gln Pro Ala Lys Gly Leu Leu Trp Cys Ser Gln Val Ala Val
            260                 265                 270 ggc cac gaa aac ggc ctg aaa gtt cgt gtg tat ggt gac aag gcc ggc      864
Gly His Glu Asn Gly Leu Lys Val Arg Val Tyr Gly Asp Lys Ala Gly
        275                 280                 285 atc gaa tgg acg cag gcc gac ccg aac tat ctc tgg ttc acg aag ctt      912
Ile Glu Trp Thr Gln Ala Asp Pro Asn Tyr Leu Trp Phe Thr Lys Leu
    290                 295                 300 ggc gag ctg aag cag ttg atc acc cgc ggc ggt gcc ggg gca ggg gct      960
Gly Glu Leu Lys Gln Leu Ile Thr Arg Gly Gly Ala Gly Ala Gly Ala
305                 310                 315                 320 gcc gca gca cgc gtc acc cgc atc cct tcc ggc cac ccg gaa ggt tat     1008
Ala Ala Ala Arg Val Thr Arg Ile Pro Ser Gly His Pro Glu Gly Tyr
                325                 330                 335 ctc gaa gcc ttc gca acg atc tat acc gag gcg gcg cat gcc atc gaa     1056
Leu Glu Ala Phe Ala Thr Ile Tyr Thr Glu Ala Ala His Ala Ile Glu
            340                 345                 350 gcc cgc cgc acc ggc tcg gtg ctc gac aag gcc gtg att tac ccg acc     1104
Ala Arg Arg Thr Gly Ser Val Leu Asp Lys Ala Val Ile Tyr Pro Thr
        355                 360                 365 gtc gat gat ggc gta aag ggt gtc gcc ttt gtt acg gcc tgc atc gag     1152
Val Asp Asp Gly Val Lys Gly Val Ala Phe Val Thr Ala Cys Ile Glu
    370                 375                 380 tcc ggc aag aag aac ggt gtc tgg gtg aag ctg taa                     1188
Ser Gly Lys Lys Asn Gly Val Trp Val Lys Leu
385                 390                 395

<210> SEQ ID NO 12
<211> LENGTH: 395
<212> TYPE: PRT
<213> ORGANISM: Agrobacterium sp.

<400> SEQUENCE: 12

Met Ala Ile Glu Gly Lys Thr Thr Asp Lys Ala Asn Lys Arg Ile Arg
1               5                   10                  15

Leu Gly Met Val Gly Gly Gly Ser Gly Ala Phe Ile Gly Gly Val His
                20                  25                  30

Arg Met Ala Ala Arg Leu Asp Asn Arg Phe Asp Leu Val Ala Gly Ala
            35                  40                  45

Leu Ser Ser Thr Pro Glu Lys Ser Leu Ala Ser Gly Arg Glu Leu Gly
        50                  55                  60

Leu Asp Pro Glu Arg Cys Tyr Gly Ser Phe Glu Glu Met Ala Glu Lys
65                  70                  75                  80

Glu Ala Leu Arg Glu Asp Gly Ile Glu Ala Val Ala Ile Val Thr Pro
                85                  90                  95

Asn His Val His Tyr Pro Ala Ala Lys Ala Phe Leu Glu Arg Gly Ile
            100                 105                 110

His Val Ile Cys Asp Lys Pro Leu Thr Ser Asn Leu Glu Asp Ala Lys
        115                 120                 125

Lys Leu Lys Asp Val Ala Asp Lys Ala Asp Ala Leu Phe Ile Leu Thr
    130                 135                 140

His Asn Tyr Thr Gly Tyr Pro Met Val Arg His Ala Arg Glu Leu Val
145                 150                 155                 160

Glu Ser Gly Ala Leu Gly Thr Ile Arg Leu Val Gln Met Glu Tyr Pro
                165                 170                 175
```

```
Gln Asp Trp Leu Ala Glu Pro Ile Glu Gln Thr Gly Ala Lys Gln Ala
            180                 185                 190

Val Trp Arg Thr Asp Pro Ala Gln Ser Gly Ala Gly Gly Ser Thr Gly
        195                 200                 205

Asp Ile Gly Thr His Ala Tyr Asn Leu Gly Cys Phe Ile Ser Gly Leu
210                 215                 220

Glu Val Asp Glu Leu Ala Ala Asp Val His Thr Phe Val Glu Gly Arg
225                 230                 235                 240

Arg Leu Asp Asp Asn Ala His Val Met Leu Arg Phe Lys Pro Lys Gly
                245                 250                 255

Gly Lys Gln Pro Ala Lys Gly Leu Leu Trp Cys Ser Gln Val Ala Val
            260                 265                 270

Gly His Glu Asn Gly Leu Lys Val Arg Val Tyr Gly Asp Lys Ala Gly
        275                 280                 285

Ile Glu Trp Thr Gln Ala Asp Pro Asn Tyr Leu Trp Phe Thr Lys Leu
290                 295                 300

Gly Glu Leu Lys Gln Leu Ile Thr Arg Gly Gly Ala Gly Ala Gly Ala
305                 310                 315                 320

Ala Ala Ala Arg Val Thr Arg Ile Pro Ser Gly His Pro Glu Gly Tyr
                325                 330                 335

Leu Glu Ala Phe Ala Thr Ile Tyr Thr Glu Ala Ala His Ala Ile Glu
            340                 345                 350

Ala Arg Arg Thr Gly Ser Val Leu Asp Lys Ala Val Ile Tyr Pro Thr
        355                 360                 365

Val Asp Asp Gly Val Lys Gly Val Ala Phe Val Thr Ala Cys Ile Glu
370                 375                 380

Ser Gly Lys Lys Asn Gly Val Trp Val Lys Leu
385                 390                 395

<210> SEQ ID NO 13
<211> LENGTH: 1059
<212> TYPE: DNA
<213> ORGANISM: Xanthomonas campestris pv. campestris
<220> FEATURE:
<221> NAME/KEY: CDS
<222> LOCATION: (1)..(1059)
<223> OTHER INFORMAT -continued

```
ttc gcc ctg gat gcc gca cag gct cgc acc gtg gtg gac gcc gcc gca      336
Phe Ala Leu Asp Ala Ala Gln Ala Arg Thr Val Val Asp Ala Ala Ala
            100                 105                 110 gag gcc ggc aag atc gtc agc gtg ttc cag aac cgc cgt tgg gat gcg      384
Glu Ala Gly Lys Ile Val Ser Val Phe Gln Asn Arg Arg Trp Asp Ala
        115                 120                 125 gac ttc ctc acc gtg cgg cgc ttg atc gaa gac ggc caa ctg ggc gag      432
Asp Phe Leu Thr Val Arg Arg Leu Ile Glu Asp Gly Gln Leu Gly Glu
    130                 135                 140 gtg gtg gag ttc cat tcg cac ttc gac cgg tat cgc ccg cag gtg cgc      480
Val Val Glu Phe His Ser His Phe Asp Arg Tyr Arg Pro Gln Val Arg
145                 150                 155                 160 gac cgc tgg cgc gaa agc gat atc ccc ggc gcc ggg ctg tgg tac gac      528
Asp Arg Trp Arg Glu Ser Asp Ile Pro Gly Ala Gly Leu Trp Tyr Asp
                165                 170                 175 ctg ggg ccg cat ctg ctg gac cag gcg ttg cag ttg ttc ggc atg ccg      576
Leu Gly Pro His Leu Leu Asp Gln Ala Leu Gln Leu Phe Gly Met Pro
            180                 185                 190 cag gcg atc agc gca gac ctg cag cgc cag cgc acc cag gcg cgc agc      624
Gln Ala Ile Ser Ala Asp Leu Gln Arg Gln Arg Thr Gln Ala Arg Ser
        195                 200                 205 gac gat tac ttc aac gtg gtg ctg cgc tat ccc cgc ttg cgg gtg atc      672
Asp Asp Tyr Phe Asn Val Val Leu Arg Tyr Pro Arg Leu Arg Val Ile
    210                 215                 220 ctg cac gcc ggc tcg ctg gtg gcc gac ggc agc ctg cgc ttc gcc gtg      720
Leu His Ala Gly Ser Leu Val Ala Asp Gly Ser Leu Arg Phe Ala Val
225                 230                 235                 240 cac ggc acg cgc ggc agc tat ctc aag cat ggc gcc gat acg cag gaa      768
His Gly Thr Arg Gly Ser Tyr Leu Lys His Gly Ala Asp Thr Gln Glu
                245                 250                 255 gac cag ttg cgt gcc ggc cgc cgg ccc ggc acc gcc ggc tgg ggc atg      816
Asp Gln Leu Arg Ala Gly Arg Arg Pro Gly Thr Ala Gly Trp Gly Met
            260                 265                 270 gac cca ttg ccc ggc acg ctc acc cgc gtg gac gac gaa ggc cgt gtg      864
Asp Pro Leu Pro Gly Thr Leu Thr Arg Val Asp Asp Glu Gly Arg Val
        275                 280                 285 cac acg cat cag ccc gat ggc gta ccc ggc gac tac cgc cat tgc tat      912
His Thr His Gln Pro Asp Gly Val Pro Gly Asp Tyr Arg His Cys Tyr
    290                 295                 300 gcg gcc ttc cgc gac gca atg gcc ggc acc gca ccg cca ccg gtc agt      960
Ala Ala Phe Arg Asp Ala Met Ala Gly Thr Ala Pro Pro Pro Val Ser
305                 310                 315                 320 gct gcc gac gcg gtg cgg ctg atg gag ctg ctg gag ctg gcg caa cgc     1008
Ala Ala Asp Ala Val Arg Leu Met Glu Leu Leu Glu Leu Ala Gln Arg
                325                 330                 335 ggt gct gcg ctg ggc cag gtg ctc tgg ctg gaa ggc aac agc agc gac     1056
Gly Ala Ala Leu Gly Gln Val Leu Trp Leu Glu Gly Asn Ser Ser Asp
            340                 345                 350 tga                                                                 1059
```

<210> SEQ ID NO 14
<211> LENGTH: 352
<212> TYPE: PRT
<213> ORGANISM: Xanthomonas campestris pv. campestris

<400> SEQUENCE: 14

```
Met Pro Lys Pro Phe Asn Leu Ala Val Val Gly Tyr Gly Tyr Val Gly
1               5                   10                  15

Arg Thr Phe His Ala Pro Leu Ile Ala Ser Thr Pro Gly Leu Gln Leu
            20                  25                  30
```

His Ser Val Val Ser Ser Lys Pro Gln Gln Pro Gln Ala Asp Phe Arg
            35                  40                  45

Glu Val Arg Val Leu Pro Asp Leu Glu Ala Ala Leu Ala Asp Pro Ala
 50                  55                  60

Leu Asp Ala Val Val Ile Ala Thr Pro Asn Gln Thr His Ala Pro Met
 65                  70                  75                  80

Ala Leu Gln Ala Leu Ala Ala Gly Lys His Val Leu Val Asp Lys Pro
                85                  90                  95

Phe Ala Leu Asp Ala Ala Gln Ala Arg Thr Val Val Asp Ala Ala Ala
            100                 105                 110

Glu Ala Gly Lys Ile Val Ser Val Phe Gln Asn Arg Arg Trp Asp Ala
            115                 120                 125

Asp Phe Leu Thr Val Arg Arg Leu Ile Glu Asp Gly Gln Leu Gly Glu
            130                 135                 140

Val Val Glu Phe His Ser His Phe Asp Arg Tyr Arg Pro Gln Val Arg
145                 150                 155                 160

Asp Arg Trp Arg Glu Ser Asp Ile Pro Gly Ala Gly Leu Trp Tyr Asp
                165                 170                 175

Leu Gly Pro His Leu Leu Asp Gln Ala Leu Gln Leu Phe Gly Met Pro
            180                 185                 190

Gln Ala Ile Ser Ala Asp Leu Gln Arg Gln Thr Gln Ala Arg Ser
            195                 200                 205

Asp Asp Tyr Phe Asn Val Val Leu Arg Tyr Pro Arg Leu Arg Val Ile
            210                 215                 220

Leu His Ala Gly Ser Leu Val Ala Asp Gly Ser Leu Arg Phe Ala Val
225                 230                 235                 240

His Gly Thr Arg Gly Ser Tyr Leu Lys His Gly Ala Asp Thr Gln Glu
                245                 250                 255

Asp Gln Leu Arg Ala Gly Arg Arg Pro Gly Thr Ala Gly Trp Gly Met
            260                 265                 270

Asp Pro Leu Pro Gly Thr Leu Thr Arg Val Asp Asp Glu Gly Arg Val
            275                 280                 285

His Thr His Gln Pro Asp Gly Val Pro Gly Asp Tyr Arg His Cys Tyr
            290                 295                 300

Ala Ala Phe Arg Asp Ala Met Ala Gly Thr Ala Pro Pro Val Ser
305                 310                 315                 320

Ala Ala Asp Ala Val Arg Leu Met Glu Leu Leu Glu Leu Ala Gln Arg
                325                 330                 335

Gly Ala Ala Leu Gly Gln Val Leu Trp Leu Glu Gly Asn Ser Ser Asp
            340                 345                 350

<210> SEQ ID NO 15
<211> LENGTH: 34
<212> TYPE: DNA
<213> ORGANISM: Artificial
<220> FEATURE:
<223> OTHER INFORMATION: primer

<400> SEQUENCE: 15
cattcaagct taatgagagg caatgacatg agcg                              34

<210> SEQ ID NO 16
<211> LENGTH: 31
<212> TYPE: DNA
<213> ORGANISM: Artificial
<220> FEATURE:

<223> OTHER INFORMATION: primer

<400> SEQUENCE: 16
tcggaattct tcatgcaagg cacaaagtcg c                            31

<210> SEQ ID NO 17
<211> LENGTH: 32
<212> TYPE: DNA
<213> ORGANISM: Artificial
<220> FEATURE:
<223> OTHER INFORMATION: primer

<400> SEQUENCE: 17
ggcggatcct ttgaaaggga tagtcatgtc ct                           32

<210> SEQ ID NO 18
<211> LENGTH: 29
<212> TYPE: DNA
<213> ORGANISM: Artificial
<220> FEATURE:
<223> OTHER INFORMATION: primer

<400> SEQUENCE: 18
attggaagct tcgattggct gcgacctag                               29

<210> SEQ ID NO 19
<211> LENGTH: 30
<212> TYPE: DNA
<213> ORGANISM: Artificial
<220> FEATURE:
<223> OTHER INFORMATION: primer

<400> SEQUENCE: 19
ttgggatcct ttcagggaa atattatggc                               30

<210> SEQ ID NO 20
<211> LENGTH: 26
<212> TYPE: DNA
<213> ORGANISM: Artificial
<220> FEATURE:
<223> OTHER INFORMATION: primer

<400> SEQUENCE: 20
gccgcaagct tgttttacag cttcac                                  26

<210> SEQ ID NO 21
<211> LENGTH: 34
<212> TYPE: DNA
<213> ORGANISM: Artificial
<220> FEATURE:
<223> OTHER INFORMATION: primer

<400> SEQUENCE: 21
aggaattcga tgataacgct tttaaagggg agaa                         34

<210> SEQ ID NO 22
<211> LENGTH: 34
<212> TYPE: DNA
<213> ORGANISM: Artificial
<220> FEATURE:
<223> OTHER INFORMATION: primer

<400> SEQUENCE: 22
tttctgcagt ttagtgctcc agcataatgg ttcg                         34

<210> SEQ ID NO 23
<211> LENGTH: 34
<212> TYPE: DNA
<213> ORGANISM: Artificial
<220> FEATURE:
<223> OTHER INFORMATION: primer

<400> SEQUENCE: 23
tcggaattcg cgttgcggtg aatcgttttc aatg                            34

<210> SEQ ID NO 24
<211> LENGTH: 34
<212> TYPE: DNA
<213> ORGANISM: Artificial
<220> FEATURE:
<223> OTHER INFORMATION: primer

<400> SEQUENCE: 24
ataagaagct tgctcagtcg ctgctgttgc cttc                            34

<210> SEQ ID NO 25
<211> LENGTH: 35
<212> TYPE: DNA
<213> ORGANISM: Artificial
<220> FEATURE:
<223> OTHER INFORMATION: primer

<400> SEQUENCE: 25
ttgggatccg atgagtttac gtattggcgt aattg                           35

<210> SEQ ID NO 26
<211> LENGTH: 39
<212> TYPE: DNA
<213> ORGANISM: Artificial
<220> FEATURE:
<223> OTHER INFORMATION: primer

<400> SEQUENCE: 26
aaactgcagt tagttttgaa ctgttgtaaa agattgata                       39

<210> SEQ ID NO 27
<211> LENGTH: 1179
<212> TYPE: DNA
<213> ORGANISM: Acetobacter sp.
<220> FEATURE:
<221> NAME/KEY: CDS
<222> LOCATION: (1)..(1179)
<223> OTHER INFORMATION:

<400> SEQUENCE: 27

```
atg acc aaa cgt aaa ttg cgc att ggc ctg att ggc agt ggg ttc atg      48
Met Thr Lys Arg Lys Leu Arg Ile Gly Leu Ile Gly Ser Gly Phe Met
1               5                   10                  15 ggg cgc acc cac gcc ttt ggc tat tca acc gcg tcc cgt gtg ttt gat      96
Gly Arg Thr His Ala Phe Gly Tyr Ser Thr Ala Ser Arg Val Phe Asp
            20                  25                  30 ctt ccg ttt cag ccg gag ctg acg tgc ctg gct gat att tcc gat gaa     144
Leu Pro Phe Gln Pro Glu Leu Thr Cys Leu Ala Asp Ile Ser Asp Glu
        35                  40                  45 gct gca gcg aag gcg gcg gat gct ctg gga ttt gcc cgt tcc acc agt     192
Ala Ala Ala Lys Ala Ala Asp Ala Leu Gly Phe Ala Arg Ser Thr Ser
    50                  55                  60 gac tgg cgt acg ctc gtc aac gat cct gaa att gat gtg gtg aat atc     240
Asp Trp Arg Thr Leu Val Asn Asp Pro Glu Ile Asp Val Val Asn Ile
65                  70                  75                  80
```

```
                                                   -continued
acg gcg cct aat gcc ttt cat aaa gaa atg gcg tta gca gcg att gct    288
Thr Ala Pro Asn Ala Phe His Lys Glu Met Ala Leu Ala Ala Ile Ala
                 85                  90                  95 gcg ggc aag cat gtc tat tgt gaa aag ccc ctt gcg cca ctt gca gcc    336
Ala Gly Lys His Val Tyr Cys Glu Lys Pro Leu Ala Pro Leu Ala Ala
            100                 105                 110 gat gct cgc gaa atg gca gaa gcg gct gag gca aag ggc gta aaa aca    384
Asp Ala Arg Glu Met Ala Glu Ala Ala Glu Ala Lys Gly Val Lys Thr
        115                 120                 125 cag gtt ggc ttc aac tac ctg tgc aac ccc atg ctg gca ctg gcc cga    432
Gln Val Gly Phe Asn Tyr Leu Cys Asn Pro Met Leu Ala Leu Ala Arg
    130                 135                 140 gat atg att gca gca ggg gag ctg ggg gaa atc aga ggg tac cgt ggc    480
Asp Met Ile Ala Ala Gly Glu Leu Gly Glu Ile Arg Gly Tyr Arg Gly
145                 150                 155                 160 ctg cat gcg gaa gat tat atg gcg gac gcc tcg tct ccc ttt acg ttc    528
Leu His Ala Glu Asp Tyr Met Ala Asp Ala Ser Ser Pro Phe Thr Phe
                165                 170                 175 cgt ctt gac cca gcg gga ggc ggc gca ctt gct gat att ggg agt cac    576
Arg Leu Asp Pro Ala Gly Gly Gly Ala Leu Ala Asp Ile Gly Ser His
            180                 185                 190 gcc ctt gca acg gct gaa ttt ctt atg ggg cct gcc gca ggc gct atc    624
Ala Leu Ala Thr Ala Glu Phe Leu Met Gly Pro Ala Ala Gly Ala Ile
        195                 200                 205 acg cag gtg atg ggg gat tgt gtg acg gtc atc aag acg cgg ccg gat    672
Thr Gln Val Met Gly Asp Cys Val Thr Val Ile Lys Thr Arg Pro Asp
    210                 215                 220 ggt aag ggg gga acg cgg gct gta gaa gtg gac gat att ggc cgc gcg    720
Gly Lys Gly Gly Thr Arg Ala Val Glu Val Asp Asp Ile Gly Arg Ala
225                 230                 235                 240 ctt ctg cgc ttt gag aat ggg gcg acg gga tcg gtt gag gga aac tgg    768
Leu Leu Arg Phe Glu Asn Gly Ala Thr Gly Ser Val Glu Gly Asn Trp
                245                 250                 255 att gct acc ggc cgc acc atg cag cat gac ttt gag gta tac ggc aca    816
Ile Ala Thr Gly Arg Thr Met Gln His Asp Phe Glu Val Tyr Gly Thr
            260                 265                 270 aaa ggt gca ctt gcc ttt act cag caa cga ttt aac gag ttg cat ttc    864
Lys Gly Ala Leu Ala Phe Thr Gln Gln Arg Phe Asn Glu Leu His Phe
        275                 280                 285 ttc tca agc acc gat gca cgc ggc cgc aaa ggg ttc cgg cgt att gaa    912
Phe Ser Ser Thr Asp Ala Arg Gly Arg Lys Gly Phe Arg Arg Ile Glu
    290                 295                 300 gcg gga cca gag cat gcg ccc tat ggc ctg ttc tgc gtg gca ccg ggg    960
Ala Gly Pro Glu His Ala Pro Tyr Gly Leu Phe Cys Val Ala Pro Gly
305                 310                 315                 320 cac cag ctg ggt ttt aat gac ctc aag gcg ata gaa gtt gca cgg tat    1008
His Gln Leu Gly Phe Asn Asp Leu Lys Ala Ile Glu Val Ala Arg Tyr
                325                 330                 335 ctg gag gcg ctg gct ggc cat cac cct gaa ccc ttc aat ttc cgg gcg    1056
Leu Glu Ala Leu Ala Gly His His Pro Glu Pro Phe Asn Phe Arg Ala
            340                 345                 350 ggt ctg cgt atc cag aca ctg gtg gaa act att cac gct tca agc aag    1104
Gly Leu Arg Ile Gln Thr Leu Val Glu Thr Ile His Ala Ser Ser Lys
        355                 360                 365 tcg gct gcc tgg cgg gat gtg ccg acg gac aaa gtg aag ctt cag gcg    1152
Ser Ala Ala Trp Arg Asp Val Pro Thr Asp Lys Val Lys Leu Gln Ala
    370                 375                 380 aaa tcc cga cag cat gag aag gca taa                                1179
Lys Ser Arg Gln His Glu Lys Ala
385                 390
```

<210> SEQ ID NO 28
<211> LENGTH: 392
<212> TYPE: PRT
<213> ORGANISM: Acetobacter sp.

<400> SEQUENCE: 28

Met Thr Lys Arg Lys Leu Arg Ile Gly Leu Ile Gly Ser Gly Phe Met
1               5                   10                  15

Gly Arg Thr His Ala Phe Gly Tyr Ser Thr Ala Ser Arg Val Phe Asp
            20                  25                  30

Leu Pro Phe Gln Pro Glu Leu Thr Cys Leu Ala Asp Ile Ser Asp Glu
        35                  40                  45

Ala Ala Ala Lys Ala Ala Asp Ala Leu Gly Phe Ala Arg Ser Thr Ser
    50                  55                  60

Asp Trp Arg Thr Leu Val Asn Asp Pro Glu Ile Asp Val Val Asn Ile
65                  70                  75                  80

Thr Ala Pro Asn Ala Phe His Lys Glu Met Ala Leu Ala Ala Ile Ala
                85                  90                  95

Ala Gly Lys His Val Tyr Cys Glu Lys Pro Leu Ala Pro Leu Ala Ala
            100                 105                 110

Asp Ala Arg Glu Met Ala Glu Ala Ala Glu Ala Lys Gly Val Lys Thr
        115                 120                 125

Gln Val Gly Phe Asn Tyr Leu Cys Asn Pro Met Leu Ala Leu Ala Arg
    130                 135                 140

Asp Met Ile Ala Ala Gly Glu Leu Gly Glu Ile Arg Gly Tyr Arg Gly
145                 150                 155                 160

Leu His Ala Glu Asp Tyr Met Ala Asp Ala Ser Ser Pro Phe Thr Phe
                165                 170                 175

Arg Leu Asp Pro Ala Gly Gly Ala Leu Ala Asp Ile Gly Ser His
            180                 185                 190

Ala Leu Ala Thr Ala Glu Phe Leu Met Gly Pro Ala Ala Gly Ala Ile
        195                 200                 205

Thr Gln Val Met Gly Asp Cys Val Thr Val Ile Lys Thr Arg Pro Asp
    210                 215                 220

Gly Lys Gly Gly Thr Arg Ala Val Glu Val Asp Asp Ile Gly Arg Ala
225                 230                 235                 240

Leu Leu Arg Phe Glu Asn Gly Ala Thr Gly Ser Val Glu Gly Asn Trp
                245                 250                 255

Ile Ala Thr Gly Arg Thr Met Gln His Asp Phe Glu Val Tyr Gly Thr
            260                 265                 270

Lys Gly Ala Leu Ala Phe Thr Gln Gln Arg Phe Asn Glu Leu His Phe
        275                 280                 285

Phe Ser Ser Thr Asp Ala Arg Gly Arg Lys Gly Phe Arg Arg Ile Glu
    290                 295                 300

Ala Gly Pro Glu His Ala Pro Tyr Gly Leu Phe Cys Val Ala Pro Gly
305                 310                 315                 320

His Gln Leu Gly Phe Asn Asp Leu Lys Ala Ile Glu Val Ala Arg Tyr
                325                 330                 335

Leu Glu Ala Leu Ala Gly His His Pro Glu Pro Phe Asn Phe Arg Ala
            340                 345                 350

Gly Leu Arg Ile Gln Thr Leu Val Glu Thr Ile His Ala Ser Ser Lys
        355                 360                 365

Ser Ala Ala Trp Arg Asp Val Pro Thr Asp Lys Val Lys Leu Gln Ala

```
                   370                 375                 380
Lys Ser Arg Gln His Glu Lys Ala
385                 390

<210> SEQ ID NO 29
<211> LENGTH: 32
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (9), (15)
<223> OTHER INFORMATION: n=a, t, g or c
<220> FEATURE:
<221> NAME/KEY: misc_feature
<222> LOCATION: (18), (27)
<223> OTHER INFORMATION: n=inosine

<400> SEQUENCE: 29
atgaarcgna arytncgnat yggyytnaty gg                                    32

<210> SEQ ID NO 30
<211> LENGTH: 32
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (15)
<223> OTHER INFORMATION: n=a, t, g or c
<220> FEATURE:
<221> NAME/KEY: misc_feature
<222> LOCATION: (18), (24)
<223> OTHER INFORMATION: n=inosine

<400> SEQUENCE: 30
ggyttyatgg gycgnacnca ygcnttyggy ta                                    32

<210> SEQ ID NO 31
<211> LENGTH: 26
<212> TYPE: DNA
<213> ORGANISM: Artificial
<220> FEATURE:
<223> OTHER INFORMATION: primer

<400> SEQUENCE: 31
ggyttrtcrm mgayracrtg rstrcc                                           26

<210> SEQ ID NO 32
<211> LENGTH: 19
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (7), (17)
<223> OTHER INFORMATION: n=inosine

<400> SEQUENCE: 32
artgwrnrtg rttgggngt                                                   19

<210> SEQ ID NO 33
<211> LENGTH: 25
<212> TYPE: DNA
<213> ORGANISM: Artificial
<220> FEATURE:
```

-continued

```
<223> OTHER INFORMATION: primer

<400> SEQUENCE: 33
gctcgtcaac gatcctgaaa ttgat                                          25

<210> SEQ ID NO 34
<211> LENGTH: 25
<212> TYPE: DNA
<213> ORGANISM: Artificial
<220> FEATURE:
<223> OTHER INFORMATION: primer

<400> SEQUENCE: 34
ttcgctgcag cttcatcgga aatat                                          25

<210> SEQ ID NO 35
<211> LENGTH: 21
<212> TYPE: DNA
<213> ORGANISM: Artificial
<220> FEATURE:
<223> OTHER INFORMATION: primer

<400> SEQUENCE: 35
cccttcaatt tccgggcggg t                                              21

<210> SEQ ID NO 36
<211> LENGTH: 26
<212> TYPE: DNA
<213> ORGANISM: Artificial
<220> FEATURE:
<223> OTHER INFORMATION: primer

<400> SEQUENCE: 36
gctggatccc gcccttattg tgaata                                         26

<210> SEQ ID NO 37
<211> LENGTH: 31
<212> TYPE: DNA
<213> ORGANISM: Artificial
<220> FEATURE:
<223> OTHER INFORMATION: primer

<400> SEQUENCE: 37
tatgaattcg ttatgccttc tcatgctgtc g                                   31
```